United States Patent
Omura et al.

(10) Patent No.: US 7,737,305 B2
(45) Date of Patent: Jun. 15, 2010

(54) SULFONIC ACID POLYOL COMPOUND, POLYURETHANE RESIN, POLYURETHANE RESIN FOR MAGNETIC RECORDING MEDIUM, AND MAGNETIC RECORDING MEDIUM

(75) Inventors: Kazufumi Omura, Kanagawa (JP); Masahiko Mori, Kanagawa (JP); Katsumi Araki, Kanagawa (JP); Masataka Yoshizawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/490,520

(22) Filed: Jun. 24, 2009

(65) Prior Publication Data
US 2009/0258254 A1 Oct. 15, 2009

Related U.S. Application Data

(62) Division of application No. 12/235,709, filed on Sep. 23, 2008.

(30) Foreign Application Priority Data

Sep. 28, 2007 (JP) ............................. 2007-255614
Sep. 28, 2007 (JP) ............................. 2007-255639

(51) Int. Cl.
*C07C 321/00* (2006.01)
*C07C 323/00* (2006.01)
*C07C 381/00* (2006.01)
*C08G 18/00* (2006.01)
*G11B 5/708* (2006.01)
*G11B 5/33* (2006.01)

(52) U.S. Cl. ...................... 564/500; 528/65; 428/842.3; 428/800

(58) Field of Classification Search ................ None
See application file for complete search history.

(56) References Cited

U.S. PATENT DOCUMENTS 3,084,187 A * 4/1963 Gaertner .................... 562/107

FOREIGN PATENT DOCUMENTS

| DE | 60382 | * 11/1968 |
| DE | 1617077 | * 2/1971 |
| JP | 03-066660 A | 3/1991 |
| JP | 05-070545 A | 3/1993 |
| JP | 09-138939 A | 5/1997 |

* cited by examiner

*Primary Examiner*—Daniel M Sullivan
*Assistant Examiner*—Clinton Brooks
(74) *Attorney, Agent, or Firm*—Sughrue Mion, PLLC

(57) ABSTRACT

A compound represented by the Formula (1) below is provided:

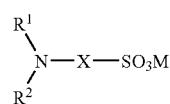

(1)

wherein X denotes a divalent linking group, $R^1$ and $R^2$ independently denote an alkyl group having 3 or more carbons and having at least one hydroxy group or an aralkyl group having 8 or more carbons and having at least one hydroxy group, the alkyl group and aralkyl group may have a substituent, and M denotes a hydrogen atom or a cation. There is also provided a polyurethane resin obtained by polymerization of a polyisocyanate and a polyol that includes the compound. There is also provided a magnetic recording medium that includes a non-magnetic support and, above the support, at least one magnetic layer including a ferromagnetic powder dispersed in a binder that includes the polyurethane resin. There is also provided a magnetic recording medium that includes a non-magnetic support, above the support at least one non-magnetic layer including a non-magnetic powder dispersed in a binder (1), and, above the non-magnetic layer, at least one magnetic layer having a ferromagnetic powder dispersed in a binder (2), in which binder (1) and/or binder (2) is the polyurethane resin.

9 Claims, No Drawings

SULFONIC ACID POLYOL COMPOUND, POLYURETHANE RESIN, POLYURETHANE RESIN FOR MAGNETIC RECORDING MEDIUM, AND MAGNETIC RECORDING MEDIUM

CROSS REFERENCE TO RELATED APPLICATIONS

This is a divisional of application Ser. No. 12/235,709 filed Sep. 23, 2008. The entire disclosure of the prior application, application Ser. No. 12/235,709, is considered part of the disclosure of the accompanying divisional application and is hereby incorporated by reference.

BACKGROUND OF THE INVENTION

1. Field of the Invention

The present invention relates to a sulfonic acid polyol compound, a polyurethane resin, a polyurethane resin for a magnetic recording medium, and a magnetic recording medium.

2. Description of the Related Art

Sulfonic acid compounds are generally highly water-soluble but organic solvent-insoluble compounds, and the use thereof as synthetic organic chemicals is limited. For example, N,N-bis(2-hydroxyethyl)-2-aminoethanesulfonic acid (CAS No: 10191-18-1) is a sulfonic acid compound that has two hydroxy groups but does not dissolve in organic solvents, and the application thereof is therefore limited to reactions in a heterogeneous system or reactions in an aqueous system.

Furthermore, JP-A-3-66660 (JP-A denotes a Japanese unexamined patent application publication) discloses a method for producing an N,N-bis(hydroxyethyl)aminoethylsulfonic acid salt, etc.

Magnetic recording technology has the excellent features, not seen in other recording methods, that the medium can be used repeatedly, signals are easily converted to electronic form and it is possible to build a system in combination with peripheral equipment, and signals can easily be corrected, and is therefore widely used in various fields including video, audio, and computer applications.

In general, with the demand for higher recording density in magnetic recording media for computer use, etc., it is necessary to yet further improve the electromagnetic conversion characteristics, and it is important to make a ferromagnetic powder finer, the surface of the medium ultra smooth, etc.

With regard to making a magnetic substance finer, a ferromagnetic metal powder of no greater than 0.1 μm or a ferromagnetic hexagonal ferrite fine powder having a plate size of no greater than 40 nm has recently been used as a magnetic substance. In the case of a multilayer structure in which a magnetic layer is provided as an upper layer after a non-magnetic lower layer is provided on the surface of a support, in order to highly disperse in a binder a fine non-magnetic powder used for the non-magnetic layer or the fine magnetic substance above, a dispersion technique has been proposed in which a hydroxy group or the hydrophilic polar group —$SO_3M$ (M denotes hydrogen, an alkali metal, or an ammonium salt) is introduced into the binder, and a binder chain is made to adsorb on the magnetic substance or the non-magnetic powder via the polar group so as to achieve a smooth surface.

For example, JP-A-9-138939 discloses a magnetic recording medium in which a magnetic material having a ferromagnetic powder dispersed in a binder is applied onto a non-magnetic support, wherein the magnetic layer comprises as a binder component a polyurethane resin formed from a high molecular weight polyol having a molecular weight of at least 500 (A), an organic diisocyanate (B), and as necessary a polyol compound having a molecular weight of no greater than 500 (C), the high molecular weight polyol (A) comprising a hydrophilic polar group-containing aromatic polyester diol (A-1) whose dibasic acid component is an aromatic dibasic acid, and another high molecular weight polyol (A-2).

Furthermore, JP-A-5-70545 discloses a polyether polyurethane resin in which a polyol molecule component and a polyether molecule component are chain-extended via a urethane bond, the resin having a weight-average molecular weight of 20,000 to 200,000 and the polyether component being a polyether polyol employing as an initiator a low molecular weight diol having an $SO_3M$ group (M is an alkali metal atom or a hydrogen atom), a binder for a magnetic recording medium comprising the polyurethane resin, and a magnetic recording medium.

BRIEF SUMMARY OF THE INVENTION

It is an object of the present invention to provide a sulfonic acid polyol compound having excellent solubility in an organic solvent. Furthermore, it is another object of the present invention to provide a polyurethane resin that can give a magnetic recording medium having excellent dispersion properties, coating smoothness, and electromagnetic conversion characteristics, and excellent transport durability, and a magnetic recording medium employing the polyurethane resin.

The objects above can be attained by means described in <1>, <6>, and <11>. They are described below together with <2> to <5>, <7> to <10>, and <12> to <14>, which are preferred embodiments.

<1> A compound represented by Formula (1) below,

(1)

wherein X denotes a divalent linking group, $R^1$ and $R^2$ independently denote an alkyl group having 3 or more carbons and having at least one hydroxy group or an aralkyl group having 8 or more carbons and having at least one hydroxy group, the alkyl group and aralkyl group may have a substituent, and M denotes a hydrogen atom or a cation, <2> the compound according to <1> above, wherein it is a compound represented by Formula (2) below and/or Formula (3) below,

(2)

-continued

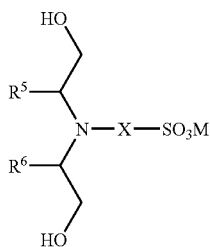

(3)

wherein X denotes a divalent linking group, $R^3$, $R^4$, $R^5$, and $R^6$ independently denote an alkyl group having 2 to 20 carbons, an aryl group having 6 to 20 carbons, an aralkyl group having 7 to 20 carbons, an alkoxyalkyl group having 2 to 20 carbons, or an aryloxyalkyl group having 7 to 20 carbons, and M denotes a hydrogen atom or a cation, <3> the compound according to <1> or <2> above, wherein X is an ethylene group or a phenylene group, <4> the compound according to any one of <1> to <3> above, wherein M is an inorganic cation, <5> the compound according to any one of <1> to <4> above, wherein M is an alkali metal ion, <6> a polyurethane resin obtained by polymerization of a polyol and a polyisocyanate, wherein the polyol comprises the compound according to any one of <1> to <5> above, <7> the polyurethane resin according to <6> above, wherein the polyol comprises a compound represented by Formula (2) above and a compound represented by Formula (3) above, <8> the polyurethane resin according to <6> or <7> above, wherein it has a sulfonic acid (salt) group content of at least $1 \times 10^{-5}$ eq/g but no greater than $2 \times 10^{-3}$ eq/g, <9> the polyurethane resin according to any one of <6> to <8> above, wherein the polyol further comprises a (meth) acryloyloxy group-containing diol, <10> the polyurethane resin according to any one of <6> to <9> above, wherein it is intended for use in a magnetic recording medium, <11> a magnetic recording medium comprising a non-magnetic support and, above the support, at least one magnetic layer comprising a ferromagnetic powder dispersed in a binder, the binder comprising the polyurethane resin according to any one of <6> to <10> above, <12> a magnetic recording medium comprising a non-magnetic support, above the support at least one non-magnetic layer comprising a non-magnetic powder dispersed in a binder (1), and, above the non-magnetic layer, at least one magnetic layer comprising a ferromagnetic powder dispersed in a binder (2), binder (1) and/or binder (2) being the polyurethane resin according to any one of <6> to <10> above, <13> the magnetic recording medium according to <12> above, wherein binder (1) comprises the polyurethane resin according to <9> above, and <14> the magnetic recording medium according to any one of <11> to <13> above, wherein the ferromagnetic powder is at least one type selected from the group consisting of an acicular ferromagnetic substance having a major axis length of at least 20 nm but no greater than 50 nm, a tabular ferromagnetic substance having a plate size of at least 10 nm but no greater than 50 nm, and a spherical or spheroidal magnetic substance having a diameter of at least 10 nm but no greater than 50 nm.

DETAILED DESCRIPTION OF THE INVENTION (1) Compound Represented by Formula (1)

The compound of the present invention is represented by Formula (1).

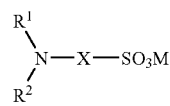

(1)

(In Formula (1), X denotes a divalent linking group, $R^1$ and $R^2$ independently denote an alkyl group having 3 or more carbons and having at least one hydroxy group or an aralkyl group having 8 or more carbons and having at least one hydroxy group, the alkyl group and the aralkyl group may have a substituent, and M denotes a hydrogen atom or a cation.)

The compound of the present invention is a sulfonic acid polyol compound, and is a compound having excellent solubility in an organic solvent compared with other sulfonic acid polyol compounds.

Furthermore, since the compound of the present invention has excellent solubility in an organic solvent and can be used in a homogenous reaction in an organic solvent, it can suitably be used as a substrate for a synthetic reaction, and can be used more suitably as a monomer used in the production of various resins.

Moreover, by using the compound of the present invention in the production of a resin, a homogeneous reaction in an organic solvent can be carried out, and a resin into which a sulfonic acid (salt) group is introduced can easily be produced.

X in Formula (1) denotes a divalent linking group, is preferably a divalent linking group having at least 2 but no more than 20 carbons and is preferably a divalent hydrocarbon group, more preferably an alkylene group, an arylene group, or a group in which two or more of these groups are combined, yet more preferably an alkylene group or an arylene group, particularly preferably an ethylene group or a phenylene group, and most preferably an ethylene group.

Furthermore, examples of the phenylene group include an o-phenylene group, a m-phenylene group, and a p-phenylene group, an o-phenylene group or an m-phenylene group is preferable, and a m-phenylene group is more preferable.

The number of carbons of the alkylene group is preferably at least 2 but no greater than 20, more preferably at least 2 but no greater than 4, and yet more preferably 2. Moreover, the alkylene group may be a straight chain alkylene group or a branched alkylene group, and is preferably a straight chain alkylene group.

The number of carbons of the arylene group is preferably at least 6 but no greater than 20, more preferably at least 6 but no greater than 10, and yet more preferably 6.

The alkylene group and the arylene group may have a substituent shown below, but they are preferably groups comprising only carbon atoms and hydrogen atoms.

Examples of the substituent that the alkylene group may have include an aryl group, a halogen atom (a fluorine atom, a chlorine atom, a bromine atom, an iodine atom), an alkoxy group, an aryloxy group, and an alkyl group.

Examples of the substituent that the arylene group may have include an alkyl group, a halogen atom (a fluorine atom, a chlorine atom, a bromine atom, an iodine atom), an alkoxy group, an aryloxy group, and an aryl group.

$R^1$ and $R^2$ in Formula (1) independently denote an alkyl group having 3 or more carbons and having at least one hydroxy group or an aralkyl group having 8 or more carbons and having at least one hydroxy group, and the alkyl group and the aralkyl group may have a substituent.

Examples of the substituent other than a hydroxy group that the alkyl group and the aralkyl group may have include an alkoxy group, an aryloxy group, a halogen atom (a fluorine atom, a chlorine atom, a bromine atom, an iodine atom), a sulfonyl group, and a silyl group. Among them, an alkoxy group and an aryloxy group are preferable, an alkoxy group having 1 to 20 carbons and an aryloxy group having 6 to 20 carbons are more preferable, and an alkoxy group having 1 to 4 carbons and a phenoxy group are yet more preferable.

Moreover, the alkyl group and the aralkyl group may be straight chain or branched.

The number of hydroxy groups in $R^1$ and $R^2$ is 1 or more, preferably 1 or 2, and particularly preferably 1. That is, the sulfonic acid polyol compound of the present invention is particularly preferably a sulfonic acid diol compound.

The number of carbons in the alkyl group denoted by $R^1$ and $R^2$ is 3 or more, preferably 3 to 22, more preferably 4 to 22, and yet more preferably 4 to 8.

The number of carbons in the aralkyl group denoted by $R^1$ and $R^2$ is 8 or more, preferably 8 to 22, more preferably 8 to 12, and yet more preferably 8. Furthermore, the aralkyl group denoted by $R^1$ and $R^2$ is preferably a hydrocarbon chain in which the α-position and the β-position of a nitrogen atom are saturated. Furthermore, in this case, the β-position of the nitrogen atom may have a hydroxy group.

Furthermore, $R^1$ and $R^2$ preferably have no hydroxy group at the α-position of the nitrogen atom, more preferably have one hydroxy group at least at the β-position of the nitrogen atom, and particularly preferably have one hydroxy group only at the β-position of the nitrogen atom. Having a hydroxy group at the p-position of the nitrogen atom enables synthesis of the compound of the present invention to be carried out easily and the solubility in an organic solvent to be made excellent.

Moreover, $R^1$ and $R^2$ are independently preferably an alkyl group having 3 to 22 carbons and having at least one hydroxy group, an aralkyl group having 8 to 22 carbons and having at least one hydroxy group, an alkoxyalkyl group having 4 to 22 carbons and having at least one hydroxy group, or an aryloxyalkyl group having 9 to 22 carbons and having at least one hydroxy group, and are more preferably an alkyl group having 4 to 22 carbons and having at least one hydroxy group, an aralkyl group having 8 to 22 carbons and having at least one hydroxy group, an alkoxyalkyl group having 4 to 22 carbons and having at least one hydroxy group, or an aryloxyalkyl group having 9 to 22 carbons and having at least one hydroxy group.

Specific examples of the alkyl group having 3 or more carbons and having at least one hydroxy group include a 2-hydroxypropyl group, a 2-hydroxybutyl group, a 2-hydroxypentyl group, a 2-hydroxyhexyl group, a 2-hydroxyoctyl group, a 2-hydroxy-3-methoxypropyl group, a 2-hydroxy-3-ethoxypropyl group, a 2-hydroxy-3-butoxypropyl group, a 2-hydroxy-3-phenoxypropyl group, a 2-hydroxy-3-methoxybutyl group, a 2-hydroxy-3-methoxy-3-methylbutyl group, a 2,3-dihydroxypropyl group, a 3-hydroxypropyl group, a 3-hydroxybutyl group, a 4-hydroxybutyl group, a 1-methyl-2-hydroxyethyl group, a 1-ethyl-2-hydroxyethyl group, a 1-propyl-2-hydroxyethyl group, a 1-butyl-2-hydroxyethyl group, a 1-hexyl-2-hydroxyethyl group, a 1-methoxymethyl-2-hydroxyethyl group, a 1-ethoxymethyl-2-hydroxyethyl group, a 1-butoxymethyl-2-hydroxyethyl group, a 1-phenoxymethyl-2-hydroxyethyl group, a 1-(1-methoxyethyl)-2-hydroxyethyl group, a 1-(1-methoxy-1-methylethyl)-2-hydroxyethyl group, and a 1,3-dihydroxy-2-propyl group. Among them, preferred examples include a 2-hydroxybutyl group, a 2-hydroxy-3-methoxypropyl group, a 2-hydroxy-3-butoxypropyl group, a 2-hydroxy-3-phenoxypropyl group, a 1-methyl-2-hydroxyethyl group, a 1-methoxymethyl-2-hydroxyethyl group, a 1-butoxymethyl-2-hydroxyethyl group, and a 1-phenoxyethyl-2-hydroxyethyl group.

Specific examples of the aralkyl group having 8 or more carbons and having at least one hydroxy group include a 2-hydroxy-2-phenylethyl group, a 2-hydroxy-2-phenylpropyl group, a 2-hydroxy-3-phenylpropyl group, a 2-hydroxy-2-phenylbutyl group, a 2-hydroxy-4-phenylbutyl group, a 2-hydroxy-5-phenylpentyl group, a 2-hydroxy-2-(4-methoxyphenyl)ethyl group, a 2-hydroxy-2-(4-phenoxyphenyl)ethyl group, a 2-hydroxy-2-(3-methoxyphenyl)ethyl group, a 2-hydroxy-2-(4-chlorophenyl)ethyl group, a 2-hydroxy-2-(4-hydroxyphenyl)ethyl group, a 2-hydroxy-3-(4-methoxyphenyl)propyl group, a 2-hydroxy-3-(4-chlorophenyl)propyl group, a 1-phenyl-2-hydroxyethyl group, a 1-methyl-1-phenyl-2-hydroxyethyl group, a 1-benzyl-2-hydroxyethyl group, a 1-ethyl-1-phenyl-2-hydroxyethyl group, a 1-phenethyl-2-hydroxyethyl group, a 1-phenylpropyl-2-hydroxyethyl group, a 1-(4-methoxyphenyl)-2-hydroxyethyl group, a 1-(4-phenoxyphenyl)-2-hydroxyethyl group, a 1-(3-methoxyphenyl)-2-hydroxyethyl group, a 1-(4-chlorophenyl)-2-hydroxyethyl group, a 1-(4-hydroxyphenyl)-2-hydroxyethyl group, and a 1-(4-methoxyphenyl)-3-hydroxy-2-propyl group. Among them, preferred examples include a 2-hydroxy-2-phenylethyl group and a 1-phenyl-2-hydroxyphenyl group.

M in Formula (1) denotes a hydrogen atom or a cation.

The cation may be an inorganic cation or an organic cation. The cation electrically neutralizes —$SO_3^-$ in Formula (1), is not limited to a monovalent cation, and may be a di- or higher-valent cation, but the cation is preferably a monovalent cation. When an n-valent cation is used, it means (1/n) mol of cation relative to the compound represented by Formula (1) above.

The inorganic cation is not particularly limited; preferred examples thereof include alkali metal ions and alkaline earth metal ions, more preferred examples thereof include alkali metal ions, and yet more preferred examples thereof include $Li^+$, $Na^+$, and $K^+$.

Examples of the organic cation include an ammonium ion, a quaternary ammonium ion, and a pyridinium ion.

M above is preferably a hydrogen atom or an alkali metal ion, more preferably a hydrogen atom, $Li^+$, $Na^+$, or $K^+$, and particularly preferably $K^+$.

The compound of the present invention preferably has at least one aromatic ring per molecule in order to further improve solubility in an organic solvent.

$R^1$ and $R^2$ in Formula (1) may be identical to or different from each other, but are preferably identical to each other from the viewpoint of ease of synthesis.

$R^1$ and $R^2$ in Formula (1) are each preferably a group having 5 or more carbons. $R^1$ and $R^2$ in Formula (1) are each preferably a group having an aromatic ring and/or an ether bond.

The compound of the present invention is soluble in various organic solvents, and compared with sulfonic acid polyol compounds other than the compound of the present invention, has excellent solubility in organic solvents, and has particularly excellent solubility in ketone-based solvents.

Examples of the organic solvents include alcohol solvents such as methanol, ethanol, propanol, isopropanol, and butanol, nitrile-based solvents such as acetonitrile, ketone-based solvents such as acetone, methyl ethyl ketone, methyl isobutyl ketone, diisobutyl ketone, cyclohexanone, and isophorone, ester-based solvents such as methyl acetate, ethyl acetate, and ethyl lactate, ether-based solvents such as dioxane and tetrahydrofuran, aromatic-based solvents such as toluene and xylene, sulfoxide solvents such as dimethylsulfoxide, methylene chloride, chloroform, and cyclohexane.

Among them, ketone-based and aromatic-based solvents are preferable, toluene, methyl ethyl ketone, and cyclohexanone are more preferable, and cyclohexanone is yet more preferable.

With regard to the solubility of the compound of the present invention in cyclohexanone, it is preferable that at least 10 parts by weight dissolves in 100 parts by weight of cyclohexanone at 40° C., it is more preferable that at least 20 parts by weight dissolves, and it is yet more preferable that at least 40 parts by weight dissolves.

A method for synthesizing the compound of the present invention is not particularly limited, but the method shown below may be cited as a particularly preferred example.

A base is made to act on an aminoalkanesulfonic acid or a salt thereof, or an aminoarenesulfonic acid or a salt thereof in water. Subsequently, an epoxy compound is added to the water and a reaction is carried out, thus giving the compound of the present invention. Since the sulfonic acid salt and the epoxide compound react substantially stoichiometrically, by concentrating the aqueous solution to dryness a high purity sulfonic acid compound can be obtained. Furthermore, isolation may be carried out by a known method, and the purity may be increased by carrying out liquid-liquid extraction.

Furthermore, a sulfonic acid salt compound thus obtained may be subjected to a salt exchange reaction by a known method to give another sulfonic acid salt compound, or a salt may be removed by a known method to give a sulfonic acid compound.

The base is not particularly limited; it may be selected according to a desired salt compound, and a hydroxide of an alkali metal is preferable.

The epoxy compound is not particularly limited and may be selected according to a desired compound.

As the compound of the present invention, compounds represented by Formula (2) below and/or Formula (3) below are preferable.

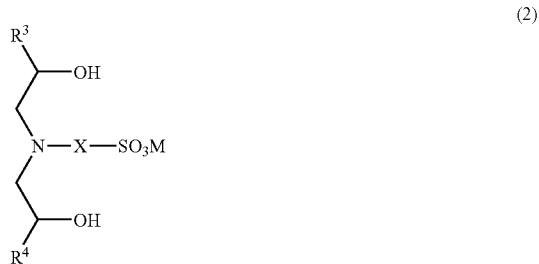

(2)

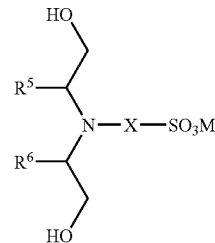

(3)

(In Formula (2) and Formula (3), X denotes a divalent linking group, $R^3$, $R^4$, $R^5$, and $R^6$ independently denote an alkyl group having 2 to 20 carbons, an aryl group having 6 to 20 carbons, an aralkyl group having 7 to 20 carbons, an alkoxyalkyl group having 2 to 20 carbons, or an aryloxyalkyl group having 7 to 20 carbons, and M denotes a hydrogen atom or a cation.)

X and M in Formula (2) and Formula (3) have the same meanings as those of X and M in Formula (1), and a preferred range is also the same.

$R^3$, $R^4$, $R^5$ and $R^6$ in Formula (2) and Formula (3) independently denote an alkyl group having 2 to 20 carbons, an aryl group having 6 to 20 carbons, an aralkyl group having 7 to 20 carbons, an alkoxyalkyl group having 2 to 20 carbons, or an aryloxyalkyl group having 7 to 20 carbons.

The number of carbons in the alkyl group denoted by $R^3$, $R^4$, $R^5$ and $R^6$ is 2 to 20, preferably 2 to 8, and more preferably 2 to 4.

The number of carbons in the aryl group denoted by $R^3$, $R^4$, $R^5$ and $R^6$ is 6 to 20, preferably 6 to 10, and more preferably 6.

The number of carbons in the aralkyl group denoted by $R^3$, $R^4$, $R^5$ and $R^6$ is 7 to 20, and preferably 7 to 11.

The number of carbons in the alkoxyalkyl group denoted by $R^3$, $R^4$, $R^5$ and $R^6$ is 2 to 20, preferably 2 to 12, and more preferably 2 to 5.

The number of carbons in the aryloxyalkyl group denoted by $R^3$, $R^4$, $R^5$ and $R^6$ is 7 to 20, preferably 7 to 12, and more preferably 7.

Examples of a substituent that the alkyl group, aryl group, aralkyl group, alkoxyalkyl group, or aryloxyalkyl group denoted by $R^3$, $R^4$, $R^5$ and $R^6$ may have include a halogen atom (a fluorine atom, a chlorine atom, a bromine atom, an iodine atom), a hydroxy group, a sulfonyl group, and a silyl group.

Furthermore, the alkyl group and the aralkyl group may be straight chain or branched.

Among them, preferred examples of $R^3$ and $R^4$ include an ethyl group, a methoxymethyl group, a butoxymethyl group, a phenoxymethyl group, and a phenyl group, and more preferred examples thereof include a methoxymethyl group, a butoxymethyl group, a phenoxymethyl group, and a phenyl group.

Furthermore, preferred examples of $R^5$ and $R^6$ include an ethyl group, a methoxymethyl group, a butoxymethyl group, a phenoxymethyl group, and a phenyl group, and more preferred examples thereof include a methoxymethyl group, a butoxymethyl group, a phenoxymethyl group, and a phenyl group.

Specific preferred examples of the compound of the present invention include (S-1) to (S-70) shown below, but the compound of the present invention is not limited thereto. In the specific examples below, Ph denotes a phenyl group, and Et denotes an ethyl group.
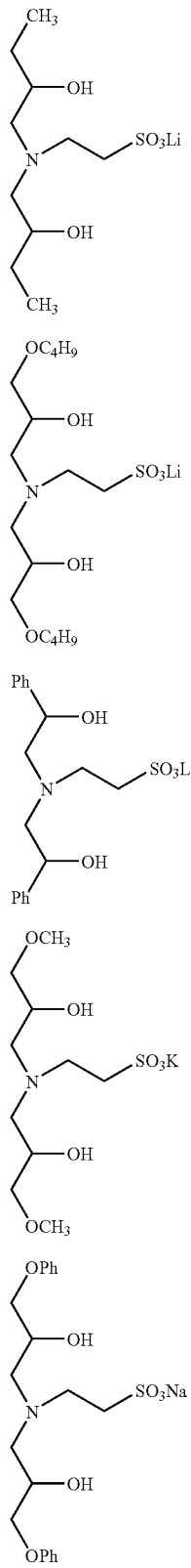
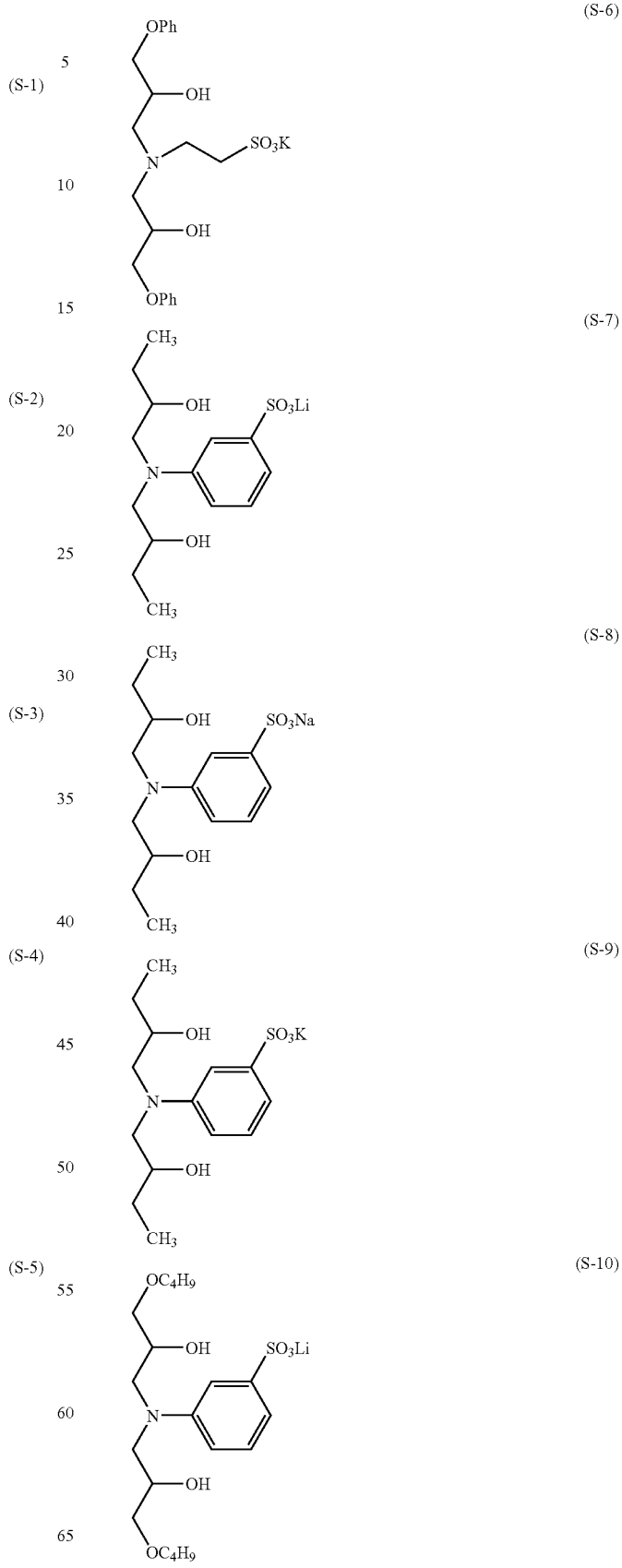

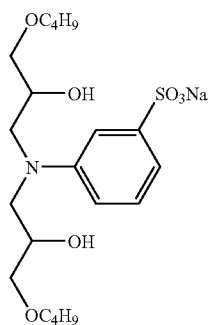
(S-11)
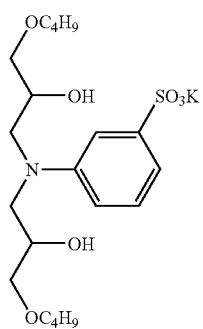
(S-12)
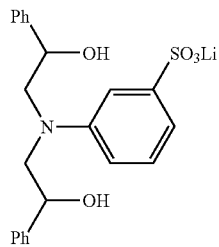
(S-13)
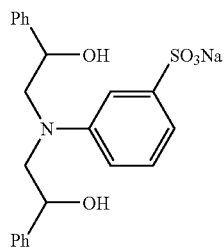
(S-14)
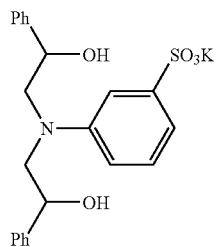
(S-15)
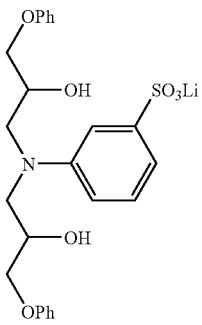
(S-16)
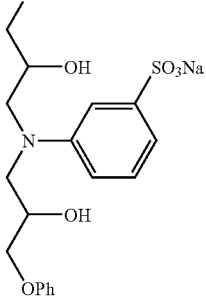
(S-17)
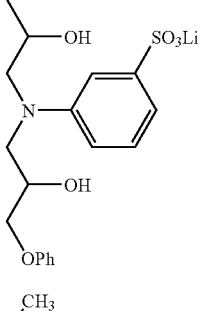
(S-18)
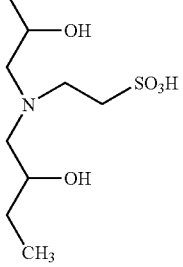
(S-19)
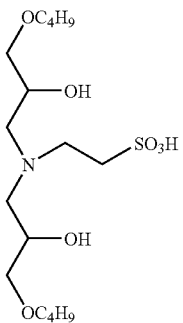
(S-20)

(S-21) 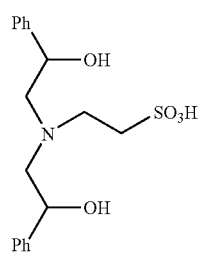
(S-22) 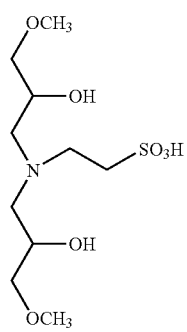
(S-23) 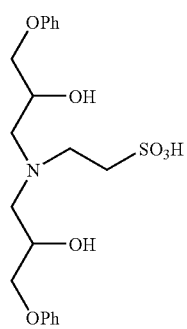
(S-24) 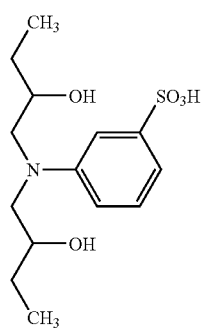
(S-25) 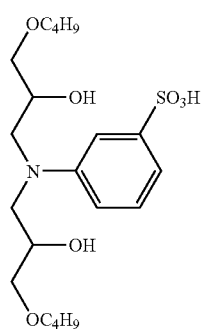
(S-26) 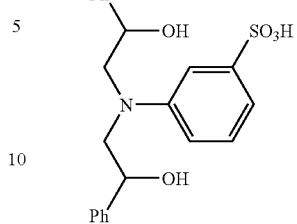
(S-27) 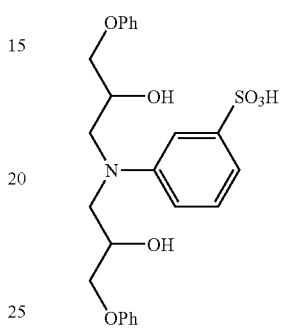
(S-28) 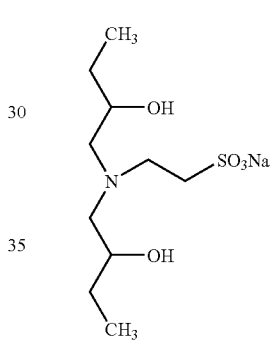
(S-29) 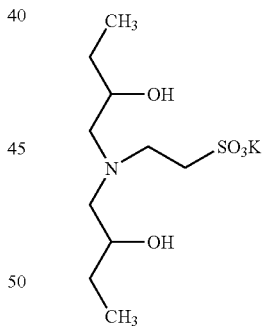
(S-30) 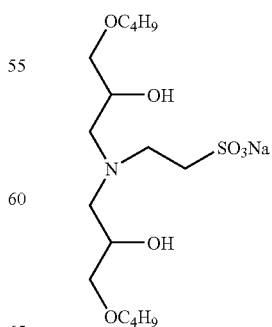

-continued
(S-31) 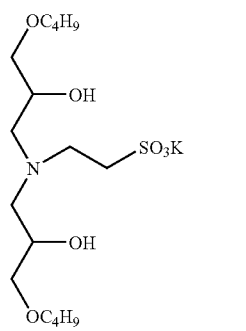
(S-32) 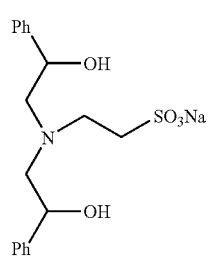
(S-33) 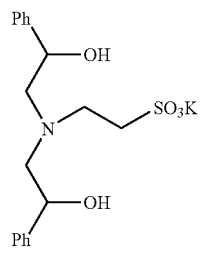
(S-34) 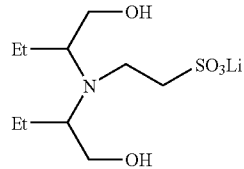
(S-35) 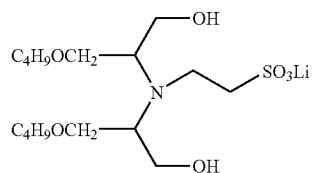
(S-36) 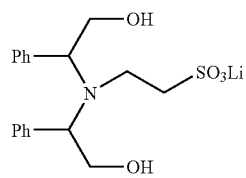
(S-37) 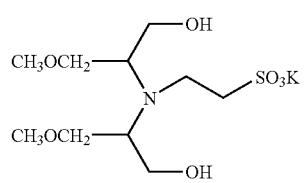
-continued
(S-38) 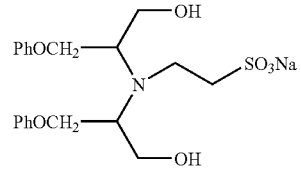
(S-39) 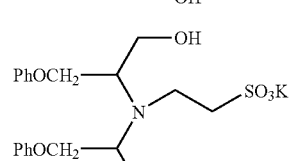
(S-40) 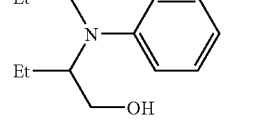
(S-41) 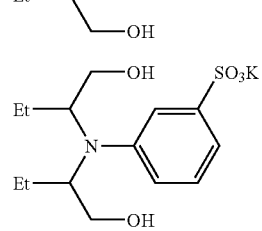
(S-42) 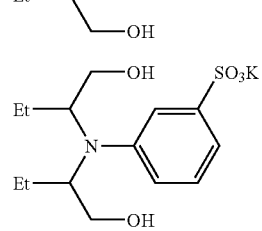
(S-43) 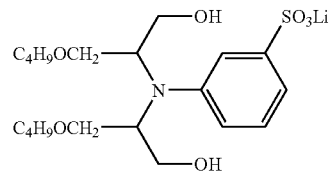
(S-44) 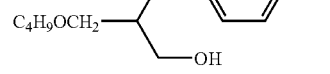
(S-45) 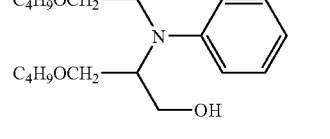
(S-46) 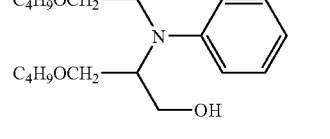

-continued
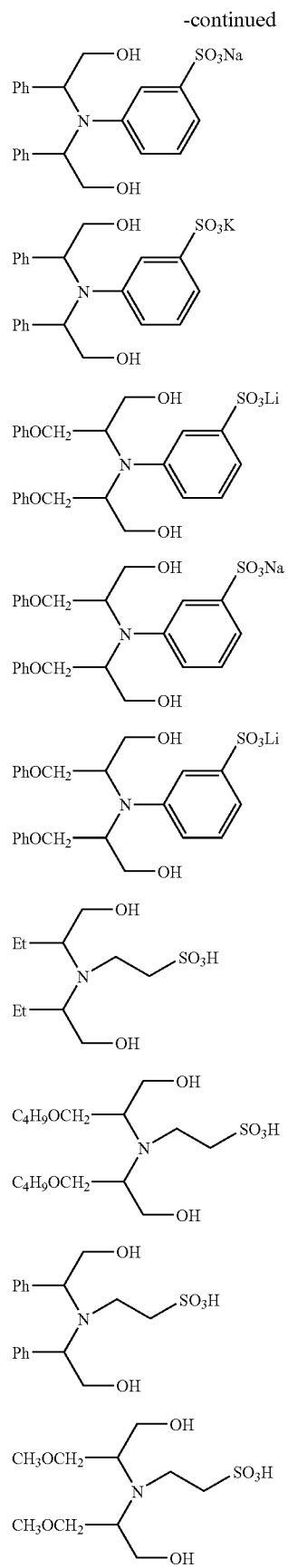
(S-47)
(S-48)
(S-49)
(S-50)
(S-51)
(S-52)
(S-53)
(S-54)
(S-55)
-continued
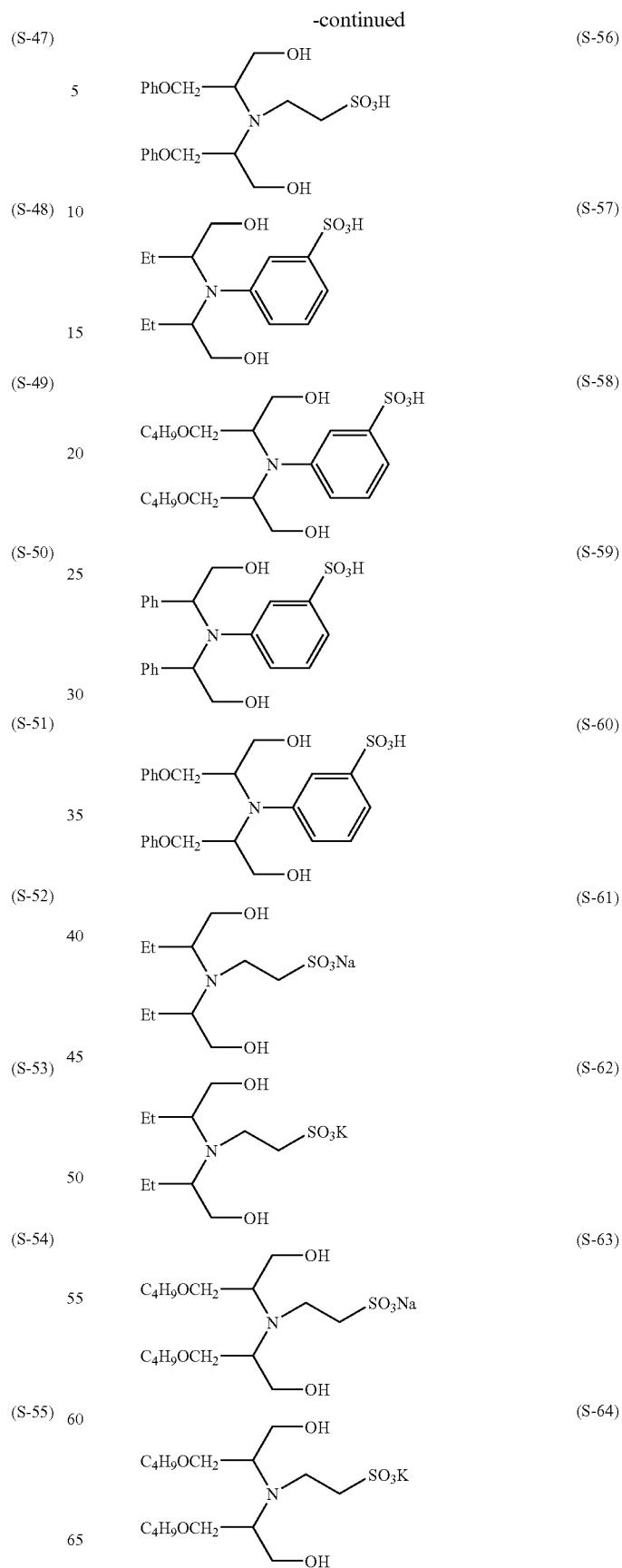
(S-56)
(S-57)
(S-58)
(S-59)
(S-60)
(S-61)
(S-62)
(S-63)
(S-64)

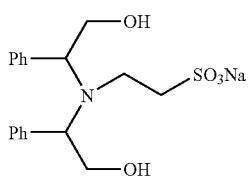
(S-65)

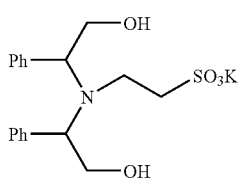
(S-66)

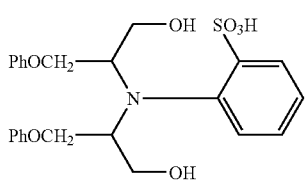
(S-67)

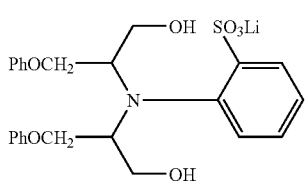
(S-68)

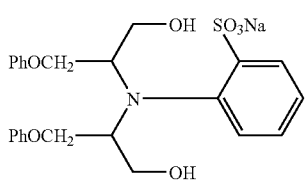
(S-69)

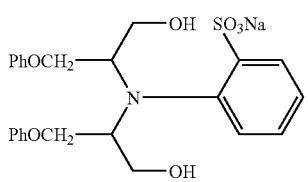
(S-70)

In the present invention, it is also preferable to use a mixture of a compound represented by Formula (2) and a compound represented by Formula (3) at any ratio. Compared with a case in which a compound represented by Formula (2) or Formula (3) is used on its own, when compounds represented by Formula (2) and Formula (3) are mixed, the solubility in a solvent such as cyclohexane improves in some cases.

Preferred synthetic conditions for a compound represented by Formula (2) involve reacting an epoxide with the lithium salt of taurine or benzenesulfonic acid in water at 25° C. to 50° C. On the other hand, in the case of a compound represented by Formula (3), an epoxide is reacted with the potassium salt of taurine or benzenesulfonic acid in water at 25° C. to 50° C.

The pH in the synthesis is preferably 6 to 10, and more preferably 7 to 9.

Depending on the reaction conditions, a mixture of a compound represented by Formula (2) and a compound represented by Formula (3) can be obtained.

(2) Polyurethane Resin

The polyurethane resin of the present invention is a polyurethane resin obtained by polymerization of a polyol and a polyisocyanate, and as the polyol at least a compound represented by Formula (1) is used.

The 'polyol' referred to in the present invention is a compound or a group of compounds having two or more hydroxy groups per molecule. The polyol may comprise one type of compound or may comprise two or more types in combination at any ratio.

As described in JP-A-9-138939 above, particularly when it is used as a binder of a magnetic recording medium, it is generally known that a carboxylic acid, a sulfonic acid, a metal salt thereof, etc., which are adsorbing functional groups for adsorbing on a magnetic substance, may be introduced into the polyurethane resin. Since the dispersion properties and the mechanical strength of a coating are improved by increasing the amount of adsorbing functional group in the polyurethane resin, conventionally an effect has been exhibited to some extent by introducing a sulfonic acid (salt) group, which is a relatively strong polar group.

The use of a glycol or polyol having an adsorbing functional group enables such an adsorbing functional group to be introduced, but a glycol, etc. having a strong polar group such as a sulfonic acid (salt) group is difficult to dissolve in a solvent generally used as a polymerization solvent for a polyurethane resin, such as methyl ethyl ketone (MEK) or cyclohexane. Therefore, a glycol having a sulfonic acid (salt) group is incorporated into a polyester in advance, and when polymerizing to give the polyurethane the polyester polyol having a sulfonic acid (salt) group is used as a polymerization component, thus dissolving it in the polyurethane polymerization solvent and producing the polyurethane resin.

Such a polyester polyol having a sulfonic acid (salt) group is formed by an esterification reaction between a glycol and a metal sulfonate-containing aromatic dicarboxylic acid, such as sodium 5-sulfoisophthalic acid, potassium 5-sulfoisophthalic acid, or sodium sulfoterephthalic acid, that is insoluble in a polymerization solvent such as methyl ethyl ketone (MEK) or cyclohexane. In this esterification reaction, formation of an oligomer component due to repeated reaction between the dicarboxylic acid and the glycol as shown below cannot be avoided, and as a result several metal sulfonate groups are contained in one oligomer molecule.

The reaction between the glycol (A) and the metal sulfonate-containing aromatic dicarboxylic acid (B) is explained here as an example. The glycol (A) and the metal sulfonate-containing aromatic dicarboxylic acid (B) are represented by Formula (A) and Formula (B) respectively.

Glycol: HO—R$^1$—OH (A)

Metal sulfonate-containing aromatic dicarboxylic acid: HOCO—R$^2$—COOH (B)

(R$^2$ has a metal sulfonate-containing aromatic ring.)

The reaction product from two glycol (A) molecules and one metal sulfonate-containing aromatic dicarboxylic acid (B) molecule is as follows.

HO—R$^1$—OCO—R$^2$—COO—R$^1$—OH (C)

The reaction product from one (C) molecule and two (B) molecules is as follows.

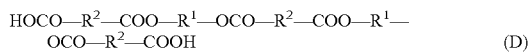

(D)

Such a polyester polyol exists in a nonuniform form in which the sulfonic acid (salt) group, which is an adsorbing functional group, is localized on some of the oligomer components. This polyester polyol dissolves in methyl ethyl ketone (MEK), cyclohexane, etc. which are polymerization solvents, during a reaction to form a polyurethane, and even if a reaction to form a polyurethane is carried out uniformly with another glycol starting material, it inevitably gives a non-uniform form in which a sulfonic acid (salt) group, which is an adsorbing functional group, is localized on some of the oligomer components. Since the sulfonic acid (salt) group is present nonuniformly in the polyurethane, a component that has no sulfonic acid (salt) group at all is present in the polyurethane so formed. It has been found that such a component having no adsorbing functional group does not exhibit a dispersion function by adsorption onto a magnetic substance, and thus degrades the dispersion properties of a microparticulate ferromagnetic powder and a non-magnetic lower layer powder (non-magnetic powder) used in recent high density media, and a polyurethane component that cannot adsorb migrates to the surface of the medium in the process of coating and drying, thus causing the durability of the medium to degrade.

Conventionally, in order to solve this problem, JP-A-5-70545 describes a case in which a sulfonic acid (salt) group-containing diol that does not require solvent solubility being imparted thereto by polyesterification has been examined, but the solvent solubility is not sufficient. As a result, sufficient dispersion properties cannot be obtained.

As described above, a polyurethane resin used as a binder for a magnetic recording medium is required to have an adsorbing functional group such as a sulfonic acid (salt) group introduced in order to improve adsorption onto a ferromagnetic powder and/or a non-magnetic powder. As in conventional cases, when a sulfonic acid (salt) group is introduced into a polyester polyol, etc., there are various problems due to the non-uniform presence of the sulfonic acid (salt) group in the polyurethane.

On the other hand, a low molecular weight glycol or polyol having such an adsorbing functional group has low solubility in a solvent (e.g. MEK, cyclohexanone, etc.) used in polyurethane polymerization, and is difficult to use.

The present inventors have found as a result of synthesizing various types of diols in which an epoxy group-containing compound is added to a sulfonic acid (salt) group-containing amine compound such as taurine that it is possible to guarantee solvent solubility by introducing a branch in the vicinity of a nitrogen atom of a tertiary amine; introduction directly into a polyurethane resin is possible, and the above-mentioned problems have thus been solved.

That is, a compound represented by Formula (1) has high solubility in a solvent used in polyurethane polymerization even though it has a sulfonic acid (salt) group, and since a sulfonic acid (salt) group-containing diol dissolves in a polyurethane polymerization solvent as a monomer, it is possible to introduce a sulfonic acid (salt) group uniformly into a polyurethane, and it is possible to reduce a component having no sulfonic acid (salt) group at all compared with a case in which a polyester diol is used.

Furthermore, a polyurethane resin obtained by polymerization using a compound represented by Formula (1) gives a high degree of dispersion of a magnetic substance and/or a non-magnetic powder, and a resultant coating has excellent smoothness. As a result, a magnetic recording medium having excellent electromagnetic conversion characteristics is obtained.

The polyurethane resin of the present invention uses as a chain-extending agent a low-molecular-weight diol having an —$SO_3M$ group, and unlike conventional methods can be obtained directly by polymerization without introducing an —$SO_3M$ group into a polyester polyol or polyether polyol.

The polyurethane resin of the present invention is obtained by polymerizing a polyol and a polyisocyanate; it is preferable to use as the polyol a short chain diol having a weight-average molecular weight of no greater than 500 and another polyol, and it is more preferable to use as the short chain diol a compound represented by Formula (1) above. It is yet more preferable to use a compound represented by Formula (2) and/or Formula (3).

Other Polyol

It is preferable to use a compound represented by Formula (1) above and another polyol in combination.

The polyol used in combination is not particularly limited, and a known polyol such as a polyester polyol, a polyether polyol, a polyether ester polyol, a polycarbonate polyol, a polyolefin polyol, or a dimer diol may be used as necessary.

Among them, a polyester polyol and a polyether polyol are preferable.

The polyester polyol is obtained by polycondensation of a polycarboxylic acid (polybasic acid) and a polyol, and is preferably one obtained by a reaction between a dibasic acid (dicarboxylic acid) and a diol. A dibasic acid component that can be used in the polyester polyol is not particularly limited, and adipic acid, azelaic acid, phthalic acid, and Na sulfoisophthalic acid are preferable. As the diol, one having a branched side chain such as 2,2-dimethyl-1,3-propanediol, 2-ethyl-2-butyl-1,3-propanediol, or 3-methyl-1,5-pentanediol is preferable.

The polyether polyol is preferably one having a cyclic structure such as bisphenol A polypropylene oxide adduct or bisphenol A polyethylene oxide adduct.

Chain-Extending Agent

In addition to the polyol, a known short chain diol having a molecular weight of on the order of 200 to 500 may be used as a chain-extending agent as necessary. Among them, an aliphatic diol having a branched side chain with 2 or more carbons, an ether compound having a cyclic structure, a short chain diol having a bridged hydrocarbon structure, and a short chain diol having a spiro structure are preferable.

Furthermore, in order to impart radiation curability, a diol having at least one acrylic double bond per molecule may be used in combination. The acrylic double bond referred to here means an acrylic acid, acrylic acid ester, acrylamide, methacrylic acid, methacrylic acid ester, methacrylamide, etc. residue (acryloyl group or methacryloyl group). Among them, a diol having one or more (meth)acryloyloxy groups is preferable, and a diol having one or more acryloyloxy groups is more preferable.

As the aliphatic diol having a branched side chain with 2 or more carbons, those below can be cited.

2-Methyl-2-ethyl-1,3-propanediol, 3-methyl-3-ethyl-1,5-pentanediol, 2-methyl-2-propyl-1,3-propanediol, 3-methyl-3-propyl-1,5-pentanediol, 2-methyl-2-butyl-1,3-propanediol, 3-methyl-3-butyl-1,5-pentanediol, 2,2-diethyl-1,3-propanediol, 3,3-diethyl-1,5-pentanediol, 2-ethyl-2-butyl-1,3-propanediol, 3-ethyl-3-butyl-1,5-pentanediol, 2-ethyl-2-propyl-1,3-propanediol, 3-ethyl-3-propyl-1,5-pentanediol, 2,2-dibutyl-1,3-propanediol, 3,3-dibutyl-1,5-pentanediol, 2,2-dipropyl-1,3-propanediol, 3,3-dipropyl-1,5-pentanediol, 2-butyl-2-propyl-1,3-propanediol, 3-butyl-3-propyl-1,5-pentanediol, 2-ethyl-1,3-propanediol, 2-propyl-1,3-propanediol, 2-butyl-1,3-propanediol, 3-ethyl-1,5-pentanediol, 3-propyl-1,5-pentanediol, 3-butyl-1,5-pentanediol, 3-octyl-1,5-pentanediol, 3-myristyl-1,5-pentanediol, 3-stearyl-1,5-pentanediol, 2-ethyl-1,6-hexanediol, 2-propyl-1,6-hexanediol, 2-butyl-1,6-hexanediol, 5-ethyl-1,9-nonanediol, 5-propyl-1,9-nonanediol, 5-butyl-1,9-nonanediol, etc.

Among them, 2-ethyl-2-butyl-1,3-propanediol and 2,2-diethyl-1,3-propanediol are preferable.

Examples of the ether compound having a cyclic structure include bisphenol A ethylene oxide adduct, bisphenol A propylene oxide adduct, hydrogenated bisphenol A ethylene oxide adduct, and hydrogenated bisphenol A propylene oxide adduct.

With regard to the bridged hydrocarbon structure or the spiro structure, it is preferably at least one structure selected from the group consisting of Formulae (1) to (3).

(1)

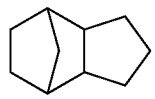

(2)

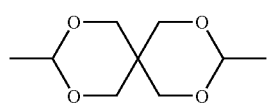

(3)

Specific examples of the short chain diol having a bridged hydrocarbon structure include bicyclo[1.1.0]butanediol, bicyclo[1.1.1]pentanediol, bicyclo[2.1.0]pentanediol, bicyclo[2.1.1]hexanediol, bicyclo[3.1.0]hexanediol, bicyclo[2.2.1]heptanediol, bicyclo[3.2.0]heptanediol, bicyclo[3.1.1]heptanediol, bicyclo[2.2.2]octanediol, bicyclo[3.2.1]octanediol, bicyclo[4.2.0]octanediol, bicyclo[5.2.03]nonanediol, bicyclo[3.3.1]nonanediol, bicyclo[3.3.2]decanediol, bicyclo[4.2.2]decanediol, bicyclo[4.3.3]dodecanediol, bicyclo[3.3.3]undecanediol, bicyclo[1.1.0]butanedimethanol, bicyclo[1.1.1]pentanedimethanol, bicyclo[2.1.0]pentanedimethanol, bicyclo[2.1.1]hexanedimethanol, bicyclo[3.1.0]hexanedimethanol, bicyclo[2.2.1]heptanedimethanol, bicyclo[3.2.0]heptanedimethanol, bicyclo[3.1.1]heptanedimethanol, bicyclo[2.2.2]octanedimethanol, bicyclo[3.2.1]octanedimethanol, bicyclo[4.2.0]octanedimethanol, bicyclo[5.2.0]nonanedimethanol, bicyclo[3.3.1]nonanedimethanol, bicyclo[3.3.2]decanedimethanol, bicyclo[4.2.2]decanedimethanol, bicyclo[4.3.3]dodecanedimethanol, bicyclo[3.3.3]undecanedimethanol, tricyclo[2.2.1.0]heptanediol, tricyclo[5.2.1.0$^{2,6}$]decanediol, tricyclo[4.2.1.2$^{7,9}$]undecanediol, tricyclo[5.4.0.0$^{2,9}$]undecanediol, tricyclo[5.3.1.1]dodecanediol, tricyclo[4.4.1.1]dodecanediol, tricyclo[7.3.2.0$^{5,13}$]tetradecanediol, tricyclo[5.5.1.0$^{3,11}$]tridecanediol, tricyclo[2.2.1.0]heptanedimethanol, tricyclo[5.2.1.0$^{2,6}$]decanedimethanol, tricyclo[4.2.1.2$^{7,9}$]undecanedimethanol, tricyclo[5.4.0.0$^{2,9}$]undecanedimethanol, tricyclo[5.3.1.1]dodecanedimethanol, tricyclo[4.4.1.1]dodecanedimethanol, tricyclo[7.3.2.0$^{5,13}$]tetradecanedimethanol, and tricyclo[5.5.1.0$^{3,11}$]tridecanedimethanol.

Among them, tricyclo[5.2.1.0$^{2,6}$]decanedimethanol is preferable.

Specific examples of the short chain diol having a spiro structure include spiro[3.4]octanedimethanol, spiro[3.4]heptanedimethanol, spiro[3.4]decanedimethanol, dispiro[5.1.7.2]heptadecanedimethanol, cyclopentane spirocyclobutanedimethanol, cyclohexane spirocyclopentanedimethanol, spirobicyclohexanedimethanol, and bis(1,1-dimethyl-2-hydroxyethyl)-2,4,8,10-tetraoxaspiro[5.5]undecane. Bis(1,1-dimethyl-2-hydroxyethyl)-2,4,8,10-tetraoxaspiro[5.5]undecane is preferable.

Specific examples of the diol having at least one acrylic double bond per molecule include glycerol monoacrylate, glycerol monomethacrylate (BLEMMER GLM, NOF Corporation), and bisphenol A epoxy acrylate (Epoxy Ester 3000A, KYOEISHA CHEMICAL Co., Ltd.).

Polyisocyanate

In the present invention, as the polyisocyanate a diisocyanate may suitably be used.

The diisocyanate is not particularly limited, and a known diisocyanate is used. Specifically, TDI (tolylene diisocyanate), MDI (diphenylmethane diisocyanate), p-phenylene diisocyanate, o-phenylene diisocyanate, m-phenylene diisocyanate, xylylene diisocyanate, hydrogenated xylylene diisocyanate, isophorone diisocyanate, etc. are preferable.

The polyurethane resin used in the present invention may be produced by polymerization (addition polymerization), in the presence of a catalyst, of a compound represented by Formula (1) above, another polyol, a polyisocyanate, and as necessary a chain-extending agent.

As the catalyst a known polymerization catalyst for a polyurethane resin may be used, and examples thereof include a tertiary amine catalyst and an organotin catalyst. Examples of the tertiary amine catalyst include diethylenetriamine, N-methylmorpholine, and tetramethylhexamethylenediamine, and examples of the organotin catalyst include dibutyltin dilaurate and tin octoate. In the present invention, it is preferable to use an organotin catalyst as the catalyst.

The amount of catalyst added, relative to the total weight of polymerization components used in the polymerization, including the compound represented by Formula (1), the other polyol, the polyisocyanate, and as necessary the other chain-extending agent, is 0.01 to 5 parts by weight, preferably 0.01 to 1 parts by weight, and more preferably 0.01 to 0.1 parts by weight.

Furthermore, it is preferable to carry out polymerization by dissolving the compound represented by Formula (1), the polyol, and the polyisocyanate in a solvent (polymerization solvent) and carrying out heating, pressurizing, flushing with nitrogen, etc. as necessary. As the solvent used here, it may be selected from known solvents used in the synthesis of a polyurethane resin, and examples thereof include ketone-based solvents such as acetone, methyl ethyl ketone, and cyclohexanone, ester-based solvents such as methyl acetate, ethyl acetate, and ethyl lactate, ether-based solvents such as dioxane and tetrahydrofuran, aromatic-based solvents such as toluene and xylene, amide-based solvents such as N,N-dimethylformamide, N,N-dimethylacetamide, and N-methylpyrrolidone, and sulfoxide solvents such as dimethylsulfoxide, methylene chloride, chloroform, and cyclohexane. Among them, methyl ethyl ketone and cyclohexanone are suitably used.

Weight-Average Molecular Weight

The polyurethane resin of the present invention preferably has a weight-average molecular weight of at least 10,000 but no greater than 200,000 (in the present invention, 'at least 10,000 but no greater than 200,000' is also referred to as '10,000 to 200,000', the same applies below), more preferably 40,000 to 100,000, and yet more preferably 50,000 to 90,000. It is preferable for the polyurethane resin of the present invention to have a weight-average molecular weight of at least 10,000 since good storage properties are obtained. It is also preferable for it to be no greater than 200,000 since good dispersion properties are obtained.

As methods for controlling the weight-average molecular weight so that it is in the above-mentioned range, those below can be cited.

For example, the weight-average molecular weight may be adjusted by finely adjusting the molar ratio of glycol-derived OH group to diisocyanate-derived NCO group or by using a reaction catalyst.

Examples of the reaction catalyst include an organometallic compound such as dibutyltin dilaurate, a tertiary amine such as triethylamine or triethylenediamine, and a metal salt such as potassium acetate or zinc stearate. Preferred examples thereof include dibutyltin dilaurate.

As other methods, the weight-average molecular weight may be adjusted by adjusting the solids concentration, the reaction temperature, the reaction solvent, the reaction time, etc. during a reaction.

Molecular Weight Distribution

The polyurethane resin of the present invention preferably has a molecular weight distribution (Mw/Mn) of 1.0 to 2.5, and more preferably 1.5 to 2.0. It is preferable for the molecular weight distribution to be no greater than 2.5 since the compositional distribution is small and good dispersion properties are obtained.

Urethane Group Concentration

The polyurethane resin of the present invention preferably has a urethane, group concentration of 2.5 mmol/g to 4.5 mmol/g, and more preferably 3.0 mmol/g to 4.0 mmol/g.

It is preferable for the urethane group concentration to be at least 2.5 mmol/g since the Tg of a coating does not decrease, and good durability can be obtained. Furthermore, it is preferable for it to be no greater than 4.5 mmol/g since good solvent solubility is obtained and the dispersion properties are good, thus enabling the polyol content to be adjusted and the molecular weight to be easily controlled.

Glass Transition Temperature

The polyurethane resin used in the present invention, when it does not have radiation curability, preferably has a glass transition temperature (Tg) of 80° C. to 200° C., and more preferably 90° C. to 160° C.

It is preferable for the glass transition temperature to be at least 80° C. since good coating strength is obtained and the durability and storage properties improve. Furthermore, it is preferable for it to be no greater than 200° C. since the calender molding characteristics and the electromagnetic conversion characteristics are good.

Moreover, the glass transition temperature (Tg) of a polyurethane resin having radiation curability is preferably 10° C. to 160° C., and more preferably 10° C. to 100° C. It is preferable for the glass transition temperature to be at least 10° C. since good coating strength is obtained after curing with radiation, and the durability and storage properties improve. It is also preferable for it to be no greater than 160° C. since the calender molding characteristics are good even when calendering is carried out after curing with radiation, and the electromagnetic conversion characteristics are good.

Polar Group in Polyurethane Resin

Since the polyurethane resin of the present invention is obtained by using a compound represented by Formula (1) as a polyol, it has —$SO_3M$ as a polar group. Here, M is a hydrogen atom, an alkali metal, or an alkaline earth metal.

In the present invention, M is preferably an alkali metal, and more preferably $K^+$. That is, the polyurethane resin of the present invention has —$SO_3M$ as a polar group.

The polar group content is preferably $1\times10^{-5}$ eq/g to $2\times10^{-3}$ eq/g, more preferably $1\times10^5$ eq/g to $1\times10^{-3}$ eq/g, and yet more preferably $1\times10^{-5}$ eq/g to $5\times10^{-4}$ eq/g.

It is preferable for the polar group content to be at least $1\times10^{-5}$ since sufficient adsorption power toward a magnetic substance can be obtained and the dispersion properties are good. Furthermore, it is preferable for it to be no greater than $2\times10^{-3}$ eq/g since good solubility in a solvent is obtained.

The polyurethane resin of the present invention may have another polar group.

As said other polar group, —$OSO_3M$, —$PO_3M_2$, and —COOM are preferable. Among them, —$OSO_3M$ is more preferable. M denotes a hydrogen atom or a monovalent cation. Examples of the monovalent cation include an alkali metal and ammonium.

Hydroxy Group in Polyurethane Resin

The polyurethane resin used in the present invention may comprise a hydroxy group (OH group). The number of OH groups per molecule is preferably 2 to 20, and more preferably 3 to 15. When the number of OH groups is in the above-mentioned range, since reactivity with an isocyanate curing agent improves, the coating strength and durability improve, and since solubility in a solvent improves, the dispersion properties are good.

Acrylic Double Bond in Polyurethane Resin

Using a diol having at least one acrylic double bond per molecule enables an acrylic double bond to be introduced into the polyurethane resin of the present invention.

The double bond (ethylenically unsaturated bond) content is preferably $1\times10^{-5}$ eq/g to $2\times10^{-3}$ eq/g, more preferably $1\times10^{-5}$ eq/g to $1\times10^{-3}$ eq/g, and yet more preferably $1\times10^{-4}$ eq/g to $1\times10^{-3}$ eq/g.

It is preferable for the double bond content to be at least $1\times10^{-5}$ eq/g since a coating having good strength is obtained after curing with radiation. It is also preferable for it to be no greater than $2\times10^{-3}$ eq/g since the calender molding characteristics are good even when calendering is carried out after curing with radiation, and the electromagnetic conversion characteristics are good.

Magnetic Recording Medium

The magnetic recording medium of the present invention comprises, above a non-magnetic support, at least one magnetic layer having a ferromagnetic powder dispersed in a binder. Furthermore, the magnetic recording medium of the present invention preferably has, in order above the non-magnetic support, a non-magnetic layer having a non-magnetic powder dispersed in a binder and a magnetic layer. The magnetic recording medium of the present invention comprises the polyurethane resin of the present invention as a binder for the magnetic layer and/or the non-magnetic layer, and preferably comprises the polyurethane resin of the present invention as a binder for the magnetic layer and the non-magnetic layer.

I. Magnetic Layer

Binder

In the present invention, in addition to the above-mentioned polyurethane resin of the present invention, another binder can be used.

Examples of said other binder include a polyurethane resin other than the polyurethane resin of the present invention, a polyester resin, a polyamide resin, a vinyl chloride resin, an acrylic resin obtained by copolymerization of styrene, acrylonitrile, methyl methacrylate, etc., a cellulose resin such as nitrocellulose, an epoxy resin, a phenoxy resin, and a polyvinyl alkylal resin such as polyvinyl acetal or polyvinyl butyral, and they can be used singly or in a combination of two or more types. Among these, the polyurethane resin, the acrylic resin, the cellulose resin, and the vinyl chloride resin are preferable.

In order to improve the dispersibility of the magnetic powder and the non-magnetic powder, the binder used in combination preferably has a functional group (polar group) that is adsorbed on the surface of the powders. Preferred examples of the functional group include —$SO_3M$, —$SO_4M$, —PO$(OM)_2$, —OPO$(OM)_2$, —COOM, >$NSO_3M$, >$NRSO_3M$, —$NR^1R^2$, and —$N^+R^1R^2R^3X^-$. M denotes a hydrogen atom or an alkali metal such as Na or K, R denotes an alkylene group, $R^1$, $R^2$, and $R^3$ denote alkyl groups, hydroxyalkyl groups, or hydrogen atoms, and X denotes a halogen such as Cl or Br. The amount of functional group in the binder is preferably 10 to 200 μeq/g, and more preferably 30 to 120 μeq/g. It is preferable if the amount of functional group in the binder is in this range since good dispersibility can be achieved.

It is preferable to impart to the binder used in combination, in addition to an adsorbing functional group, a functional group such as an —OH group having an active hydrogen in order to improve coating strength by forming a crosslinked structure after a reaction with an isocyanate curing agent. The polar group content is preferably $1 \times 10^{-5}$ eq/g to $2 \times 10^{-3}$ eq/g, more preferably $1 \times 10^{-5}$ eq/g to $1 \times 10^{-3}$ eq/g, and yet more preferably $1 \times 10^{-5}$ eq/g to $5 \times 10^4$ eq/g. It is preferable for the polar group content to be at least $1 \times 10^{-5}$ since sufficient adsorption power toward a magnetic substance can be obtained and the dispersion properties are good. It is also preferable for it to be no greater than $2 \times 10^{-3}$ eq/g since good solubility in a solvent is obtained.

With regard to the molecular weight of the binder, the weight-average molecular weight is preferably at least 10,000 but no greater than 200,000, and more preferably at least 20,000 but no greater than 100,000. It is preferable for it to be in this range since the coating strength is sufficient, the durability is good, and the dispersion properties improve.

The polyurethane resin used in combination, which is a preferred binder, is described in detail in, for example, 'Poriuretan Jushi Handobukku' (Polyurethane Resin Handbook) (Ed., K. Iwata, 1986, The Nikkan Kogyo Shimbun, Ltd.), and it is normally obtained by addition-polymerization of a long chain diol, a short chain diol (also known as a chain extending agent), and a diisocyanate compound. As the long chain diol, a polyester diol, a polyether diol, a polyetherester diol, a polycarbonate diol, a polyolefin diol, etc, having a molecular weight of 500 to 5,000 are used. Depending on the type of this long chain polyol, the polyurethanes are called polyester urethanes, polyether urethanes, polyetherester urethanes, polycarbonate urethanes, etc.

The polyester diol is obtained by a condensation-polymerization between a glycol and a dibasic aliphatic acid such as adipic acid, sebacic acid, or azelaic acid, or a dibasic aromatic acid such as isophthalic acid, orthophthalic acid, terephthalic acid, or naphthalenedicarboxylic acid. Examples of the glycol component include ethylene glycol, 1,2-propylene glycol, 1,3-propanediol, 1,4-butanediol, 1,5-pentanediol, 3-methyl-1,5-pentanediol, 1,6-hexanediol, 2,2-dimethyl-1,3-propanediol, 1,8-octanediol, 1,9-nonanediol, cyclohexanediol, cyclohexane dimethanol, and hydrogenated bisphenol A. As the polyester diol, in addition to the above, a polycaprolactonediol or a polyvalerolactonediol obtained by ring-opening polymerization of a lactone such as ε-caprolactone or γ-valerolactone can be used.

From the viewpoint of resistance to hydrolysis, the polyester diol is preferably one having a branched side chain or one obtained from an aromatic or alicyclic starting material.

Examples of the polyether diol include polyethylene glycol, polypropylene glycol, polytetramethylene glycol, aromatic glycols such as bisphenol A, bisphenol S, bisphenol P, and hydrogenated bisphenol A, and addition-polymerization products from an alicyclic diol and an alkylene oxide such as ethylene oxide or propylene oxide.

These long chain diols can be used as a mixture of a plurality of types thereof.

The short chain diol can be chosen from the compound group that is cited as the glycol component of the above-mentioned polyester diol. Furthermore, a small amount of a tri- or higher-hydric alcohol such as, for example, trimethylolethane, trimethylolpropane, or pentaerythritol can be added, and this gives a polyurethane resin having a branched structure, thus reducing the solution viscosity and increasing the number of OH end groups of the polyurethane so as to improve the curing properties with the isocyanate curing agent.

Examples of the diisocyanate compound include aromatic diisocyanates such as MDI (diphenylmethane diisocyanate), 2,4-TDI (tolylene diisocyanate), 2,6-TDI, 1,5-NDI (naphthalene diisocyanate), TODI (tolidine diisocyanate), p-phenylene diisocyanate, and XDI (xylylene diisocyanate), and aliphatic and alicyclic diisocyanates such as trans-cyclohexane-1,4-diisocyanate, HDI (hexamethylene diisocyanate), IPDI (isophorone diisocyanate), $H_6XDI$ (hydrogenated xylylene diisocyanate), and $H_{12}MDI$ (hydrogenated diphenylmethane diisocyanate).

The long chain diol/short chain diol/diisocyanate ratio in the polyurethane resin used in combination is preferably (15 to 80 wt %)/(5 to 40 wt %)/(15 to 50 wt %).

The concentration of urethane groups in the polyurethane resin used in combination is preferably 1 to 5 meq/g, and more preferably 1.5 to 4.5 meq/g. When it is in this range, the mechanical strength is high, and since the solution viscosity is good high dispersibility can be obtained, which is preferable.

The glass transition temperature of the polyurethane resin used in combination is preferably 0° C. to 200° C., and more preferably 40° C. to 160° C. When it is in this range, the durability is excellent, the calender moldability is good, and good electromagnetic conversion characteristics can therefore be obtained, which is preferable.

With regard to a method for introducing the adsorbing functional group (polar group) into the polyurethane resin used in combination, there are, for example, a method in which the functional group is used in a part of the long chain diol monomer, a method in which it is used in a part of the short chain diol, and a method in which, after the polyurethane is formed by polymerization, the polar group is introduced by a polymer reaction.

As the vinyl chloride resin used in combination with the polyurethane resin of the present invention a copolymer of a vinyl chloride monomer and various types of monomer is used.

Examples of the comonomer include fatty acid vinyl esters such as vinyl acetate and vinyl propionate, acrylates and methacrylates such as methyl(meth)acrylate, ethyl (meth) acrylate, isopropyl(meth)acrylate, butyl(meth)acrylate, and benzyl (meth)acrylate, alkyl allyl ethers such as allyl methyl ether, allyl ethyl ether, allyl propyl ether, and allyl butyl ether, and others such as styrene, α-methylstyrene, vinylidene chloride, acrylonitrile, ethylene, butadiene, and acrylamide; examples of a comonomer having a functional group include vinyl alcohol, 2-hydroxyethyl(meth)acrylate, polyethylene glycol (meth)acrylate, 2-hydroxypropyl(meth)acrylate, 3-hydroxypropyl (meth)acrylate, polypropylene glycol (meth)acrylate, 2-hydroxyethyl allyl ether, 2-hydroxypropyl allyl ether, 3-hydroxypropyl allyl ether, p-vinylphenol, maleic acid, maleic anhydride, acrylic acid, methacrylic acid, glydicyl(meth)acrylate, allyl glycidyl ether, phosphoethyl (meth)acrylate, sulfoethyl(meth)acrylate, p-styrenesulfonic acid, and Na salts and K salts thereof.

The proportion of the vinyl chloride monomer in the vinyl chloride resin is preferably 60 to 95 wt %. It is preferable if it is in this range since good mechanical strength can be obtained, the solvent solubility is good, and good dispersibility can be obtained due to an appropriate solution viscosity.

A preferred amount of a functional group for improving the curing properties of the adsorbing functional group (polar group) and the polyisocyanate curing agent is as described above. With regard to a method for introducing this functional group, a monomer containing the above-mentioned functional group can be copolymerized, or after the vinyl chloride resin is formed by copolymerization, the functional group can be introduced by a polymer reaction.

A preferred degree of polymerization is 200 to 600, and more preferably 240 to 450. It is preferable if it is in this range, since good mechanical strength can be obtained, and good dispersibility can be obtained due to an appropriate solution viscosity.

In order to crosslink and cure the binder used in the present invention so as to improve the mechanical strength and the thermal resistance of a coating, a curing agent can be used. Preferred examples of the curing agent include polyisocyanate compounds. It is preferable for the polyisocyanate compound to be a tri- or higher-functional polyisocyanate.

Specific examples thereof include adduct type polyisocyanate compounds such as a compound obtained by adding 3 mol of TDI (tolylene diisocyanate) to 1 mol of trimethylolpropane (TMP), a compound obtained by adding 3 mol of HDI (hexamethylene diisocyanate) to 1 mole of TMP, a compound obtained by adding 3 mol of IPDI (isophorone diisocyanate) to 1 mole of TMP, and a compound obtained by adding 3 mol of XDI (xylylene diisocyanate) to 1 mole of TMP; TDI condensation isocyanurate type trimer, TDI condensation isocyanurate type pentamer, TDI condensation isocyanurate type heptamer, mixtures thereof; an HDI isocyanurate type condensate, an IPDI isocyanurate type condensate; and crude MDI.

Among these, the compound obtained by adding 3 mol of TDI to 1 mol of TMP, TDI isocyanurate type trimer, etc. are preferable.

Other than the isocyanate curing agents, a curing agent that cures when exposed to radiation such as an electron beam or ultraviolet rays can be used. In this case, it is possible to use a curing agent having, as radiation-curing functional groups, two or more, and preferably three or more, acryloyl or methacryloyl groups. Examples thereof include TMP (trimethylolpropane) triacrylate, pentaerythritol tetraacrylate, and a urethane acrylate oligomer. In this case, it is preferable to introduce a (meth)acryloyl group not only to the curing agent but also to the binder. In the case of curing with ultraviolet rays, a photosensitizer is additionally used.

It is preferable to add 0 to 80 parts by weight of the curing agent relative to 100 parts by weight of the binder. It is preferable if it is in this range since the dispersibility is good.

The amount of binder added to the magnetic layer is preferably 5 to 30 parts by weight relative to 100 parts by weight of the ferromagnetic powder, and more preferably 10 to 20 parts by weight.

Furthermore, it is preferable for the content of the polyurethane resin of the present invention to be at least 50 wt % of the total binder, more preferably 60 to 100 wt %, and particularly preferably 70 to 100 wt %.

It is preferable for the amount thereof added in the binder to be in the above-mentioned range since the dispersion properties are good.

Ferromagnetic Powder

The magnetic recording medium of the present invention preferably comprises as a ferromagnetic powder an acicular ferromagnetic substance having an average major axis length of at least 20 nm but no greater than 50 nm, a tabular ferromagnetic substance having an average plate size of at least 10 nm but no greater than 50 nm, or a spherical or spheroidal magnetic substance having an average diameter of at least 10 nm but no greater than 50 nm. Each thereof is explained below.

(1) Acicular Ferromagnetic Substance

As the ferromagnetic powder used in the magnetic recording medium of the present invention, it is preferable to use an acicular ferromagnetic substance having an average major axis length of at least 20 nm but no greater than 50 nm. Examples of the acicular ferromagnetic substance include an acicular ferromagnetic metal powder such as cobalt-containing ferromagnetic iron oxide or ferromagnetic alloy powder, and the BET specific surface area ($S_{BET}$) is preferably at least 40 m$^2$/g but no greater than 80 m$^2$/g, and more preferably at least 50 m$^2$/g but no greater than 70 m$^2$/g. The crystallite size is preferably at least 8 nm but no greater than 25 nm, more preferably at least 9 nm but no greater than 22 nm, and particularly preferably at least 10 nm but no greater than 20 nm. The major axis length is preferably at least 20 nm but no greater than 50 nm, and more preferably at least 20 nm but no greater than 45 nm.

Examples of the ferromagnetic metal powder include yttrium-containing Fe, Fe—Co, Fe—Ni, and Co—Ni—Fe, and the yttrium content in the ferromagnetic metal powder is preferably 0.5 atom % to 20 atom % as the yttrium atom/Fe atom ratio Y/Fe, and more preferably 5 to 10 atom %. It is preferable if it is in such a range since it is possible to obtain good saturation magnetization for the ferromagnetic metal powder, and the magnetic properties are improved. Since the iron content is high, the magnetic properties are good, and this is preferable since good electromagnetic conversion characteristics are obtained. Furthermore, it is also possible for aluminum, silicon, sulfur, scandium, titanium, vanadium, chromium, manganese, copper, zinc, molybdenum, rhodium, palladium, tin, antimony, boron, barium, tantalum, tungsten, rhenium, gold, lead, phosphorus, lanthanum, cerium, praseodymium, neodymium, tellurium, bismuth, etc. to be present at 20 atom % or less relative to 100 atom % of iron. It is also possible for the ferromagnetic metal powder to contain a small amount of water, a hydroxide, or an oxide.

One example of a process for producing the ferromagnetic metal powder used in the present invention, into which cobalt or yttrium has been introduced, is illustrated below.

For example, an iron oxyhydroxide obtained by blowing an oxidizing gas into an aqueous suspension in which a ferrous salt and an alkali have been mixed can be used as a starting material.

This iron oxyhydroxide is preferably of the α-FeOOH type, and with regard to a production process therefor, there is a first production process in which a ferrous salt is neutralized with an alkali hydroxide to form an aqueous suspension of Fe(OH)$_2$, and an oxidizing gas is blown into this suspension to give acicular α-FeOOH. There is also a second production process in which a ferrous salt is neutralized with an alkali carbonate to form an aqueous suspension of FeCO$_3$, and an oxidizing gas is blown into this suspension to give spindle-shaped α-FeOOH. Such an iron oxyhydroxide is preferably obtained by reacting an aqueous solution of a ferrous salt with an aqueous solution of an alkali to give an aqueous solution containing ferrous hydroxide, and then oxidizing this with air, etc. In this case, the aqueous solution of the ferrous salt may contain a Ni salt, a salt of an alkaline earth element such as Ca, Ba, or Sr, a Cr salt, a Zn salt, etc., and by selecting these salts appropriately the particle shape (axial ratio), etc. can be adjusted.

As the ferrous salt, ferrous chloride, ferrous sulfate, etc. are preferable. As the alkali, sodium hydroxide, aqueous ammonia, ammonium carbonate, sodium carbonate, etc. are preferable. With regard to salts that can be present at the same time, chlorides such as nickel chloride, calcium chloride, barium chloride, strontium chloride, chromium chloride, and zinc chloride are preferable.

In a case where cobalt is subsequently introduced into the iron, before introducing yttrium, an aqueous solution of a cobalt compound such as cobalt sulfate or cobalt chloride is mixed and stirred with a slurry of the above-mentioned iron oxyhydroxide. After the slurry of iron oxyhydroxide containing cobalt is prepared, an aqueous solution containing a yttrium compound is added to this slurry, and they are stirred and mixed.

Neodymium, samarium, praseodymium, lanthanum, gadolinium, etc. can be introduced into the ferromagnetic metal powder of the present invention as well as yttrium. They can be introduced using a chloride such as yttrium chloride, neodymium chloride, samarium chloride, praseodymium chloride, or lanthanum chloride or a nitrate salt such as neodymium nitrate or gadolinium nitrate, and they can be used in a combination of two or more types.

The coercive force (Hc) of the ferromagnetic metal powder is preferably 159.2 to 238.8 kA/m (2,000 to 3,000 Oe), and more preferably 167.2 to 230.8 kA/m (2,100 to 2,900 Oe).

The saturation magnetic flux density is preferably 150 to 300 mT (1,500 to 3,000 G), and more preferably 160 to 290 mT (1,600 to 2,900 G). The saturation magnetization (as) is preferably 140 to 170 A·m$^2$/kg (140 to 170 emu/g), and more preferably 145 to 160 A·m$^2$/kg (145 to 160 emu/g).

The SFD (switching field distribution) of the magnetic substance itself is preferably low, and 0.8 or less is preferred. When the SFD is 0.8 or less, the electromagnetic conversion characteristics become good, the output becomes high, the magnetization reversal becomes sharp with a small peak shift, and it is suitable for high-recording-density digital magnetic recording. In order to narrow the Hc distribution, there are a technique of improving the particle distribution of goethite, a technique of using monodispersed α-Fe$_2$O$_3$, and a technique of preventing sintering between particles, etc. in the ferromagnetic metal powder.

(2) Tabular Ferromagnetic Substance

The tabular ferromagnetic substance that can be used in the present invention having an average plate size of 10 to 50 nm is preferably a ferromagnetic hexagonal ferrite powder.

Examples of the ferromagnetic hexagonal ferrite include substitution products of barium ferrite, strontium ferrite, lead ferrite, and calcium ferrite, and Co substitution products. More specifically, magnetoplumbite type barium ferrite and strontium ferrite, magnetoplumbite type ferrite with a particle surface coated with a spinel, magnetoplumbite type barium ferrite and strontium ferrite partially containing a spinel phase, etc., can be cited. In addition to the designated atoms, an atom such as Al, Si, S, Sc, Ti, V, Cr, Cu, Y, Mo, Rh, Pd, Ag, Sn, Sb, Te, Ba, Ta, W, Re, Au, Hg, Pb, Bi, La, Ce, Pr, Nd, P, Co, Mn, Zn, Ni, Sr, B, Ge, Nb, or Zr may be included. In general, those to which Co—Ti, Co—Ti—Zr, Co—Ti—Zn, Ni—Ti—Zn, Nb—Zn—Co, Sb—Zn—Co, Nb—Zn, etc. have been added can be used. Characteristic impurities may be included depending on the starting material and the production process.

The particle size is 10 to 50 nm as a hexagonal plate size, preferably 15 to 45 nm, and more preferably 20 to 35 nm. When a magnetoresistive head is used for playback, the plate size is preferably 40 nm or smaller so as to reduce noise. It is preferable if the plate size is in such a range, since stable magnetization can be expected due to the absence of thermal fluctuations. Furthermore, noise is reduced and it is suitable for high density magnetic recording.

The tabular ratio (plate size/plate thickness) is preferably 1 to 15, and more preferably 2 to 7. When it is in such a range, adequate orientation can be obtained, and noise decreases due to an absence of inter-particle stacking. The $S_{BET}$ of a powder having a particle size within this range is usually 10 to 200 m$^2$/g. The specific surface area substantially coincides with the value obtained by calculation using the plate size and the plate thickness. The crystallite size is preferably 50 to 450 Å, and more preferably 100 to 350 Å. In general, the plate size and the plate thickness distributions are preferably as narrow as possible. Although it is difficult, the distribution can be expressed using a numerical value by randomly measuring 500 particles on a TEM photograph of the particles. The distribution is not a normal distribution in many cases, but the standard deviation calculated with respect to the average size is preferably σ/average size=0.1 to 2.0. In order to narrow the particle size distribution, the reaction system used for forming the particles is made as homogeneous as possible, and the particles so formed are subjected to a distribution-improving treatment. For example, a method of selectively dissolving ultrafine particles in an acid solution is also known.

The coercive force (Hc) measured for the tabular ferromagnetic substance can be adjusted so as to be on the order of 39.8 to 398 kA/m (500 to 5,000 Oe). A higher Hc is advantageous for high-density recording, but it is restricted by the capacity of the recording head. It is usually on the order of 63.7 to 318.4 kA/m (800 to 4,000 Oe), but is preferably 119.4 to 278.6 kA/m (1,500 to 3,500 Oe). When the saturation magnetization of the head exceeds 1.4 T, it is preferably 159.2 kA/m (2,000 Oe) or higher.

The Hc can be controlled by the particle size (plate size, plate thickness), the type and amount of element included, the element replacement sites, the conditions used for the particle formation reaction, etc. The saturation magnetization (σs) is preferably 40 to 80 A·m$^2$/kg (40 to 80 emu/g). A higher as is preferable, but there is a tendency for it to become lower when the particles become finer. In order to improve the σs, making a composite of magnetoplumbite ferrite with spinel ferrite, selecting the types of element included and their amount, etc. are well known. It is also possible to use a W type hexagonal ferrite.

When dispersing the magnetic substance (magnetic powder), the surface of the magnetic particles can be treated with a material that is compatible with a dispersing medium and the polymer. With regard to a surface-treatment agent, an inorganic or organic compound can be used. Representative examples include oxides and hydroxides of Si, Al, P, etc., and various types of silane coupling agents and various kinds of titanium coupling agents. The amount thereof is preferably 0.1% to 10% based on the magnetic substance. The pH of the magnetic substance is also important for dispersion. It is usually on the order of 4 to 12, and although the optimum value depends on the dispersing medium and the polymer, it is selected from on the order of 6 to 10 from the viewpoints of chemical stability and storage properties of the magnetic recording medium. The moisture contained in the magnetic substance also influences the dispersion. Although the optimum value depends on the dispersing medium and the polymer, it is usually 0.01% to 2.0%.

With regard to a production method for the ferromagnetic hexagonal ferrite, there is glass crystallization method (1) in which barium oxide, iron oxide, a metal oxide that replaces iron, and boron oxide, etc. as glass forming materials are mixed so as to give a desired ferrite composition, then melted and rapidly cooled to give an amorphous substance, subsequently reheated, then washed and ground to give a barium ferrite crystal powder; hydrothermal reaction method (2) in which a barium ferrite composition metal salt solution is neutralized with an alkali, and after a by-product is removed, it is heated in a liquid phase at 100° C. or higher, then washed, dried and ground to give a barium ferrite crystal powder; co-precipitation method (3) in which a barium ferrite composition metal salt solution is neutralized with an alkali, and after a by-product is removed, it is dried and treated at 1,100° C. or less, and ground to give a barium ferrite crystal powder, etc., but any production method can be used in the present invention.

(3) Spherical or Ellipsoidal Magnetic Substance

The spherical or ellipsoidal magnetic substance is preferably an iron nitride-based ferromagnetic powder containing $Fe_{16}N_2$ as a main phase. It may comprise, in addition to Fe and N atoms, an atom such as Al, Si, S, Sc, Ti, V, Cr, Cu, Y, Mo, Rh, Pd, Ag, Sn, Sb, Te, Ba, Ta, W, Re, Au, Hg, Pb, Bi, La, Ce, Pr, Nd, P, Co, Mn, Zn, Ni, Sr, B, Ge, or Nb. The content of N relative to Fe is preferably 1.0 to 20.0 atom %.

The iron nitride is preferably spherical or ellipsoidal, and the major axis length/minor axis length axial ratio is preferably 1 to 2. The BET specific surface area ($S_{BET}$) is preferably 30 to 100 $m^2/g$, and more preferably 50 to 70 $m^2/g$. The crystallite size is preferably 12 to 25 nm, and more preferably 13 to 22 nm.

The saturation magnetization σs is preferably 50 to 200 $A \cdot m^2/kg$ (emu/g), and more preferably 70 to 150 $A \cdot m^2/kg$ (emu/g).

Other Components

The magnetic layer of the present invention can contain an additive as necessary. Examples of the additive include an abrasive, a lubricant, a dispersant/dispersion adjuvant, a fungicide, an antistatic agent, an antioxidant, a solvent, and carbon black.

Examples of these additives include molybdenum disulfide, tungsten disulfide, graphite, boron nitride, graphite fluoride, a silicone oil, a polar group-containing silicone, a fatty acid-modified silicone, a fluorine-containing silicone, a fluorine-containing alcohol, a fluorine-containing ester, a polyolefin, a polyglycol, a polyphenyl ether; aromatic ring-containing organic phosphonic acids such as phenylphosphonic acid, benzylphosphonic acid, phenethylphosphonic acid, α-methylbenzylphosphonic acid, 1-methyl-1-phenethylphosphonic acid, diphenylmethylphosphonic acid, biphenylphosphonic acid, benzylphenylphosphonic acid, α-cumylphosphonic acid, tolylphosphonic acid, xylylphosphonic acid, ethylphenylphosphonic acid, cumenylphosphonic acid, propylphenylphosphonic acid, butylphenylphosphonic acid, heptylphenylphosphonic acid, octylphenylphosphonic acid, and nonylphenylphosphonic acid, and alkali metal salts thereof; alkylphosphonic acids such as octylphosphonic acid, 2-ethylhexylphosphonic acid, isooctylphosphonic acid, isononylphosphonic acid, isodecylphosphonic acid, isoundecylphosphonic acid, isododecylphosphonic acid, isohexadecylphosphonic acid, isooctadecylphosphonic acid, and isoeicosylphosphonic acid, and alkali metal salts thereof; aromatic phosphates such as phenyl phosphate, benzyl phosphate, phenethyl phosphate, α-methylbenzyl phosphate, 1-methyl-1-phenethyl phosphate, diphenylmethyl phosphate, biphenyl phosphate, benzylphenyl phosphate, α-cumyl phosphate, tolyl phosphate, xylyl phosphate, ethylphenyl phosphate, cumenyl phosphate, propylphenyl phosphate, butylphenyl phosphate, heptylphenyl phosphate, octylphenyl phosphate, and nonylphenyl phosphate, and alkali metal salts thereof; alkyl phosphates such as octyl phosphate, 2-ethylhexyl phosphate, isooctyl phosphate, isononyl phosphate, isodecyl phosphate, isoundecyl phosphate, isododecyl phosphate, isohexadecyl phosphate, isooctadecyl phosphate, and isoeicosyl phosphate, and alkali metal salts thereof; alkyl sulfonates and alkali metal salts thereof; fluorine-containing alkyl sulfates and alkali metal salts thereof; monobasic fatty acids that have 10 to 24 carbons, may contain an unsaturated bond, and may be branched, such as lauric acid, myristic acid, palmitic acid, stearic acid, behenic acid, oleic acid, linoleic acid, linolenic acid, elaidic acid, and erucic acid, and metal salts thereof; mono-fatty acid esters, di-fatty acid esters, and poly-fatty acid esters such as butyl stearate, octyl stearate, amyl stearate, isooctyl stearate, octyl myristate, butyl laurate, butoxyethyl stearate, anhydrosorbitan monostearate, anhydrosorbitan distearate, and anhydrosorbitan tristearate that are formed from a monobasic fatty acid that has 10 to 24 carbons, may contain an unsaturated bond, and may be branched, and any one of a mono- to hexa-hydric alcohol that has 2 to 22 carbons, may contain an unsaturated bond, and may be branched, an alkoxy alcohol that has 12 to 22 carbons, may have an unsaturated bond, and may be branched, and a mono alkyl ether of an alkylene oxide polymer; fatty acid amides having 2 to 22 carbons; aliphatic amines having 8 to 22 carbons; etc. Other than the above-mentioned hydrocarbon groups, those having an alkyl, aryl, or aralkyl group that is substituted with a group other than a hydrocarbon group, such as a nitro group, F, Cl, Br, or a halogen-containing hydrocarbon such as $CF_3$, $CCl_3$, or $CBr_3$ can also be used.

Furthermore, there are a nonionic surfactant such as an alkylene oxide type, a glycerol type, a glycidol type, or an alkylphenol-ethylene oxide adduct; a cationic surfactant such as a cyclic amine, an ester amide, a quaternary ammonium salt, a hydantoin derivative, a heterocyclic compound, a phosphonium salt, or a sulfonium salt; an anionic surfactant containing an acidic group such as a carboxylic acid, a sulfonic acid, or a sulfate ester group; and an amphoteric surfactant such as an amino acid, an aminosulfonic acid, a sulfate ester or a phosphate ester of an amino alcohol, or an alkylbetaine. Details of these surfactants are described in 'Kaimenkasseizai Binran' (Surfactant Handbook) (Published by Sangyo Tosho Publishing).

These dispersants, lubricants, etc. need not always be pure and may contain, in addition to the main component, an impurity such as an isomer, an unreacted material, a by-product, a decomposition product, or an oxide. However, the impurity content is preferably 30 wt % or less, and more preferably 10 wt % or less.

Specific examples of these additives include NAA-102, hardened castor oil fatty acid, NAA-42, Cation SA, Nymeen L-201, Nonion E-208, Anon BF, and Anon LG, (produced by Nippon Oil & Fats Co., Ltd.); FAL-205, and FAL-123 (produced by Takemoto Oil & Fat Co., Ltd), Enujelv OL (produced by New Japan Chemical Co., Ltd.), TA-3 (produced by Shin-Etsu Chemical Industry Co., Ltd.), Amide P (produced by Lion Armour), Duomin TDO (produced by Lion Corporation), BA-41G (produced by The Nisshin Oil Mills, Ltd.), Profan 2012E, Newpol PE 61, and Ionet MS-400 (produced by Sanyo Chemical Industries, Ltd.).

An organic solvent used for the magnetic layer of the present invention can be a known organic solvent. As the organic solvent, tetrahydrofuran, a ketone such as acetone, methyl ethyl ketone, methyl isobutyl ketone, diisobutyl ketone, cyclohexanone, or isophorone, an alcohol such as methanol, ethanol, propanol, butanol, isobutyl alcohol, isopropyl alcohol, or methylcyclohexanol, an ester such as methyl acetate, butyl acetate, isobutyl acetate, isopropyl acetate, ethyl lactate, or glycol acetate, a glycol ether such as glycol dimethyl ether, glycol monoethyl ether, or dioxane, an aromatic hydrocarbon such as benzene, toluene, xylene, cresol, or chlorobenzene, a chlorohydrocarbon such as methylene chloride, ethylene chloride, carbon tetrachloride, chloroform, ethylene chlorohydrin, or dichlorobenzene, N,N-dimethylformamide, hexane, etc. can be used at any ratio.

These organic solvents do not always need to be 100% pure, and may contain an impurity such as an isomer, an unreacted compound, a by-product, a decomposition product, an oxide, or moisture in addition to the main component. The content of these impurities is preferably 30% or less, and more preferably 10% or less. The organic solvent used in the present invention is preferably the same type for both the magnetic layer and the non-magnetic layer. However, the amount added may be varied. The coating stability is improved by using a high surface tension solvent (cyclohexanone, dioxane, etc.) for the non-magnetic layer; more specifically, it is important that the arithmetic mean value of the surface tension of the upper layer solvent composition is not less than that for the surface tension of the non-magnetic layer solvent composition. In order to improve the dispersibility, it is preferable for the polarity to be somewhat strong, and the solvent composition preferably contains 50% or more of a solvent having a permittivity of 15 or higher. The solubility parameter is preferably 8 to 11.

These dispersants, lubricants, and surfactants used in the magnetic layer of the present invention may be selected as necessary in terms of the type and amount according to the magnetic layer and a non-magnetic layer, which will be described later. All or a part of the additives used in the present invention may be added to a magnetic coating solution or a non-magnetic coating solution at any stage of its preparation. For example, the additives may be blended with a ferromagnetic powder prior to a kneading step, they may be added in a step of kneading a ferromagnetic powder, a binder, and a solvent, they may be added in a dispersing step, they may be added after dispersion, or they may be added immediately prior to coating.

The magnetic layer of the present invention can contain as necessary carbon black.

Types of carbon black that can be used include furnace black for rubber, thermal black for rubber, black for coloring, and acetylene black. The carbon black used in each layer should have characteristics that have been optimized as follows according to a desired effect, and the effect can be obtained by the combined use thereof.

The specific surface area of the carbon black is preferably 100 to 500 $m^2/g$, and more preferably 150 to 400 $m^2/g$, and the oil absorption with dibutyl phthalate (DBP oil absorption) is preferably 20 to 400 mL/100 g, and more preferably 30 to 200 mL/100 g. The particle size of the carbon black is preferably 5 to 80 nm, more preferably 10 to 50 nm, and yet more preferably 10 to 40 nm. The pH of the carbon black is preferably 2 to 10, the water content thereof is preferably 0.1% to 10%, and the tap density is preferably 0.1 to 1 g/mL.

Specific examples of the carbon black used in the present invention include BLACKPEARLS 2000, 1300, 1000, 900, 800, 880 and 700, and VULCAN XC-72 (manufactured by Cabot Corporation), #3050B, #3150B, #3250B, #3750B, #3950B, #950, #650B, #970B, #850B, MA-600, MA-230, #4000 and #4010 (manufactured by Mitsubishi Chemical Corporation), CONDUCTEX SC, RAVEN 8800, 8000, 7000, 5750, 5250, 3500, 2100, 2000, 1800, 1500, 1255 and 1250 (manufactured by Columbian Carbon Co.), and Ketjen Black EC (manufactured by Akzo Nobel).

The carbon black may be subjected to any of a surface treatment with a dispersant, etc., grafting with a resin, or a partial surface graphitization. The carbon black may also be dispersed in a binder prior to addition to a coating solution. The carbon black that can be used in the present invention can be selected by referring to, for example, the 'Kabon Burakku Binran (Carbon Black Handbook)' (edited by the Carbon Black Association of Japan).

The carbon black may be used singly or in a combination of different types thereof. When the carbon black is used, it is preferably used in an amount of 0.1 to 30 wt % based on the weight of the magnetic substance. The carbon black has the functions of preventing static charging of the magnetic layer, reducing the coefficient of friction, imparting light-shielding properties, and improving the film strength. Such functions vary depending upon the type of carbon black. Accordingly, it is of course possible in the present invention to appropriately choose the type, the amount and the combination of carbon black for the magnetic layer according to the intended purpose on the basis of the above mentioned various properties such as the particle size, the oil absorption, the electrical conductivity, and the pH value, and it is better if they are optimized for the respective layers.

II. Non-Magnetic Layer

The magnetic recording medium of the present invention may have at least one non-magnetic layer between the non-magnetic support and the magnetic layer, the non-magnetic layer having dispersed therein a non-magnetic powder and a binder. When the non-magnetic layer is present, it is possible to use, as the binder for the non-magnetic layer, the same binder as that used in the magnetic layer.

Furthermore, particularly when step-growth polymerization is carried out, it is preferable to use as the binder a polyurethane resin obtained by polymerization using a compound represented by Formula (1) above, a diol component having at least one ethylenically unsaturated bond (preferably a (meth)acryloyl group), and a diisocyanate. Furthermore, in this case, it is preferable that, after the non-magnetic layer is applied as described later, curing is carried out by irradiation with radiation (preferably an electron beam).

The non-magnetic powder that can be used in the non-magnetic layer may be an inorganic substance or an organic substance. Furthermore, the non-magnetic layer may comprise as necessary carbon black together with the non-magnetic powder.

Non-Magnetic Powder

The non-magnetic layer may employ a magnetic powder as long as the non-magnetic layer is substantially non-magnetic, but preferably employs a non-magnetic powder.

The non-magnetic powder that can be used in the non-magnetic layer may be an inorganic substance or an organic substance. It is also possible to use carbon black, etc. Examples of the inorganic substance include a metal, a metal oxide, a metal carbonate, a metal sulfate, a metal nitride, a metal carbide, and a metal sulfide.

Specific examples thereof include a titanium oxide such as titanium dioxide, cerium oxide, tin oxide, tungsten oxide, ZnO, $ZrO_2$, $SiO_2$, $Cr_2O_3$, α-alumina having an α-component proportion of 90% to 100%, β-alumina, γ-alumina, α-iron oxide, goethite, corundum, silicon nitride, titanium carbide, magnesium oxide, boron nitride, molybdenum disulfide, copper oxide, $MgCO_3$, $CaCO_3$, $BaCO_3$, $SrCO_3$, $BaSO_4$, silicon carbide, and titanium carbide, and they can be used singly or in a combination of two or more types. α-Iron oxide or a titanium oxide is preferable.

The form of the non-magnetic powder may be any one of acicular, spherical, polyhedral, and tabular.

The crystallite size of the non-magnetic powder is preferably 4 nm to 1 μm, and more preferably 40 to 100 nm. When the crystallite size is in the range of 4 nm to 1 μm, there are no problems with dispersion and a suitable surface roughness is obtained.

The average particle size of these non-magnetic powders is preferably 5 nm to 2 μm, but it is possible to combine non-magnetic powders having different average particle sizes as necessary, or widen the particle size distribution of a single non-magnetic powder, thus producing the same effect. The average particle size of the non-magnetic powder is particularly preferably 10 to 200 nm. It is preferable if it is in the range of 5 nm to 2 μm, since good dispersibility and a suitable surface roughness can be obtained.

The specific surface area of the non-magnetic powder is preferably 1 to 100 $m^2/g$, more preferably 5 to 70 $m^2/g$, and yet more preferably 10 to 65 $m^2/g$. It is preferable if the specific surface area is in the range of 1 to 100 $m^2/g$, since a suitable surface roughness can be obtained, and dispersion can be carried out using a desired amount of binder.

The DBP oil absorption is preferably 5 to 100 mL/100 g, more preferably 10 to 80 mL/100 g, and yet more preferably 20 to 60 mL/100 g.

The specific gravity is preferably 1 to 12, and more preferably 3 to 6. The tap density is preferably 0.05 to 2 g/mL, and more preferably 0.2 to 1.5 g/mL. When the tap density is in the range of 0.05 to 2 g/mL, there is little scattering of particles, the operation is easy, and there tends to be little sticking to equipment.

The pH of the non-magnetic powder is preferably 2 to 11, and particularly preferably 6 to 9. When the pH is in the range of 2 to 11, the coefficient of friction does not increase as a result of high temperature and high humidity or release of a fatty acid.

The water content of the non-magnetic powder is preferably 0.1 to 5 wt %, more preferably 0.2 to 3 wt %, and yet more preferably 0.3 to 1.5 wt %. It is preferable if the water content is in the range of 0.1 to 5 wt %, since dispersion is good, and the viscosity of a dispersed coating solution becomes stable.

The ignition loss is preferably 20 wt % or less, and a small ignition loss is preferable.

When the non-magnetic powder is an inorganic powder, the Mohs hardness thereof is preferably in the range of 4 to 10. When the Mohs hardness is in the range of 4 to 10, it is possible to guarantee the durability. The amount of stearic acid absorbed by the non-magnetic powder is preferably 1 to 20 μmol/$m^2$, and more preferably 2 to 15 μmol/$m^2$.

The heat of wetting of the non-magnetic powder in water at 25° C. is preferably in the range of 20 to 60 μJ/$cm^2$ (200 to 600 erg/$cm^2$). It is possible to use a solvent that gives a heat of wetting in this range.

The number of water molecules on the surface at 100° C. to 400° C. is suitably 1 to 10/100 Å. The pH at the isoelectric point in water is preferably between 3 and 9.

The surface of the non-magnetic powder is preferably subjected to a surface treatment with $Al_2O_3$, $SiO_2$, $TiO_2$, $ZrO_2$, $SnO_2$, $Sb_2O_3$, or ZnO. In terms of dispersibility in particular, $Al_2O_3$, $SiO_2$, $TiO_2$, and $ZrO_2$ are preferable, and $Al_2O_3$, $SiO_2$, and $ZrO_2$ are more preferable.

They may be used in combination or singly. Depending on the intended purpose, a surface-treated layer may be obtained by co-precipitation, or a method can be employed in which the surface is firstly treated with alumina and the surface thereof is then treated with silica, or vice versa. The surface-treated layer may be formed as a porous layer depending on the intended purpose, but it is generally preferable for it to be uniform and dense.

Specific examples of the non-magnetic powder used in the non-magnetic layer of the present invention include Nanotite (manufactured by Showa Denko K.K.), HIT-100 and ZA-G1 (manufactured by Sumitomo Chemical Co., Ltd.), DPN-250, DPN-250BX, DPN-245, DPN-270BX, DPB-550BX, and DPN-550RX (manufactured by Toda Kogyo Corp.), titanium oxide TTO-51B, TTO-55A, TTO-55B, TTO-55C, TTO-55S, TTO-55D, and SN-100, MJ-7, α-iron oxide E270, E271, and E300 (manufactured by Ishihara Sangyo Kaisha Ltd.), titanium oxide STT-4D, STT-30D, STT-30, and STT-65C (manufactured by Titan Kogyo Kabushiki Kaisha), MT-100S, MT-100T, MT-150W, MT-500B, MT-600B, MT-100F, and MT-500HD (manufactured by Tayca Corporation), FINEX-25, BF-1, BF-10, BF-20, and ST-M (manufactured by Sakai Chemical Industry Co., Ltd.), DEFIC-Y and DEFIC-R (manufactured by Dowa Mining Co., Ltd.), AS2BM and TiO2P25 (manufactured by Nippon Aerosil Co., Ltd.), 100A, and 500A (manufactured by Ube Industries, Ltd.), Y-LOP (manufactured by Titan Kogyo Kabushiki Kaisha), and calcined products thereof. Particularly preferred non-magnetic powders are titanium dioxide and α-iron oxide.

By mixing carbon black with the non-magnetic powder, the surface electrical resistance of the non-magnetic layer can be reduced, the light transmittance can be decreased, and a desired μVickers hardness can be obtained. The μVickers hardness of the non-magnetic layer is usually 25 to 60 kg/$mm^2$, and is preferably 30 to 50 kg/$mm^2$ in order to adjust the head contact, and can be measured using a thin film hardness meter (HMA-400 manufactured by NEC Corporation) with, as an indentor tip, a triangular pyramidal diamond needle having a tip angle of 80° and a tip radius of 0.1 μm. The light transmittance is generally standardized such that the absorption of infrared rays having a wavelength of on the order of 900 nm is 3% or less and, in the case of, for example, VHS magnetic tapes, 0.8% or less. Because of this, furnace black for rubber, thermal black for rubber, carbon black for coloring, acetylene black, etc. can be used.

The specific surface area of the carbon black used in the non-magnetic layer of the present invention is preferably 100 to 500 $m^2$ g, and more preferably 150 to 400 $m^2/g$, and the DBP oil absorption thereof is preferably 20 to 400 mL/100 g, and more preferably 30 to 200 mL/100 g. The particle size of the carbon black is preferably 5 to 80 nm, more preferably 10 to 50 nm, and yet more preferably 10 to 40 nm. The pH of the carbon black is preferably 2 to 10, the water content thereof is preferably 0.1% to 10%, and the tap density is preferably 0.1 to 1 g/mL.

Specific examples of the carbon black that can be used in the non-magnetic layer of the present invention include BLACKPEARLS 2000, 1300, 1000, 900, 800, 880 and 700, and VULCAN XC-72 (manufactured by Cabot Corporation), #3050B, #3150B, #3250B, #3750B, #3950B, #950, #650B, #970B, #850B, and MA-600 (manufactured by Mitsubishi Chemical Corporation), CONDUCTEX SC, RAVEN 8800, 8000, 7000, 5750, 5250, 3500, 2100, 2000, 1800, 1500, 1255 and 1250 (manufactured by Columbian Carbon Co.), and Ketjen Black EC (manufactured by Akzo Nobel).

The carbon black may be surface treated using a dispersant or grafted with a resin, or part of the surface thereof may be converted into graphite. Prior to adding carbon black to a coating solution, the carbon black may be predispersed with a binder. The carbon black is preferably used in a range that does not exceed 50 wt % of the above-mentioned inorganic powder and in a range that does not exceed 40 wt % of the total weight of the non-magnetic layer. These types of carbon black may be used singly or in combination. The carbon black that can be used in the non-magnetic layer of the present invention can be selected by referring to, for example, the 'Kabon Burakku Binran' (Carbon Black Handbook) (edited by the Carbon Black Association of Japan).

It is also possible to add an organic powder to the non-magnetic layer, depending on the intended purpose. Examples of such an organic powder include an acrylic styrene resin powder, a benzoguanamine resin powder, a melamine resin powder, and a phthalocyanine pigment, but a polyolefin resin powder, a polyester resin powder, a polyamide resin powder, a polyimide resin powder, and a polyfluoroethylene resin can also be used. Production methods such as those described in JP-A-62-18564 and JP-A-60-255827 can be used.

As a binder resin, lubricant, dispersant, additive, solvent, dispersing method, etc. for the non-magnetic layer, those for the magnetic layer can be employed. In particular, the amount and type of binder, and the amounts and types of additive and dispersant can be determined according to known techniques regarding the magnetic layer.

III. Non-Magnetic Support

With regard to the non-magnetic support that can be used in the present invention, known biaxially stretched films such as polyethylene terephthalate, polyethylene naphthalate, polyamide, polyamideimide, and aromatic polyamide can be used. Polyethylene terephthalate, polyethylene naphthalate, and polyamide are preferred.

These supports can be subjected in advance to a corona discharge treatment, a plasma treatment, a treatment for enhancing adhesion, a thermal treatment, etc. The non-magnetic support that can be used in the present invention preferably has a surface smoothness such that its center plane average roughness Ra is in the range of 3 to 10 nm for a cutoff value of 0.25 mm.

IV. Smoothing Layer

The magnetic recording medium of the present invention may be provided with a smoothing layer. The smoothing layer referred to here is a layer for burying projections on the surface of the non-magnetic support; it is provided between the non-magnetic support and the magnetic layer when the magnetic recording medium is provided with the magnetic layer on the non-magnetic support, and it is provided between the non-magnetic support and the non-magnetic layer when the magnetic recording medium is provided with the non-magnetic layer and the magnetic layer in that order on the non-magnetic support.

The smoothing layer can be formed by curing a radiation curable compound by exposure to radiation. The radiation curable compound referred to here is a compound having the property of polymerizing or crosslinking when irradiated with radiation such as ultraviolet rays or an electron beam, thus increasing the molecular weight and carrying out curing.

V. Backcoat Layer

In general, there is a strong requirement for magnetic tapes for recording computer data to have better repetitive transport properties than video tapes and audio tapes. In order to maintain such high storage stability, a backcoat layer can be provided on the surface of the non-magnetic support opposite to the surface where the non-magnetic layer and the magnetic layer are provided. As a coating solution for the backcoat layer, a binder and a particulate component such as an abrasive or an antistatic agent are dispersed in an organic solvent. As a granular component, various types of inorganic pigment or carbon black can be used. As the binder, a resin such as nitrocellulose, a phenoxy resin, a vinyl chloride resin, or a polyurethane can be used singly or in combination.

VI. Layer Arrangement

In the constitution of the magnetic recording medium used in the present invention, the thickness of the non-magnetic support is preferably 3 to 80 µm. When the undercoat layer is provided between the non-magnetic support and the non-magnetic layer or the magnetic layer, the thickness of the undercoat layer is preferably 0.01 to 0.8 µm, and more preferably 0.02 to 0.6 µm. The thickness of the backcoat layer provided on the surface of the non-magnetic support opposite to the surface where the non-magnetic layer and the magnetic layer are provided is preferably 0.1 to 1.0 µm, and more preferably 0.2 to 0.8 µm.

The thickness of the magnetic layer is optimized according to the saturation magnetization and the head gap of the magnetic head and the bandwidth of the recording signal, but it is preferably 0.01 to 0.10 µm, more preferably at least 0.02 to 0.08 µm, and yet more preferably 0.03 to 0.08 µm. The percentage variation in thickness of the magnetic layer is preferably ±50% or less, and more preferably ±40% or less. The magnetic layer can be at least one layer, but it is also possible to provide two or more separate layers having different magnetic properties, and a known configuration for a multilayer magnetic layer can be employed.

The thickness of the non-magnetic layer of the present invention is preferably 0.2 to 3.0 µm, more preferably 0.3 to 2.5 µm, and yet more preferably 0.4 to 2.0 µm. The non-magnetic layer of the magnetic recording medium of the present invention exhibits its effect if it is substantially non-magnetic, but even if it contains a small amount of a magnetic substance as an impurity or intentionally, if the effects of the present invention are exhibited the constitution can be considered to be substantially the same as that of the magnetic recording medium of the present invention. 'Substantially the same' referred to here means that the non-magnetic layer has a residual magnetic flux density of 10 mT (100 G) or less or a coercive force of 7.96 kA/m (100 Oe) or less, and preferably has no residual magnetic flux density and no coercive force.

VII. Production Method

A process for producing a magnetic layer coating solution for the magnetic recording medium used in the present invention comprises at least a kneading step, a dispersing step and, optionally, a blending step that is carried out prior to and/or subsequent to the above-mentioned steps. Each of these steps may be composed of two or more separate stages. All materials, including the ferromagnetic hexagonal ferrite powder, the ferromagnetic metal powder, the non-magnetic powder, the binder, the carbon black, the abrasive, the antistatic agent, the lubricant, and the solvent used in the present invention may be added in any step from the beginning or during the course of the step. The addition of each material may be divided across two or more steps. For example, a polyurethane can be divided and added in a kneading step, a dispersing step, and a blending step for adjusting the viscosity after dispersion. To attain the object of the present invention, a conventionally known production technique may be employed as a part of the steps. In the kneading step, it is preferable to use a powerful kneading machine such as an open kneader, a continuous kneader, a pressure kneader, or an extruder. When a kneader is used, all or a part of the binder (preferably 30 wt % or above of the entire binder) is preferably kneaded with the magnetic powder or the non-magnetic powder at 15 to 500 parts by weight of the binder relative to 100 parts by weight of the magnetic substance. Details of these kneading treatments are described in JP-A-1-106338 and JP-A-1-79274. For the dispersion of the magnetic layer solution and a non-magnetic layer solution, glass beads can be used. As such glass beads, a dispersing medium having a high specific gravity such as zirconia beads, titania beads, or steel beads is suitably used. An optimal particle size and packing density of these dispersing media is used. A known disperser can be used.

The process for producing the magnetic recording medium of the present invention includes, for example, coating the surface of a moving non-magnetic support with a magnetic layer coating solution so as to give a predetermined coating thickness. A plurality of magnetic layer coating solutions and non-magnetic coating solutions can be applied successively or simultaneously in multilayer coating, and a lower magnetic layer coating solution and an upper magnetic layer coating solution can also be applied successively or simultaneously in multilayer coating. When a coating solution for a lower layer non-magnetic layer and a coating solution for an upper layer magnetic layer are applied successively by multilayer coating, irradiation with radiation may be carried out before coating with the coating solution for the upper layer magnetic layer, and a magnetic layer may be formed on a cured non-magnetic layer. In this case, it is preferable to use as a binder of the non-magnetic layer a polyurethane resin obtained using a compound represented by Formula (1), a diisocyanate, and a diol component having an ethylenically unsaturated bond, preferably a (meth)acryloyl group, and more preferably an acryloyl group. By irradiation with radiation, the ethylenically unsaturated bond (preferably a (meth)acryloyl group, more preferably an acryloyl group) undergoes polymerization/crosslinking to thus increase the molecular weight, and solubility in a solvent contained in the upper layer is desirably reduced.

As coating equipment for applying the above-mentioned magnetic layer coating solution the lower magnetic layer coating solution or the non-magnetic layer coating solution, an air doctor coater, a blade coater, a rod coater, an extrusion coater, an air knife coater, a squeegee coater, a dip coater, a reverse roll coater, a transfer roll coater, a gravure coater, a kiss coater, a cast coater, a spray coater, a spin coater, etc. can be used. With regard to these, for example, 'Saishin Kotingu Gijutsu' (Latest Coating Technology) (May 31, 1983) published by Sogo Gijutsu Center can be referred to.

In the case of a magnetic tape, the coated layer of the magnetic layer coating solution is subjected to a magnetic field alignment treatment in which the ferromagnetic powder contained in the coated layer of the magnetic layer coating solution is aligned in the longitudinal direction using a cobalt magnet or a solenoid. In the case of a disk, although sufficient isotropic alignment can sometimes be obtained without using an alignment device, it is preferable to employ a known random alignment device such as, for example, arranging obliquely alternating cobalt magnets or applying an alternating magnetic field with a solenoid. The isotropic alignment referred to here means that, in the case of a ferromagnetic metal powder, in general, in-plane two-dimensional random is preferable, but it can be three-dimensional random by introducing a vertical component. In the case of a ferromagnetic hexagonal ferrite powder, in general, it tends to be in-plane and vertical three-dimensional random, but in-plane two-dimensional random is also possible. By using a known method such as magnets having different poles facing each other so as to make vertical alignment, circumferentially isotropic magnetic properties can be introduced. In particular, when carrying out high density recording, vertical alignment is preferable. Furthermore, circumferential alignment may be employed using spin coating.

It is preferable for the drying position for the coating to be controlled by controlling the drying temperature and blowing rate and the coating speed; it is preferable for the coating speed to be 20 to 1,000 m/min and the temperature of drying air to be 60° C. or higher, and an appropriate level of pre-drying may be carried out prior to entering a magnet zone.

After drying is carried out, the coated layer is subjected to a surface smoothing treatment. The surface smoothing treatment employs, for example, super calender rolls, etc. By carrying out the surface smoothing treatment, cavities formed by removal of the solvent during drying are eliminated, thereby increasing the packing ratio of the ferromagnetic powder in the magnetic layer, and a magnetic recording medium having high electromagnetic conversion characteristics can thus be obtained.

With regard to calendering rolls, rolls of a heat-resistant plastic such as epoxy, polyimide, polyamide, or polyamide-imide are used. It is also possible to treat with metal rolls. The magnetic recording medium of the present invention preferably has a center plane average roughness in the range of 0.1 to 4.0 nm for a cutoff value of 0.25 mm, and more preferably 0.5 to 3.0 nm, which is extremely smooth. As a method therefor, a magnetic layer formed by selecting a specific ferromagnetic powder and binder as described above is subjected to the above-mentioned calendering treatment. With regard to calendering conditions, the calender roll temperature is preferably in the range of 60° C. to 100° C., more preferably in the range of 70° C. to 100° C., and particularly preferably in the range of 80° C. to 100° C., and the pressure is preferably in the range of 100 to 500 kg/cm, more preferably in the range of 200 to 450 kg/cm, and particularly preferably in the range of 300 to 400 kg/cm.

As thermal shrinkage reducing means, there is a method in which a web is thermally treated while handling it with low tension, and a method (thermal treatment) involving thermal treatment of a tape when it is in a layered configuration such as in bulk or installed in a cassette, and either can be used. In the former method, the effect of the imprint of projections of the surface of the backcoat layer is small, but the thermal shrinkage cannot be greatly reduced. On the other hand, the latter thermal treatment can improve the thermal shrinkage greatly, but since the effect of the imprint of projections of the surface of the backcoat layer is strong, the surface of the magnetic layer is roughened, and this causes the output to decrease and the noise to increase. In particular, a high output and low noise magnetic recording medium can be obtained from the magnetic recording medium having no projections on the surface of the backcoat layer accompanying the thermal treatment. The magnetic recording medium thus obtained can be cut to a desired size using a cutter, a stamper, etc. before use.

VIII. Physical Properties

The saturation magnetic flux density of the magnetic layer of the magnetic recording medium used in the present invention is preferably 100 to 300 T·m (1,000 to 3,000 G). The coercive force (Hc) of the magnetic layer is preferably 143.3 to 318.4 kA/m (1,800 to 4,000 Oe), and more preferably 159.2 to 278.6 kA/m (2,000 to 3,500 Oe). It is preferable for the coercive force distribution to be narrow, and the SFD and SFDr are preferably 0.6 or less, and more preferably 0.2 or less.

The coefficient of friction, with respect to a head, of the magnetic recording medium used in the present invention is preferably 0.5 or less at a temperature of −10° C. to 40° C. and a humidity of 0% to 95%, and more preferably 0.3 or less. The electrostatic potential is preferably −500 V to +500 V. The modulus of elasticity of the magnetic layer at an elongation of 0.5% is preferably 0.98 to 19.6 GPa (100 to 2,000 Kg/mm$^2$) in each direction within the plane, and the breaking strength is preferably 98 to 686 MPa (10 to 70 Kg/mm$^2$); the modulus of elasticity of the magnetic recording medium is preferably 0.98 to 14.7 GPa (100 to 1,500 Kg/mm$^2$) in each direction within the plane, the residual elongation is preferably 0.5% or less, and the thermal shrinkage at any temperature up to and including 100° C. is preferably 1% or less, more preferably 0.5% or less, and yet more preferably 0.1% or less.

The glass transition temperature of the magnetic layer (the maximum point of the loss modulus in a dynamic viscoelasticity measurement at 110 Hz) is preferably 50° C. to 180° C., and that of the non-magnetic layer is preferably 0° C. to 180° C. The loss modulus of elasticity is preferably in the range of $1\times10^7$ to $8\times10^8$ Pa ($1\times10^8$ to $8\times10^9$ dyne/cm$^2$), and the loss tangent is preferably 0.2 or less. When the loss tangent is too large, the problem of tackiness easily occurs. These thermal properties and mechanical properties are preferably substantially identical to within 10% in each direction in the plane of the medium.

The residual solvent in the magnetic layer is preferably 100 mg/m$^2$ or less, and more preferably 10 mg/m$^2$ or less. The porosity of the coating layer is preferably 30 vol % or less for both the non-magnetic layer and the magnetic layer, and more preferably 20 vol % or less. In order to achieve a high output, the porosity is preferably small, but there are cases in which a certain value should be maintained depending on the intended purpose. For example, in the case of disk media where repetitive use is considered to be important, a large porosity is often preferable from the point of view of storage stability.

The center plane average roughness Ra of the magnetic layer is preferably 4.0 nm or less, more preferably 3.0 nm or less, and yet more preferably 2.0 nm or less, when measured using a TOPO-3D digital optical profiler (manufactured by Wyko Corporation). The maximum height $SR_{max}$ of the magnetic layer is preferably 0.5 µm or less, the ten-point average roughness SRz is 0.3 µm or less, the center plane peak height SRp is 0.3 µm or less, the center plane valley depth SRv is 0.3 µm or less, the center plane area factor SSr is 20% to 80%, and the average wavelength Sλa is 5 to 300 µm. It is possible to set the number of surface projections on the magnetic layer having a size of 0.01 to 1 µm at any level in the range of 0 to 2,000 projections per 100(µm)$^2$, and by so doing the electromagnetic conversion characteristics and the coefficient of friction can be optimized, which is preferable. They can be controlled easily by controlling the surface properties of the support by means of a filler, the particle size and the amount of a powder added to the magnetic layer, and the shape of the roll surface in the calendering process. The curl is preferably within ±3 mm.

When the magnetic recording medium of the present invention has a non-magnetic layer and a magnetic layer, it can easily be anticipated that the physical properties of the non-magnetic layer and the magnetic layer can be varied according to the intended purpose. For example, the elastic modulus of the magnetic layer can be made high, thereby improving the storage stability, and at the same time the elastic modulus of the non-magnetic layer can be made lower than that of the magnetic layer, thereby improving the head contact of the magnetic recording medium.

A head used for playback of signals recorded magnetically on the magnetic recording medium of the present invention is not particularly limited, but an MR head is preferably used. When an MR head is used for playback of the magnetic recording medium of the present invention, the MR head is not particularly limited and, for example, a GMR head or a TMR head can be used. A head used for magnetic recording is not particularly limited, but it is preferable for the saturation magnetization to be 1.0 T or more, and preferably 1.5 T or more.

In accordance with the present invention, there can be provided a sulfonic acid polyol compound having excellent solubility in an organic solvent. Furthermore, in accordance with the present invention, there can be provided a polyurethane resin that can give a magnetic recording medium having excellent dispersion properties, coating smoothness, and electromagnetic conversion characteristics, and excellent transport durability, and a magnetic recording medium employing the polyurethane resin.

EXAMPLES

The present invention is specifically explained below by reference to Examples, but the present invention is not limited to the Examples. 'Parts' in the Examples means 'parts by weight' unless otherwise stated.

Example 1

(1-1) Synthesis of Sulfonic Acid (Salt) Diol Compound 100 parts by weight (1 molar equivalent) of 2-aminoethanesulfonic acid and 33.5 parts by weight (1 molar equivalent) of lithium hydroxide monohydrate were added to 250 parts by weight of water, and stirring was carried out at 45° C. for 30 minutes. 156 parts by weight of 1,2-butylene oxide was added thereto, and stirring was carried out at 45° C. for a further 2 hours. 400 parts by weight of toluene was added, stirring was carried out for 10 minutes, and a lower layer was then separated off after allowing it to stand. The lower layer thus obtained was solidified and dried, thus giving lithium bis(2-hydroxybutyl)aminoethanesulfonate (S-1). $^1$H NMR data for (S-1) and their assignments are shown below. Measurement of $^1$H NMR in the examples employed a 400 MHz NMR (BRUKER, AVANCE II-400).

(S-1): $^1$H NMR (D$_2$O=4.75 ppm) δ (ppm)=3.68 (2H, m), 3.10 (2H, m), 2.59 (2H, m), 2.40 (4H, m), 1.45 (4H, m), 0.89 (6H, t).

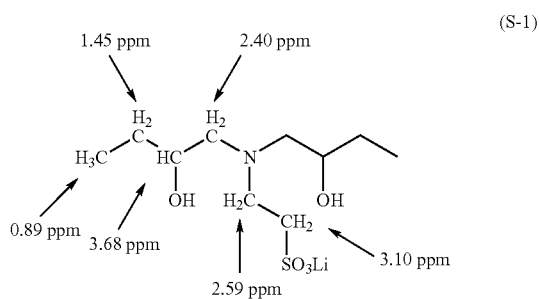

(S-1)

Lithium bis(2-hydroxy-3-butoxypropyl)aminoethane-sulfonate (S-2) was synthesized by the same procedure as in the synthesis of (S-1). $^1$H NMR data for (S-2) and their assignments are shown below.

(S-2): $^1$H NMR (D$_2$O=4.75 ppm) δ (ppm)=3.84 (2H, m), 3.55-3.30 (8H, m), 3.38 (2H, m), 2.95 (4H, m), 2.51 (2H, m), 1.49 (4H, m), 1.27 (4H, m), 0.83 (6H, t).

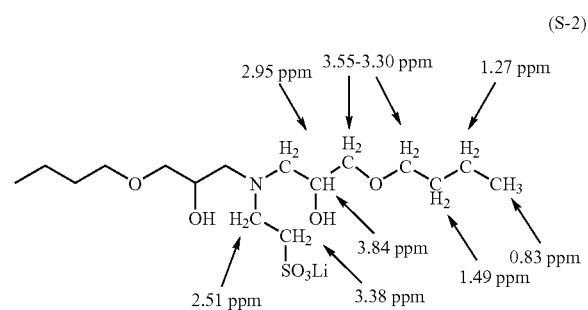

(S-2)

Furthermore, the sulfonic acid (salt) diol compounds (S-3) to (S-33) were synthesized by the same procedure as for (S-1). Among (S-3) to (S-33), for sulfonic acid diol compounds having no salt, a solution of 1 part by weight of the corresponding sulfonic acid salt diol compound and 5 parts by weight of cyclohexanone was subjected to alkali metal ion removal using a strongly acidic ion-exchange resin (Amberlite IRI 120H, Aldrich), thus giving the respective sulfonic acid diol compounds having no salt.

The solubility was checked using each of the sulfonic acid (salt) diol compounds (S-1) to (S-33) above by the method shown below.

(1-2) Solubility Test Method 1 part by weight of sulfonic acid (salt) diol compound was added to 5 parts by weight of cyclohexanone, and dissolution was carried out at 40° C. for 3 hours using ultrasonic waves. A solution thus obtained was filtered, and the presence/absence of a residue after dissolution was checked.

As a result of carrying out the solubility test for each of the sulfonic acid (salt) diol compounds (S-1) to (S-33), no residue was observed after dissolution for any of the sulfonic acid (salt) diol compounds (S-1) to (S-33).

On the other hand, when the solubility test was carried out for each of bis(2-hydroxyethyl)aminoethylsulfonic acid and the lithium salt, sodium salt, and potassium salt thereof, a residue was found for all thereof.

Example 2

Synthesis of Sulfonic Acid (Salt) Group-Containing Diol (1) Synthesis of Sulfonic Acid (Salt) Group-Containing Diol (S2-1)

100 parts by weight of 2-aminoethanesulfonic acid and 33.5 parts by weight of lithium hydroxide monohydrate were added to 250 parts by weight of water, and stirring was carried out at 45° C. for 30 minutes. 156 parts by weight of 1,2-butylene oxide was added thereto, and stirring was carried out at 45° C. for a further 2 hours. 400 parts by weight of toluene was added, stirring was carried out for 10 minutes, and a lower layer was then separated off after allowing it to stand. The lower layer thus obtained was solidified and dried.

(2) Synthesis of S2-2

A target material was obtained by the same procedure as for (1) except that the epoxide used was changed to styrene oxide.

(3) Synthesis of S2-3

100 parts by weight of m-aminobenzenesulfonic acid and 24 parts by weight of lithium hydroxide monohydrate were added to 250 parts by weight of water, and stirring was carried out at 45° C. for 30 minutes. 112 parts by weight of 1,2-butylene oxide was added thereto, and stirring was carried out at 45° C. for a further 2 hours. 400 parts by weight of toluene was added, stirring was carried out for 10 minutes, and a lower layer was then separated off after allowing it to stand. The lower layer thus obtained was solidified and dried.

(4) Synthesis of S2-4

A target material was obtained by the same procedure as for (3) except that the alkali used was changed to sodium hydroxide.

(5) Synthesis of S2-5

A target material was obtained by the same procedure as for (3) except that the alkali used was changed to potassium hydroxide.

(6) Synthesis of S2-6

A target material was obtained by the same procedure as for (3) except that the aminobenzenesulfonic acid used was changed to sodium sulfoethyldiethanolamine, and ethylene oxide was used instead of 1,2-butylene oxide.

TABLE 1

| Sulfonic acid (salt) group-containing diol | Sulfonic acid (salt) group-containing amine (amount used = 1 mol each) | Epoxy compound (amount used) | Molecular weight |
|---|---|---|---|
| S2-1 | Li salt of taurine | 1,2-Butylene oxide (2 mol) | 243.3 |
| S2-2 | Li salt of taurine | Styrene oxide (2 mol) | 367.4 |
| S2-3 | Li salt of m-amino-benzenesulfonic acid | 1,2-Butylene oxide (2 mol) | 323.3 |
| S2-4 | Na salt of m-amino-benzenesulfonic acid | 1,2-Butylene oxide (2 mol) | 339.4 |
| S2-5 | K salt of m-amino-benzenesulfonic acid | 1,2-Butylene oxide (2 mol) | 355.5 |
| S2-6 | Sodium sulfoethyldi-ethanolamine | Ethylene oxide (4 mol) | 411.4 |

Synthesis of Polyurethane Resin

A vessel equipped with a reflux condenser and a stirrer and flushed with nitrogen in advance was charged with a diol component having the composition shown in Table 2 and the reaction catalyst di-n-butyltin laurate so as to give a 50% cyclohexanone solution, and stirring was carried out under a flow of nitrogen at 60° C. for 1 hour. A diisocyanate component shown in Table 2 was further added, and a reaction was carried out at 90° C. for 6 hours, thus giving polyurethane resin solutions A to K.

The reaction catalyst di-n-butyltin laurate was added at 0.01 parts by weight relative to the polymerization components (total amount of polyol and polyisocyanate).

The weight-average molecular weight and weight-average molecular weight/number-average molecular weight ratio of the polyurethanes obtained are given in Table 2. The weight-average molecular weight of the polyurethane was determined on a standard polystyrene basis using DMF solvent containing 0.3 wt % lithium bromide.

The sulfonic acid (salt) concentration (eq/g) is also shown. The sulfonic acid (salt) concentration was determined on the basis of the amount of elemental sulfur per g of polyurethane resin by quantitatively determining the amount of elemental sulfur from the peak area of elemental sulfur (S) in X-ray fluorescence analysis.

Furthermore, the diol component having the composition shown in Table 2 and the reaction catalyst were added so as to give a 50% cyclohexanone solution, stirring was carried out under a flow of nitrogen at 60° C. for 1 hour, and the state of the solution was examined.

The results are given in Table 2 below.

Example 2-1

Preparation of Magnetic Coating Solution 100 parts of a magnetic substance shown in Table 3 was ground in an open kneader for 10 minutes, and then kneaded for 60 minutes with 15 parts (solids content) of polyurethane resin solution 2-A, following which 2 parts of an abrasive ($Al_2O_3$, particle size 0.3 μm), 2 parts of carbon black (particle size 40 μm), and 200 parts of methyl ethyl ketone/toluene=1/1 were added, and the mixture was dispersed in a sand mill for 360 minutes.

To this were added 2 parts of butyl stearate, 1 part of stearic acid, and 50 parts of cyclohexanone, and after stirring the mixture for a further 20 minutes, it was filtered using a filter having an average pore size of 1 μm to give a magnetic coating solution.

Preparation of Lower Layer Non-Magnetic Coating Solution 85 parts of α-$Fe_2O_3$ (average particle size 0.15 μm, $S_{BET}$ 52 m²/g, surface treated with $Al_2O_3$ and $SiO_2$, pH 6.5 to 8.0) was ground in an open kneader for 10 minutes, and then kneaded for 60 minutes with 7.5 parts of an addition compound of sodium hydroxyethylsulfonate with a copolymer of vinyl chloride/vinyl acetate/glycidyl methacrylate=86/9/5 ($SO_3Na=6\times10^{-5}$ eq/g, epoxy=$10^{-3}$ eq/g, Mw 30,000), 10 parts (solids content) of polyurethane resin 2-A, and 60 parts of cyclohexanone, following which

| | |
|---|---|
| methyl ethyl ketone/cyclohexanone = 6/4 was added, and the mixture was dispersed in a sand mill for 120 minutes. To this were added | 200 parts |
| butyl stearate | 2 parts |
| stearic acid | 1 part, and |
| methyl ethyl ketone | 50 parts, |

TABLE 2

| | Diol and diisocyanate used in polyurethane synthesis (molar ratio) | | | | | | | Sulfonic acid | | | |
|---|---|---|---|---|---|---|---|---|---|---|---|
| PU | Diol | | Polar group-containing starting material | | Chain-extending agent | | Diisocyanate | (salt) concentration ($\times 10^{-6}$ eq/g) | Mw | Mw/Mn | 50% cyclohexanone solution after stirring at 60° C. for 1 h |
| 2-A | Polyether A | 22.7 | S2-1 | 2.1 | BPA-PO | 26.3 | MDI | 48.9 | 67 | 70,000 | 1.8 | Dissolved and transparent |
| 2-B | Polyether A | 22.7 | S2-2 | 2.1 | BPA-PO | 26.3 | MDI | 48.9 | 66 | 73,000 | 2.2 | Dissolved and transparent |
| 2-C | Polyether A | 22.7 | S2-3 | 2.1 | BPA-PO | 26.3 | MDI | 48.9 | 66 | 74,000 | 1.8 | Dissolved and transparent |
| 2-D | Polyether A | 22.7 | S2-4 | 2.1 | BPA-PO | 26.3 | MDI | 48.9 | 66 | 73,000 | 1.7 | Dissolved and transparent |
| 2-E | Polyether A | 22.7 | S2-5 | 2.1 | BPA-PO | 26.3 | MDI | 48.9 | 66 | 73,000 | 2.3 | Dissolved and transparent |
| 2-F | Polyether A | 22.8 | S2-1 | 12.0 | BPA-PO | 16.3 | MDI | 48.9 | 373 | 70,000 | 1.8 | Dissolved and transparent |
| 2-G | Polyether A | 22.8 | S2-1 | 27.0 | BPA-PO | 1.3 | MDI | 48.9 | 837 | 70,000 | 1.9 | Dissolved and transparent |
| 2-H | Polyether A | 22.7 | S2-6 | 2.1 | BPA-PO | 26.3 | MDI | 48.9 | 66 | 71,000 | 1.8 | Cloudy |
| 2-I | Polyether A | 22.7 | Li salt of taurine | 2.1 | BPA-PO | 26.3 | MDI | 48.9 | 66 | 73,000 | 2.1 | Cloudy |
| 2-J | Polyether A | 22.8 | S2-1 | 0.3 | BPA-PO | 28.0 | MDI | 48.9 | 9 | 70,000 | 1.9 | Dissolved and transparent |
| 2-K | Polyether A | 22.7 | Polyester A | 2.1 | BPA-PO | 26.3 | MDI | 48.9 | 66 | 72,000 | 1.8 | Dissolved and transparent |

Polyether A: bisphenol A propylene oxide 6 mol adduct (molecular weight 577)
Polyester A: Na sulfoisophthalic acid/2,2-dimethyl-1,3-propanediol = ½ mol reaction product (molecular weight 4,500)
BPA-PO: bisphenol A propylene oxide 2 mol adduct (molecular weight 344)
MDI: 4,4'-diphenylmethane diisocyanate (molecular weight 250)

and after stirring the mixture for a further 20 minutes, it was filtered using a filter having an average pore size of 1 μm to give a lower layer non-magnetic coating solution.

Preparation of Magnetic Recording Medium

A surface of a 7 μm thick polyethylene terephthalate support was coated by means of a wire-wound bar with a sulfonic acid-containing polyester resin as an adhesive layer so that the dry thickness would be 0.1 μm.

Using reverse roll simultaneous multilayer coating, the lower layer non-magnetic coating solution obtained above was then applied at a thickness of 1.5 μm, immediately followed by the upper layer magnetic coating solution, which was applied so that the dry thickness would be 0.1 ↑m. Before the magnetic coating solution had dried, the non-magnetic support coated with the magnetic coating solution was subjected to magnetic field alignment using a 5,000 G Co magnet and a 4,000 G solenoid magnet, and the coating was then subjected to a calender treatment employing a metal roll-metal roll-metal roll-metal roll-metal roll-metal roll-metal roll combination (speed 100 m/min, line pressure 300 kg/cm, temperature 90° C.) and then slit to a width of ½ inch (17.7 mm).

Examples 2-2 to 2-13 and Comparative Examples 2-1 to 2-4

Magnetic recording media were formed by the same method as in Example 2-1 except that the polyurethane resin and the magnetic substance in the upper layer magnetic coating solution were as shown in Table 3.

Magnetic recording media formed in Examples 2-1 to 2-13 and Comparative Examples 2-1 to 2-4 were subjected to the evaluation below.

Measurement Methods (1) Smoothness

The number of projections having a size of 10 to 20 nm was determined by scanning an area of 30 μm×30 μm using a Nanoscope II manufactured by Digital Instruments at a tunnel current of 10 nA and a bias voltage of 400 mV, and the smoothness was expressed as a value relative to 100 for Comparative Example 2-4.

(2) Electromagnetic Conversion Characteristics

Measurement was carried out using a ½ inch linear system with a fixed head. The head/tape relative speed was 10 m/sec. Recording employed a saturation magnetization 1.4 T MIG head (track width 18 μm), and the recording current was set at an optimum current for each tape. The playback head employed was an anisotropic MR head (A-MR) with an element thickness of 25 nm and a shield gap of 0.2 μm.

A signal at a recording wavelength of 0.2 μm was recorded, the playback signal was subjected to frequency analysis by means of a spectrum analyzer manufactured by Shibasoku Co., Ltd., and the ratio of the carrier signal output (wavelength 0.2 μm) to the integrated noise of the entire spectral region was used as the S/N ratio, and was expressed as a relative value where the value of Comparative Example 2-4 was 0 dB.

(3) Repetitive Sliding Durability

A tape was made to slide at a sliding speed of 2 m/sec repeatedly for 10,000 passes under an environment of 40° C. and 10% RH with the magnetic layer surface in contact with an AlTiC cylindrical rod at a load of 100 g (T1), and tape damage was evaluated using the rankings below.

Excellent: slightly scratched, but area without scratches was larger.

Good: area with scratches was larger than area without scratches.

Poor: magnetic layer completely peeled off.

(4) Storage Properties 600 m of a tape was stored at 60° C. and 90% for 2 weeks while wound in a reel for an LTO-G3 cartridge.

The sliding durability of the tape after storage was measured by the same method as in (3).

TABLE 3

| | PU | Magnetic substance | | | Smoothness | Electromagnetic conversion characteristics | Repetitive sliding durability | Storage properties |
| | | Type | Size | | | | | |
| --- | --- | --- | --- | --- | --- | --- | --- | --- |
| Ex. 2-1 | 2-A | Acicular ferromagnetic fine powder | Major axis length | 35 nm | 75 | 0.7 | Excellent | Excellent |
| Ex. 2-2 | 2-B | Acicular ferromagnetic fine powder | Major axis length | 35 nm | 86 | 0.4 | Excellent | Excellent |
| Ex. 2-3 | 2-C | Acicular ferromagnetic fine powder | Major axis length | 35 nm | 74 | 0.7 | Excellent | Excellent |
| Ex. 2-4 | 2-D | Acicular ferromagnetic fine powder | Major axis length | 35 nm | 75 | 0.7 | Excellent | Excellent |
| Ex. 2-5 | 2-E | Acicular ferromagnetic fine powder | Major axis length | 35 nm | 80 | 0.6 | Excellent | Excellent |
| Ex. 2-6 | 2-F | Acicular ferromagnetic fine powder | Major axis length | 35 nm | 90 | 0.3 | Excellent | Excellent |
| Ex. 2-7 | 2-G | Acicular ferromagnetic fine powder | Major axis length | 35 nm | 90 | 0.3 | Excellent | Excellent |
| Ex. 2-8 | 2-A | Acicular ferromagnetic fine powder | Major axis length | 20 nm | 65 | 1 | Excellent | Excellent |
| Ex. 2-9 | 2-A | Acicular ferromagnetic fine powder | Major axis length | 50 nm | 85 | 0.4 | Excellent | Excellent |
| Ex. 2-10 | 2-B | Hexagonal tabular ferrite fine powder | Plate size | 10 nm | 65 | 1 | Excellent | Excellent |
| Ex. 2-11 | 2-B | Hexagonal tabular ferrite fine powder | Plate size | 50 nm | 78 | 0.6 | Excellent | Excellent |
| Ex. 2-12 | 2-A | Spherical iron nitride fine powder | Particle size | 10 nm | 65 | 1 | Excellent | Excellent |
| Ex. 2-13 | 2-A | Spherical iron nitride fine powder | Particle size | 50 nm | 80 | 0.6 | Excellent | Excellent |
| Comp. Ex. 2-1 | 2-H | Acicular ferromagnetic fine powder | Major axis length | 35 nm | 160 | −1.5 | Poor | Poor |
| Comp. Ex. 2-2 | 2-I | Acicular ferromagnetic fine powder | Major axis length | 35 nm | 180 | −1.8 | Poor | Poor |
| Comp. Ex. 2-3 | 2-J | Acicular ferromagnetic fine powder | Major axis length | 35 nm | 185 | −2 | Poor | Poor |
| Comp. Ex. 2-4 | 2-K | Acicular magnetic fine powder | Major axis length | 35 nm | 100 | 0 | Poor | Poor |

Acicular ferromagnetic fine powder: Hc 2,200 Oe, specific surface area 70 m$^2$/g, acicular ratio 3.5, ss 120 emu/g, Fe 89 atom %, Co 5 atom %, Y 6 atom %

Hexagonal tabular ferrite fine powder: Hc 2,200 Oe, specific surface area 55 m$^2$/g, plate ratio 3.5, σs 51 emu/g, Ba 91 atom %, Fe 8 atom %, Co 0.5 atom %, Zn 0.5 atom %

Spherical iron nitride fine powder: Hc 2,200 Oe, specific surface area 56 m$^2$/g, σs 100 emu/g, Fe 88 atom %, N 8 atom %, Y 4 atom %

Example 3

Synthesis of Sulfonic Acid (Salt) Group-Containing Diol (3-1) Synthesis of Sulfonic Acid (Salt) Group-Containing Diol (S3-1)

100 parts by weight of 2-aminoethanesulfonic acid and 33.5 parts by weight of lithium hydroxide monohydrate were added to 250 parts by weight of water, and stirring was carried out at 45° C. for 30 minutes. 156 parts by weight of 1,2-butylene oxide was added thereto, and stirring was carried out at 45° C. for a further 2 hours. 400 parts by weight of toluene was added, stirring was carried out for 10 minutes, and a lower layer was then separated off after allowing it to stand. The lower layer thus obtained was solidified and dried.

(3-2) Synthesis of S3-2

A target material was obtained by the same procedure as in (3-1) except that the epoxide used was changed to styrene oxide.

(3-3) Synthesis of S3-3

A target material was obtained by the same procedure as in (3-1) except that the epoxide used was changed to glycidyl methyl ether.

(3-4) Synthesis of S3-4

A target material was obtained by the same procedure as in (3-1) except that the epoxide used was changed to glycidyl phenyl ether.

(3-5) Synthesis of S3-5

100 parts by weight of m-aminobenzenesulfonic acid and 24 parts by weight of lithium hydroxide monohydrate were added to 250 parts by weight of water, and stirring was carried out at 45° C. for 30 minutes. 112 parts by weight of 1,2-butylene oxide was added thereto, and stirring was carried out at 45° C. for a further 2 hours. 400 parts by weight of toluene was added, stirring was carried out for 10 minutes, and a lower layer was then separated off after allowing it to stand. The lower layer thus obtained was solidified and dried.

(3-6) Synthesis of S3-6

A target material was obtained by converting S3-5 into a sulfonic acid with a strongly acidic ion exchange resin and then neutralizing with sodium hydroxide.

(3-7) Synthesis of S3-7

A target material was obtained by converting S3-5 into a sulfonic acid with a strongly acidic ion exchange resin and then neutralizing with potassium hydroxide.

(3-8) Synthesis of S3-8

A target material was obtained by converting S3-1 into a sulfonic acid with a strongly acidic ion exchange resin and then neutralizing with potassium hydroxide.

(3-9) Synthesis of S3-9

100 parts by weight of 2-aminoethanesulfonic acid and 44.8 parts by weight of potassium hydroxide were added to 250 parts by weight of water, and stirring was carried out 45° C. for 30 minutes. 260 parts by weight of butyl glycidyl ether was added thereto, and stirring was carried out at 45° C. for a further 2 hours. 400 parts by weight of toluene was added, stirring was carried out for 10 min, and a lower layer was then separated off after allowing it to stand. The lower layer thus obtained was solidified and dried.

TABLE 4

| Sulfonic acid (salt) group-containing diol | Sulfonic acid (salt) group-containing amine (amount used = 1 mol each) | Epoxy compound (amount used) | Molecular weight |
|---|---|---|---|
| S3-1 | Li salt of taurine | 1,2-Butylene oxide (2 mol) | 243.3 |
| S3-2 | Li salt of taurine | Styrene oxide (2 mol) | 367.4 |
| S3-3 | Li salt of taurine | Glycidyl methyl ether (2 mol) | 305.4 |
| S3-4 | Li salt of taurine | Glycidyl phenyl ether (2 mol) | 429.5 |
| S3-5 | Li salt of m-aminobenzenesulfonic acid | 1,2-Butylene oxide (2 mol) | 323.3 |
| S3-6 | Li salt of m-aminobenzenesulfonic acid | 1,2-Butylene oxide (2 mol) | 339.4 |
| S3-7 | K salt of m-aminobenzenesulfonic acid | 1,2-Butylene oxide (2 mol) | 355.5 |
| S3-8 | K salt of taurine | 1,2-Butylene oxide (2 mol) | 275.5 |
| S3-9 | K salt of taurine | Butyl glycidyl ether (2 mol) | 423.6 |

Synthesis of Polyester Diol (A)

Dimethyl 5-sodium sulfoisophthalate and 2,2-dimethyl-3-hydroxypropyl-2',2'-dimethyl-3-hydroxypropanate were charged at a molar ratio of 3:4 so that unreacted glycol component remained. A reactor equipped with a thermometer, a stirrer, and a Liebig condenser was charged with 888 parts of dimethyl 5-sodium sulfoisophthalate, 1836 parts of 2,2-dimethyl-3-hydroxypropyl-2',2'-dimethyl-3-hydroxypropanate, and 0.2 parts of tetrabutoxytitanium, and ester exchange was carried out at 240° C. for 5 hours. The temperature was decreased to 100° C., and dilution with 633 parts of toluene was carried out, thus giving a solution of polyester diol (A) (solids concentration: 80 wt %). The number-average molecular weight of polyester diol (A) obtained was 1,500.

Synthesis of Polyurethane Resin

A vessel equipped with a reflux condenser and a stirrer and flushed with nitrogen in advance was charged with a diol component having the composition shown in Table 5 and the reaction catalyst di-n-butyltin laurate so as to give a 50% cyclohexanone solution, and stirring was carried out under a flow of nitrogen at 60° C. for 1 hour. A diisocyanate component shown in Table 5 was further added, and a reaction was carried out at 90° C. for 6 hours, thus giving polyurethane resin solutions 3-A to 3-L.

The reaction catalyst di-n-butyltin laurate was added at 0.01 parts by weight relative to the polymerization components (total amount of polyol and polyisocyanate).

The weight-average molecular weight and weight-average molecular weight/number-average molecular weight ratio (Mw/Mn) of the polyurethanes obtained are given in Table 5. The weight-average molecular weight of the polyurethane was determined on a standard polystyrene basis using DMF solvent containing 0.3 wt % lithium bromide.

The sulfonic acid (salt) concentration (eq/g) is also shown. The sulfonic acid (salt) concentration was determined on the basis of the amount of elemental sulfur per g of polyurethane resin by quantitatively determining the amount of elemental sulfur from the peak area of elemental sulfur (S) in X-ray fluorescence analysis.

Furthermore, the diol component having the composition shown in Table 5 and the reaction catalyst were added so as to give a 50% cyclohexanone solution, stirring was carried out under a flow of nitrogen at 60° C. for 1 hour, and the state of the solution was examined.

The results are given in Table 5 below.

Preparation of Lower Layer Non-Magnetic Coating Solution 85 parts of α-Fe$_2$O$_3$ (average particle size of 0.15 µm, S$_{BET}$ 52 m$^2$/g, surface treated with Al$_2$O$_3$ and SiO$_2$, pH 6.5 to 8.0) was ground in an open kneader for 10 minutes, and then kneaded for 60 minutes with 7.5 parts of an addition compound of sodium hydroxyethylsulfonate with a copolymer of

TABLE 5

| PU | Diol | | Polar group-containing starting material | | Chain-extending agent | | Diisocyanate | | Sulfonic acid (salt) concentration (×10−6 eq/g) | Mw | Mw/Mn | 50% cyclohexanone solution after stirring at 60° C. for 1 h |
|---|---|---|---|---|---|---|---|---|---|---|---|---|
| 3-A | Polyether A | 22.7 | S3-1 | 2.1 | TCDM | 26.3 | | MDI | 48.9 | 67 | 70,000 | 1.9 | Dissolved and transparent |
| 3-B | Polyether A | 22.7 | S3-2 | 2.1 | TCDM | 26.3 | | MDI | 48.9 | 66 | 73,000 | 1.9 | Dissolved and transparent |
| 3-C | Polyether A | 22.7 | S3-3 | 2.1 | TCDM | 26.3 | | MDI | 48.9 | 67 | 72,000 | 1.8 | Dissolved and transparent |
| 3-D | Polyether A | 22.7 | S3-4 | 2.1 | TCDM | 26.3 | | MDI | 48.9 | 66 | 70,000 | 1.9 | Dissolved and transparent |
| 3-E | Polyether A | 22.7 | S3-5 | 2.1 | TCDM | 26.3 | | MDI | 48.9 | 66 | 74,000 | 2.1 | Dissolved and transparent |
| 3-F | Polyether A | 22.7 | S3-6 | 2.1 | TCDM | 26.3 | | MDI | 48.9 | 66 | 73,000 | 1.9 | Dissolved and transparent |
| 3-G | Polyether A | 22.7 | S3-7 | 2.1 | TCDM | 26.3 | | MDI | 48.9 | 66 | 73,000 | 1.9 | Dissolved and transparent |
| 3-H | Polyether A | 22.8 | S3-1 | 12 | TCDM | 16.3 | | MDI | 48.9 | 373 | 70,000 | 1.9 | Dissolved and transparent |
| 3-I | Polyether A | 22.8 | S3-1 | 27 | TCDM | 1.3 | | MDI | 48.9 | 837 | 70,000 | 1.9 | Dissolved and transparent |
| 3-M | Polyether A | 22.7 | S3-1 | 2.1 | TCDM | 13.3 | GLM | 13 MDI | 48.9 | 67 | 70,000 | 1.8 | Dissolved and transparent |
| 3-N | Polyether A | 22.7 | S3-8 | 2.1 | TCDM | 13.3 | GLM | 13 MDI | 48.9 | 66 | 76,000 | 2.2 | Dissolved and transparent |
| 3-O | Polyether A | 22.7 | S3-9 | 2.1 | TCDM | 13.3 | GLM | 13 MDI | 48.9 | 67 | 77,000 | 2.2 | Dissolved and transparent |
| 3-P | Polyether A | 22.7 | S3-1 | 2.1 | TCDM | 13.3 | BpA-EA | 13 MDI | 48.9 | 67 | 75,000 | 2.2 | Dissolved and transparent |
| 3-J | Polyether A | 22.7 | Li salt of taurine | 2.1 | BpA-PO | 26.3 | | MDI | 48.9 | 66 | 73,000 | 1.9 | Cloudy |
| 3-K | Polyether A | 22.7 | Polyester diol (A) | 2.1 | BpA-PO | 26.3 | | MDI | 48.9 | 66 | 72,000 | 1.9 | Dissolved and transparent |
| 3-L | Polyether A | 22.8 | S3-1 | 0.3 | BpA-PO | 28 | | MDI | 48.9 | 9 | 70,000 | 1.8 | Dissolved and transparent |

Polyether A: bisphenol A propylene oxide 6 mol adduct (molecular weight 577)
BpA-PO: bisphenol A propylene oxide 2 mol adduct (molecular weight 344)
MDI: 4,4'-diphenylmethane diisocyanate (molecular weight 250)
TCDM: tricyclodecanedimethanol (molecular weight 196)
GLM: glycerol monomethacrylate (molecular weight 160)
BpA-EA: bisphenol A epoxy acrylate 2 mol adduct (molecular weight 485)

Example 3-1

Preparation of Magnetic Coating Solution 100 parts of a magnetic substance shown in Table 6 was ground in an open kneader for 10 minutes, and then kneaded for 60 minutes with 15 parts (solids content) of polyurethane resin solution 3-A, following which 2 parts of an abrasive (Al$_2$O$_3$, particle size 0.3 µm), 2 parts of carbon black (particle size 40 µm), and 200 parts of methyl ethyl ketone/toluene=1/1 were added, and the mixture was dispersed in a sand mill for 360 minutes.

To this were added 2 parts of butyl stearate, 1 part of stearic acid, and 50 parts of cyclohexanone and, moreover, 6 parts of a trifunctional low-molecular-weight polyisocyanate compound (Coronate 3041, Nippon Polyurethane Industry Co., Ltd.), and after stirring the mixture for a further 20 minutes, it was filtered using a filter having an average pore size of 1 µm to give a magnetic coating solution for a magnetic layer (for upper layer).

vinyl chloride/vinyl acetate/glycidyl methacrylate=86/9/5 (SO$_3$Na=6×10$^{-5}$ eq/g, epoxy=10$^{-3}$ eq/g, Mw 30,000), 10 parts (solids content) of polyurethane resin 3-A, and 60 parts of cyclohexanone, following which

| | |
|---|---|
| methyl ethyl ketone/cyclohexanone = 6/4 | 200 parts | was added, and the mixture was dispersed in a sand mill for 120 minutes. To this were added

| | |
|---|---|
| butyl stearate | 2 parts |
| stearic acid | 1 part, and |
| methyl ethyl ketone | 50 parts, |

50 parts of a trifunctional low-molecular-weight polyisocyanate compound (Coronate 3041, Nippon Polyurethane Industry Co., Ltd.) was added, and after stirring the mixture for a further 20 minutes, it was filtered using a filter having an average pore size of 1 µm to give a lower layer non-magnetic coating solution.

Preparation of Magnetic Recording Medium

A surface of a 7 μm thick polyethylene terephthalate support was coated by means of a wire-wound bar with a sulfonic acid-containing polyester resin as an adhesive layer so that the dry thickness would be 0.1 μm.

Using reverse roll simultaneous multilayer coating, the lower layer non-magnetic coating solution obtained above was then applied at a thickness of 1.5 μm, immediately followed by the upper layer magnetic coating solution, which was applied so that the dry thickness would be 0.1 μm. Before the magnetic coating solution had dried, the non-magnetic support coated with the magnetic coating solution was subjected to magnetic field alignment using a 5,000 G Co magnet and a 4,000 G solenoid magnet, and the coating was then subjected to a calender treatment employing a metal roll-metal roll-metal roll-metal roll-metal roll-metal roll-metal roll combination (speed 100 m/min, line pressure 300 kg/cm, temperature 90° C.) and then slit to a width of 1⁄2 inch (17.7 mm).

Examples 3-2 to 3-15 and Comparative Examples 3-1 to 3-3

Magnetic recording media were formed by the same method as in Example 3-1 except that the polyurethane resin and the magnetic substance in the upper layer magnetic coating solution were as shown in Table 6.

Example 3-16

Preparation of Magnetic Coating Solution

Prepared in the same manner as in Example 3-1.

Preparation of Lower Layer Non-Magnetic Coating Solution 85 parts of α-$Fe_2O_3$ (average particle size 0.15 μm, $S_{BET}$ 52 m²/g, surface treated with $Al_2O_3$ and $SiO_2$, pH 6.5 to 8.0) was ground in an open kneader for 10 minutes, and then kneaded for 60 minutes with 7.5 parts of a resin (methacrylate group content 350×10⁻⁶ eq/g) in which a methacrylate group was imparted using 2-isocyanatoethyl methacrylate (MOI) to an addition compound of potassium hydroxyethylsulfonate with a copolymer of vinyl chloride/vinyl acetate/glycidyl methacrylate=86/9/5 ($SO_3K$=6×10⁻⁵ eq/g, epoxy=10⁻³ eq/g, Mw 30,000), 10 parts (solids content) of polyurethane resin 3-M, and 60 parts of cyclohexanone, following which

| | |
|---|---|
| methyl ethyl ketone/cyclohexanone = 6/4 was added, and the mixture was dispersed in a sand mill for 120 minutes. To this were added | 200 parts |
| butyl stearate | 2 parts |
| stearic acid | 1 part, and |
| methyl ethyl ketone | 50 parts, |

50 parts of dipentaerythritol hexaacrylate was added, and after stirring the mixture for a further 20 minutes, it was filtered using a filter having an average pore size of 1 μm to give a lower layer non-magnetic coating solution.

Preparation of Magnetic Recording Medium

A surface of a 10 μm thick aramid support was coated by means of a wire-wound bar with a sulfonic acid-containing polyester resin as an adhesive layer so that the dry thickness would be 0.1 μm. The lower layer non-magnetic coating solution was then applied at a dry thickness of 1 μm.

Subsequently, a non-magnetic layer was formed by irradiating with an electron beam at an acceleration voltage of 175 kV and a beam current of 10 mA so as to give an absorbed dose of 10 Mrad, thus carrying out curing.

The magnetic coating solution was applied onto the non-magnetic layer thus formed using a reverse roll so as to give a dry coat thickness of 0.1 μm. Before the magnetic coating solution had dried, it was subjected to magnetic field alignment using a 0.5 T (5,000 G) Co magnet and a 0.4 T (4,000 G) solenoid magnet, and the coating was then subjected to a calender treatment employing a metal roll-metal roll-metal roll-metal roll-metal roll-metal roll-metal roll combination (speed 100 m/min, line pressure 300 kg/cm, temperature 90° C.). It was further subjected to a thermal curing treatment at 70° C. for 24 hours, and then slit to a width of 1⁄2 inch (17.7 mm).

Examples 3-17 to 3-19 and Comparative Examples 3-4 to 3-6

Magnetic recording media were formed by the same method as in Example 3-16 except that the polyurethane resin and the magnetic substance in the non-magnetic coating solution were as shown in Table 6.

Magnetic recording media formed in Examples 3-1 to 3-19 and Comparative Examples 3-1 to 3-6 were subjected to the evaluation below.

Measurement Methods (1) Smoothness

The number of projections having a size of 10 to 20 nm was determined by scanning an area of 30 μm×30 μm using a Nanoscope II manufactured by Digital Instruments at a tunnel current of 10 nA and a bias voltage of 400 mV, and the smoothness was expressed as a value relative to 100 for Comparative Example 3-2.

(2) Electromagnetic Conversion Characteristics

Measurement was carried out using a 1⁄2 inch linear system with a fixed head. The head/tape relative speed was 10 m/sec. Recording employed a saturation magnetization 1.4 T MIG head (track width 18 μm), and the recording current was set at an optimum current for each tape. The playback head employed was an anisotropic MR head (A-MR) with an element thickness of 25 nm and a shield gap of 0.2 μm.

A signal at a recording wavelength of 0.2 μm was recorded, the playback signal was subjected to frequency analysis by means of a spectrum analyzer manufactured by Shibasoku Co., Ltd., and the ratio of the carrier signal output (wavelength 0.2 μm) to the integrated noise of the entire spectral region was used as the S/N ratio, and was expressed as a relative value where the value of Comparative Example 3-2 was 0 dB.

(3) Repetitive Sliding Durability

A magnetic recording medium (tape) was made to slide at a sliding speed of 2 m/sec repeatedly for 10,000 passes under an environment of 40° C. and 10% RH with the magnetic layer surface in contact with an AlTiC cylindrical rod at a load of 100 g (T1), and tape damage was evaluated using the rankings below.

Excellent: slightly scratched, but area without scratches was larger.

Good: area with scratches was larger than area without scratches.

Poor: magnetic layer completely peeled off.

(4) Storage Properties 600 m of a magnetic recording medium (tape) was stored at 60° C. and 90% for 2 weeks while wound in a reel for an LTO-G3 cartridge.

The sliding durability of the tape after storage was measured by the same method as in (3).

The results are given in the tables below.

TABLE 6

| | | Magnetic substance | | | Smoothness | Electromagnetic conversion characteristics | Repetitive sliding durability | Storage properties |
|---|---|---|---|---|---|---|---|---|
| | PU | Type | Size | | | | | |
| Ex. 3-1 | 3-A | Acicular ferromagnetic fine powder | Major axis length | 35 nm | 75 | 0.7 | Excellent | Excellent |
| Ex. 3-2 | 3-B | Acicular ferromagnetic fine powder | Major axis length | 35 nm | 86 | 0.4 | Excellent | Excellent |
| Ex. 3-3 | 3-C | Acicular ferromagnetic fine powder | Major axis length | 35 nm | 73 | 0.8 | Excellent | Excellent |
| Ex. 3-4 | 3-D | Acicular ferromagnetic fine powder | Major axis length | 35 nm | 86 | 0.4 | Excellent | Excellent |
| Ex. 3-5 | 3-E | Acicular ferromagnetic fine powder | Major axis length | 35 nm | 74 | 0.7 | Excellent | Excellent |
| Ex. 3-6 | 3-F | Acicular ferromagnetic fine powder | Major axis length | 35 nm | 75 | 0.7 | Excellent | Excellent |
| Ex. 3-7 | 3-G | Acicular ferromagnetic fine powder | Major axis length | 35 nm | 80 | 0.6 | Excellent | Excellent |
| Ex. 3-8 | 3-H | Acicular ferromagnetic fine powder | Major axis length | 35 nm | 90 | 0.3 | Excellent | Excellent |
| Ex. 3-9 | 3-I | Acicular ferromagnetic fine powder | Major axis length | 35 nm | 90 | 0.3 | Excellent | Excellent |
| Ex. 3-10 | 3-A | Acicular ferromagnetic fine powder | Major axis length | 20 nm | 65 | 1 | Excellent | Excellent |
| Ex. 3-11 | 3-A | Acicular ferromagnetic fine powder | Major axis length | 50 nm | 85 | 0.4 | Excellent | Excellent |
| Ex. 3-12 | 3-B | Hexagonal tabular ferrite fine powder | Plate size | 10 nm | 65 | 1 | Excellent | Excellent |
| Ex. 3-13 | 3-B | Hexagonal tabular ferrite fine powder | Plate size | 50 nm | 78 | 0.6 | Excellent | Excellent |
| Ex. 3-14 | 3-A | Spherical iron nitride fine powder | Particle size | 10 nm | 65 | 1 | Excellent | Excellent |
| Ex. 3-15 | 3-A | Spherical iron nitride fine powder | Particle size | 50 nm | 80 | 0.6 | Excellent | Excellent |
| Comp. Ex. 3-1 | 3-J | Acicular ferromagnetic fine powder | Major axis length | 35 nm | 180 | −1.8 | Poor | Poor |
| Comp. Ex. 3-2 | 3-K | Acicular ferromagnetic fine powder | Major axis length | 35 nm | 100 | 0 | Poor | Poor |
| Comp. Ex. 3-3 | 3-L | Acicular ferromagnetic fine powder | Major axis length | 35 nm | 185 | −2 | Poor | Poor |

Acicular ferromagnetic fine powder: Hc 2,200 Oe, specific surface area 70 m$^2$/g, acicular ratio 3.5, σs 120 emu/g, Fe 89 atom %, Co 5 atom %, Y 6 atom %
Hexagonal tabular ferrite fine powder: Hc 2,200 Oe, specific surface area 55 m$^2$/g, plate ratio 3.5, σs 51 emu/g, Ba 91 atom %, Fe 8 atom %, Co 0.5 atom %, Zn 0.5 atom %
Spherical iron nitride fine powder: Hc 2,200 Oe, specific surface area 56 m$^2$/g, σs 100 emu/g, Fe 88 atom %, N 8 atom %, Y 4 atom %

TABLE 7

| | | Magnetic layer | | | Non-magnetic layer | | Electromagnetic conversion characteristics | Repetitive sliding durability | Storage properties |
|---|---|---|---|---|---|---|---|---|---|
| | | | Magnetic substance | | | | | | |
| | PU | Type | Size | | PU | Smoothness | | | |
| Ex. 3-16 | 3-A | Acicular ferromagnetic fine powder | Major axis length | 35 nm | 3-M | 60 | 1.3 | Excellent | Excellent |
| Ex. 3-17 | 3-A | Acicular ferromagnetic fine powder | Major axis length | 35 nm | 3-N | 63 | 1 | Excellent | Excellent |
| Ex. 3-18 | 3-A | Acicular ferromagnetic fine powder | Major axis length | 35 nm | 3-O | 65 | 1 | Excellent | Excellent |
| Ex. 3-19 | 3-A | Acicular ferromagnetic fine powder | Major axis length | 35 nm | 3-P | 65 | 1 | Excellent | Excellent |
| Comp. Ex. 3-4 | 3-A | Acicular ferromagnetic fine powder | Major axis length | 35 nm | 3-J | 120 | −0.7 | Poor | Poor |
| Comp. Ex. 3-5 | 3-A | Acicular ferromagnetic fine powder | Major axis length | 35 nm | 3-K | 90 | 0.3 | Poor | Poor |
| Comp. Ex. 3-6 | 3-A | Acicular ferromagnetic fine powder | Major axis length | 35 nm | 3-L | 130 | −0.9 | Poor | Poor |

Example 4

(4-1) Synthesis of Sulfonic Acid (Salt) Group-Containing Diol (4-1-1) Synthesis of Sulfonic Acid (Salt) Group-Containing Diol-1

100 parts by weight of 2-aminoethanesulfonic acid and 33.5 parts by weight of lithium hydroxide monohydrate were added to 250 parts by weight of water, and stirring was carried out at 45° C. for 30 minutes. 156 parts by weight of 1,2-butylene oxide was added thereto, and stirring was carried out at 45° C. for a further 2 hours. 400 parts by weight of toluene was added, stirring was carried out for 10 minutes, and a lower layer was then separated off after allowing it to stand. The lower layer thus obtained was solidified and dried, thus giving S4-1 below.

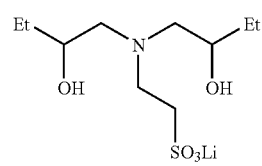

S4-1

(4-1-2) Synthesis of Sulfonic Acid (Salt) Group-Containing Diol-2

100 parts by weight of 2-aminoethanesulfonic acid and 44.8 parts by weight of potassium hydroxide were added to 250 parts by weight of water, and stirring was carried out at 45° C. for 30 minutes. 156 parts by weight of 1,2-butylene oxide was added thereto, and stirring was carried out at 45° C. for a further 2 hours. 400 parts by weight of toluene was added, stirring was carried out for 10 minutes, and a lower layer was then separated off after allowing it to stand. The lower layer thus obtained was solidified and dried, thus giving S4-2 and S4-3 at a ratio of 1:1.

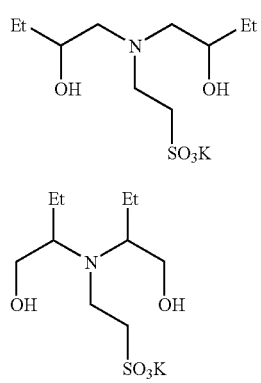

(4-2) Synthesis of Polyurethane (4-2-1) Polyurethane Synthesis-1 (Example 4-2-1)

2.4 parts by weight of S4-4 below, 39.8 parts by weight of BPX-1000 (Adeka Polyether), 21.6 parts by weight of tricyclo[5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

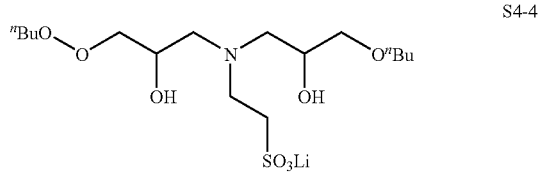

(4-2-2) Polyurethane Synthesis-2 (Example 4-2-2)

2.5 parts by weight of a sulfonic acid mixture containing S-2:S-64=1:1, 39.8 parts by weight of BPX-1000 (Adeka Polyether), 21.6 parts by weight of tricyclo[5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-3) Polyurethane Synthesis-3 (Example 4-2-3)

2.5 parts by weight of S-64, 39.6 parts by weight of BPX-1000 (Adeka Polyether), 21.6 parts by weight of tricyclo [5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-4) Polyurethane Synthesis-4 (Example 4-2-4)

1.7 parts by weight of S-1, 40.7 parts by weight of BPX-1000 (Adeka Polyether), 21.4 parts by weight of tricyclo [5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-5) Polyurethane Synthesis-5 (Example 4-2-5)

1.7 parts by weight of a sulfonic acid mixture containing S-1:S-34=1:1, 40.7 parts by weight of BPX-1000 (Adeka Polyether), 21.4 parts by weight of tricyclo[5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-6) Polyurethane Synthesis-6 (Example 4-2-6)

1.7 parts by weight of S-34, 40.7 parts by weight of BPX-1000 (Adeka Polyether), 21.4 parts by weight of tricyclo[5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-7) Polyurethane Synthesis-7 (Example 4-2-7)

1.8 parts by weight of a sulfonic acid mixture containing S4-2:S4-3=1:1, 40.5 parts by weight of BPX-1000 (Adeka Polyether), 21.4 parts by weight of tricyclo[5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-8) Polyurethane Synthesis-8 (Example 4-2-8)

14.0 parts by weight of S4-4, 32.0 parts by weight of BPX-1000 (Adeka Polyether), 17.8 parts by weight of tricyclo[5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-9) Polyurethane Synthesis-9 (Comparative Example 4-2-1)

5.7 parts by weight of a polyester-containing sulfonic acid compound having the structure below, 35.7 parts by weight of BPX-1000 (Adeka Polyether), 22.4 parts by weight of tricyclo[5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

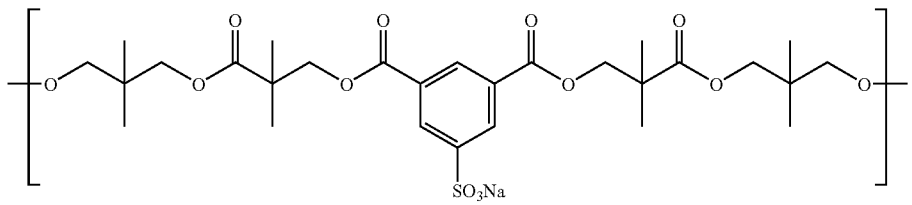

(4-2-10) Polyurethane Synthesis-10 (Comparative Example 4-2-2)

31.2 parts by weight of a polyester-containing sulfonic acid compound having the structure above, 10.6 parts by weight of BPX-1000 (Adeka Polyether), 21.9 parts by weight of tricyclo[5.2.1.0(2,6)]decanedimethanol (Tokyo Chemical Industry Co., Ltd.), and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-11) Polyurethane Synthesis-11 (Example 4-2-9)

2.5 parts by weight of S-2, 41.8 parts by weight of BPX-1000 (Adeka Polyether), 14.3 parts by weight of tricyclo[5.2.1.0(2,6)]decanedimethanol (Tokyo Chemical Industry Co., Ltd.), 5.11 parts by weight of BLEMMER GLM (NOF Corporation), 0.2 parts by weight of p-methoxyphenol, and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-2-12) Polyurethane Synthesis-12 (Example 4-2-10)

1.8 parts by weight of S4-2, 42.6 parts by weight of BPX-1000 (Adeka Polyether), 14.1 parts by weight of tricyclo[5.2.1.0(2,6)]decanedimethanol (Tokyo Chemical Industry Co., Ltd.), 5.1 parts by weight of BLEMMER GLM (NOF Corporation), 0.2 parts by weight of p-methoxyphenol, and 0.1 parts by weight of dibutyltin dilaurate were added to 54.1 parts by weight of cyclohexanone, and stirring was carried out at room temperature for 30 minutes, thus completing dissolution. The water content within the flask was measured using a Karl Fischer water content meter, and Millionate MT (Nippon Polyurethane) was added at 1 mole per mole of the water contained therein. After the internal temperature was set at 80° C., 71.9 parts by weight of a cyclohexanone solution containing 50 wt % of Millionate MT (Nippon Polyurethane) was added dropwise at a rate such that the internal temperature was 80° C. to 90° C. After stirring at an internal temperature of 80° C. to 90° C. for 4 hours, cooling to room temperature was carried out.

The polyurethane thus obtained had a weight-average molecular weight of 70,000 and the weight-average molecular weight/number-average molecular weight ratio Mw/Mn was 1.90. The weight-average molecular weight of the polyurethane was determined on a standard polystyrene basis using DMF solvent containing 0.3 wt % of lithium bromide.

(4-3) Dispersion Test (4-3-1) Dispersion test-1 (Example 4-3-1)

4.1 parts by weight of the non-magnetic powder below and 1 part by weight of the sulfonic acid group-containing polyurethane (sulfonic acid group content: $0.6 \times 10^{-4}$ eq/g) synthesized in (4-2-1) above, which contained the above S44, were suspended in a solution comprising 10.8 parts by weight of cyclohexanone and 16.2 parts by weight of 2-butanone. 90 parts by weight of zirconia beads (Nikkato Corporation) was added to the suspension and dispersion was carried out for 6 hours. A sheet was obtained by applying the solution thus obtained and drying it. When the gloss of the sheet was measured, it was 190.

Non-magnetic powder: α-iron oxide (surface treatment layer: $Al_2O_3$, $SiO_2$)

Average major axis length: 0.15 μm, average acicular ratio: 7, specific surface area by BET method: 52 $m^2/g$, pH 8

(4-3-2) Dispersion Test-2 (Example 4-3-2)

7.3 parts by weight of the barium ferrite powder below and 1 part by weight of the sulfonic acid group-containing polyurethane (sulfonic acid group content: $3.3 \times 10^{-4}$ mol/g) synthesized in (4-24), which contained S-1, were suspended in a solution comprising 11.9 parts by weight of cyclohexanone and 17.7 parts by weight of 2-butanone. 90 parts by weight of zirconia beads (Nikkato Corporation) was added to the suspension and dispersion was carried out for 6 hours. The ratio of polyurethane present on the barium ferrite powder surface to that present in the dispersed solution was measured by the method below, and was found to be 4.0/1. The sulfur content in the polyurethane in the solution was measured using X-ray fluorescence, and it was below the detection limit. A sheet was obtained by applying the solution thus obtained and drying it. When the gloss of the sheet was measured, it was 171.

Ferromagnetic Hexagonal Barium Ferrite Powder

Composition excluding oxygen (molar ratio): Ba/Fe/Co/Zn=1/9/0.2/1

Hc: 176 kA/m (2200 Oe), average plate size: 25 nm, average plate ratio: 3

BET specific surface area: 65 m$^2$/g

σs: 49 A·m$^2$/kg (49 emu/g)

pH: 7

—Method for Measuring Ratio of Polyurethane Present—

A dispersion was subjected to centrifugation using a CS150GXL preparative micro ultracentrifuge manufactured by Hitachi Koki Co., Ltd. under conditions of 100,000 rpm and 80 minutes, thus separating a ferromagnetic powder and a solution. 3 mL of the supernatant fluid was sampled and weighed. After drying under conditions of 40° C. for 18 hours, it was dried under conditions of 140° C. for 3 hours under vacuum. The weight of dried material was defined as that for non-adsorbed binder solids, and a ratio of binder present on the surface of the ferromagnetic powder (barium ferrite powder)/binder present in solution was calculated from the ratio of binder used for dispersion to binder observed in the supernatant.

(4-3-3) Dispersion Test-3 (Example 4-3-3)

4.1 parts by weight of the non-magnetic powder below and 1 part by weight of the sulfonic acid group-containing polyurethane (sulfonic acid group content: 0.6×10$^4$ eq/g) synthesized in (4-2-6) above, which contained S-34, were suspended in a solution comprising 10.8 parts by weight of cyclohexanone and 16.2 parts by weight of 2-butanone. 90 parts by weight of zirconia beads (Nikkato Corporation) was added to the suspension and dispersion was carried out for 6 hours. A sheet was obtained by applying the solution thus obtained to a PEN film (Teijin Ltd.) and drying it. When the gloss of the sheet was measured, it was 191.

Non-magnetic powder: α-iron oxide (surface treatment layer: Al$_2$O$_3$, SiO$_2$)

Average major axis length: 0.15 μm, average acicular ratio: 7, specific surface area by BET method: 52 m$^2$/g, pH 8

(4-3-4) Dispersion Test-4 (Example 4-34)

4.1 parts by weight of the non-magnetic powder below and 1 part by weight of the sulfonic acid group-containing polyurethane (sulfonic acid group content: 0.6×10$^{-4}$ eq/g) synthesized in (4-2-7) above, which contained S4-2:S4-3=1:1, were suspended in a solution comprising 10.8 parts by weight of cyclohexanone and 16.2 parts by weight of 2-butanone. 90 parts by weight of zirconia beads (Nikkato Corporation) was added to the suspension and dispersion was carried out for 6 hours. A sheet was obtained by applying the solution thus obtained to a PEN film (Teijin Ltd.) and drying it. When the gloss of the sheet was measured, it was 194.

Non-magnetic powder: α-iron oxide (surface treatment layer: Al$_2$O$_3$, SiO$_2$)

Average major axis length: 0.15 μm, average acicular ratio: 7, specific surface area by BET method: 52 m$^2$/g, pH 8

(4-3-5) Dispersion Test-5 (Example 4-3-5)

4.1 parts by weight of the barium ferrite powder below and 1 part by weight of the sulfonic acid group-containing polyurethane (sulfonic acid group content: 3.3×10$^{-4}$ eq/g) synthesized in (4-2-8) above, which contained the above S44, were suspended in a solution comprising 10.8 parts by weight of cyclohexanone and 16.2 parts by weight of 2-butanone. 90 parts by weight of zirconia beads (Nikkato Corporation) was added to the suspension and dispersion was carried out for 6 hours. A sheet was obtained by applying the solution thus obtained and drying it. When the gloss of the sheet was measured, it was 183.

Ferromagnetic Hexagonal Barium Ferrite Powder

Composition excluding oxygen (molar ratio): Ba/Fe/Co/Zn=1/9/0.2/1

Hc: 176 kA/m (2200 Oe), average plate size: 25 nm, average plate ratio: 3

BET specific surface area: 65 m$^2$/g

σs: 49 A·m$^2$/kg (49 emu/g)

pH: 7

(4-3-6) Dispersion Test-6 (Comparative Example 4-3-1)

4.1 parts by weight of the non-magnetic powder below and 1 part by weight of the sulfonic acid group-containing polyurethane (sulfonic acid group content: 0.6×10$^{-4}$ mol/g) synthesized in (4-2-9) above, which contained polyester, were suspended in a solution comprising 10.8 parts by weight of cyclohexanone and 16.2 parts by weight of 2-butanone. 90 parts by weight of zirconia beads (Nikkato Corporation) was added to the suspension and dispersion was carried out for 6 hours. The ratio of polyurethane present on the non-magnetic powder surface to that present in the dispersed solution was measured by the method below, and was found to be 2.7/1. The sulfur content in the polyurethane in the solution was measured using X-ray fluorescence, and it was below the detection limit.

A sheet was obtained by applying the solution thus obtained and drying it. When the gloss of the sheet was measured, it was 145.

Non-magnetic powder: α-iron oxide (surface treatment layer: Al$_2$O$_3$, SiO$_2$)

Average major axis length: 0.15 μm, average acicular ratio: 7, specific surface area by BET method: 52 m$^2$/g, pH 8

(4-3-7) Dispersion Test-7 (Comparative Example 4-3-2)

7.3 parts by weight of the barium ferrite powder below and 1 part by weight of the sulfonic acid group-containing polyurethane (sulfonic acid group content: 3.3×10$^{-4}$ mol/g) synthesized in (4-2-10) above, which contained polyester, were suspended in a solution comprising 11.9 parts by weight of cyclohexanone and 17.7 parts by weight of 2-butanone. 90 parts by weight of zirconia beads (Nikkato Corporation) was added to the suspension and dispersion was carried out for 6 hours. The ratio of polyurethane present on the non-magnetic powder surface to that present in the dispersed solution was measured by the method below, and was found to be 2.6/1. The sulfur content in the polyurethane in the solution was measured using X-ray fluorescence, and it was below the detection limit.

A sheet was obtained by applying the solution thus obtained and drying it. When the gloss of the sheet was measured, it was 180.

Ferromagnetic Hexagonal Barium Ferrite Powder

Composition excluding oxygen (molar ratio): Ba/Fe/Co/Zn=1/9/0.2/1

Hc: 176 kA/m (2200 Oe), average plate size: 25 nm, average plate ratio: 3

BET specific surface area: 65 m²/g

σs: 49 A·m²/kg (49 emu/g)

pH: 7

(4-3-8) Dispersion Test-8 (Example 4-3-6)

4.1 parts by weight of the non-magnetic powder below and 1 part by weight of the sulfonic acid group-containing polyurethane (sulfonic acid group content: $0.6 \times 10^{-4}$ eq/g) synthesized in (4-2-10) above, were suspended in a solution comprising 10.8 parts by weight of cyclohexanone and 16.2 parts by weight of 2-butanone. 90 parts by weight of zirconia beads (Nikkato Corporation) was added to the suspension and dispersion was carried out for 6 hours. A sheet was obtained by applying the solution thus obtained and drying it. When the gloss of the sheet was measured, it was 190.

Non-magnetic powder: α-iron oxide (surface treatment layer: $Al_2O_3$, $SiO_2$)

Average major axis length: 0.15 μm, average acicular ratio: 7, specific surface area by BET method: 52 m²/g, pH 8

(4-3-9) Dispersion Test-9 (Example 4-3-7)

4.1 parts by weight of the non-magnetic powder above and 1 part by weight of the polyurethane (sulfonic acid group content: $0.6 \times 10^{-4}$ mol/g) synthesized in (4-2-11) above, which contained S-2, were suspended in a solution comprising 10.8 parts by weight of cyclohexanone and 16.2 parts by weight of 2-butanone. 90 parts by weight of zirconia beads (Nikkato Corporation) was added to the suspension and dispersion was carried out for 6 hours. The ratio of polyurethane present on the non-magnetic powder surface to that present in the solution for the dispersion was measured by the method below, and was found to be 2.7/1. The sulfur content in the polyurethane in the solution was measured using X-ray fluorescence, and it was below the detection limit.

A sheet was obtained by applying the solution thus obtained and drying it. When the gloss of the sheet was measured, it was 193.

Non-magnetic powder: α-iron oxide (surface treatment layer: $Al_2O_3$, $SiO_2$)

Average major axis length: 0.15 μm, average acicular ratio: 7, specific surface area by BET method: 52 m²/g, pH 8

The gloss value was measured using a GK-45D manufactured by Suga Test Instruments Co. Ltd.

(4-4) Electron Beam Curing Test

The polyurethane solutions synthesized in the polyurethane synthesis methods-1, 10, and 11 above (Examples 4-2-1, 4-2-9, and 4-2-10) were applied to glass plates and dried to give sheets having a coating thickness of 20 μm.

The polyurethane on the glass plate was irradiated with an electron beam at 20 kGy.

After irradiation with the electron beam, the polyurethane on the surface of the glass plate was scraped off and added to THF, and extraction was carried out at 60° C. for 2 hours. A gel fraction=(proportion of residue after extraction) I (initial sampling amount) was determined and used for evaluation of curability by irradiation with an electron beam (solvent durability).

TABLE 8

| Polyurethane   | Gel Fraction (%) |
|----------------|------------------|
| Synthesis - 1  | 0                |
| Synthesis - 10 | 91               |
| Synthesis - 11 | 89               |

Example 5

(5-1) Synthesis of Sulfonic Acid (Salt) Group-Containing Diol 100 parts by weight of 2-aminoethanesulfonic acid and 44.8 parts by weight of potassium oxide were added to 250 parts by weight of water, and stirring was carried out at 45° C. for 30 minutes. 115 parts by weight of 1,2-butylene oxide was added, and stirring was carried out at 45° C. for a further 2 hours. The reaction mixture was concentrated to dryness, and it was confirmed by $^1$H-NMR that S5-1:S5-2=1:1.

1 part by weight of a mixture comprising S5-1 and S5-2 was dissolved in 10 parts by weight of water, converted into an aqueous solution of S5-3:S5-4=1:1 using a strongly acidic ion-exchange resin, and then neutralized using a 1 N lithium hydroxide aqueous solution so as to give a pH of 6 to 8. The aqueous solution thus obtained was concentrated to dryness, thus giving a viscous material with S5-5:S5-6=1:1.

100 parts by weight (1 molar equivalent) of 2-aminoethanesulfonic acid and 33.5 parts by weight (1 molar equivalent) of lithium hydroxide monohydrate were added to 250 parts by weight of water, and stirring was carried out at 45° C. for 30 minutes. 156 parts by weight of 1,2-butylene oxide was added, and stirring was carried out at 45° C. for a further 2 hours. The reaction mixture was concentrated to dryness, and it was confirmed by $^1$H-NMR to be S5-6.

1 part by weight of S5-6 was dissolved in 10 parts by weight of water, converted into S5-4 using a strongly acidic ion-exchange resin, and neutralized using a 1N potassium hydroxide aqueous solution so as to give a pH of 6 to 8. The aqueous solution thus obtained was concentrated to dryness, thus giving S5-2 as a viscous material.

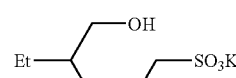

S5-1

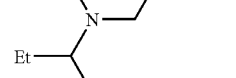

S5-2

-continued

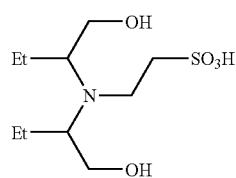
S5-3

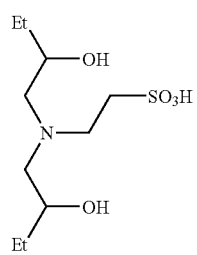
S5-4

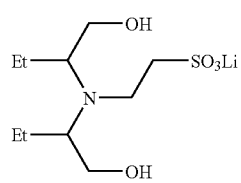
S5-5

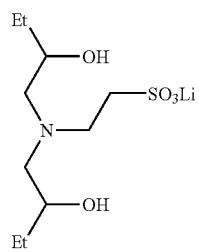
S5-6

(5-2) Solubility Test Method

Mixtures of S5-1, S5-2, S5-5, and S5-6 at given ratios were added to cyclohexanone, and dissolution was carried out at 40° C. for 3 hours using ultrasonic waves. The solutions thus obtained were filtered, and the presence/absence of a residue after dissolution was checked (the numbers in the table are expressed as parts by weight).

TABLE 9

| No. | S5-1 | S5-2 | S5-5 | S5-6 | Cyclohexanone | Insolubles |
|---|---|---|---|---|---|---|
| 5-1 | 0 | 4 | 0 | 0 | 4 | Some |
| 5-2 | 0 | 4 | 0 | 0 | 20 | None |
| 5-3 | 2 | 2 | 0 | 0 | 4 | None |
| 5-4 | 2 | 2 | 0 | 0 | 20 | None |
| 5-5 | 0 | 2 | 0 | 2 | 4 | None |
| 5-6 | 0 | 2 | 0 | 2 | 20 | None |
| 5-7 | 1 | 1 | 1 | 1 | 4 | None |
| 5-8 | 1 | 1 | 1 | 1 | 20 | None |
| 5-9 | 0 | 0 | 0 | 4 | 4 | Some |
| 5-10 | 0 | 0 | 0 | 4 | 20 | None |
| 5-11 | 0 | 0 | 2 | 2 | 4 | None |
| 5-12 | 0 | 0 | 2 | 2 | 20 | None |

What is claimed is:

1. A polyurethane resin obtained by polymerization of a polyol and a polyisocyanate, wherein the polyol comprises, a compound, selected from the group consisting of compounds (S-2) to (S-18), (S-20) to (S-27), (S-30) to (S-33), (S-35) to (S-51), (S-53) to (S-60) and (S-63) to (S-70):

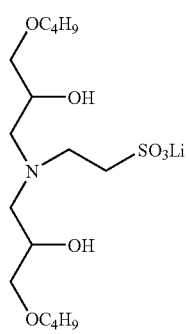
(S-2)

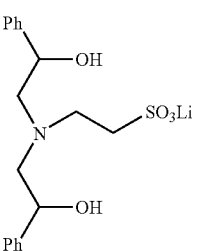
(S-3)

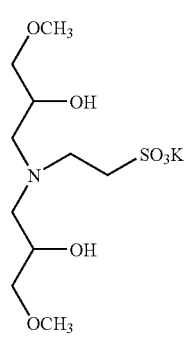
(S-4)

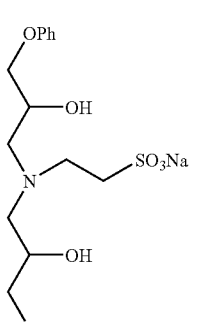
(S-5)

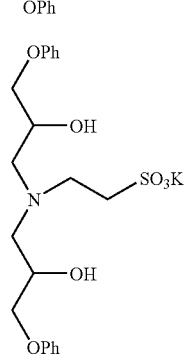
(S-6)

(S-7) 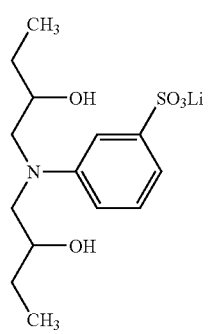
(S-8) 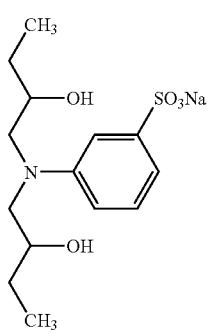
(S-9) 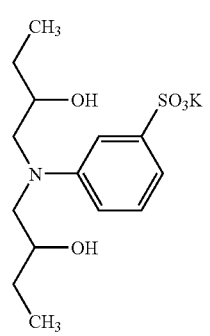
(S-10) 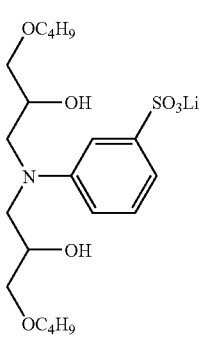
(S-11) 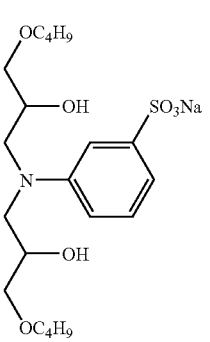
(S-12) 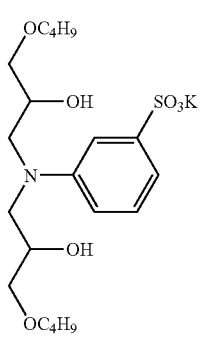
(S-13) 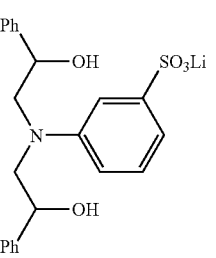
(S-14) 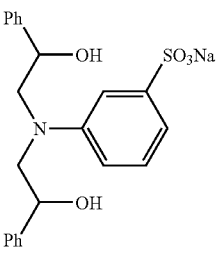
(S-15) 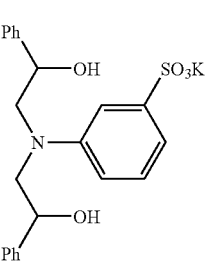
(S-16) 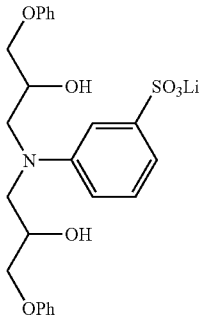

-continued
(S-17)
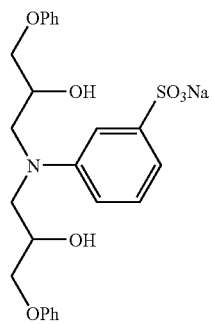
(S-18)
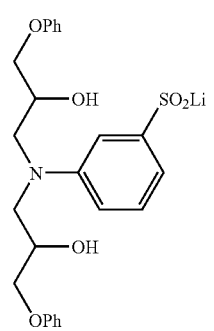
(S-20)
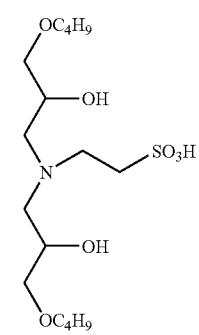
(S-21)
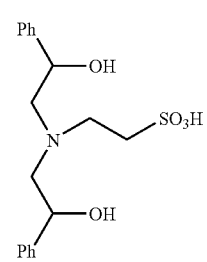
(S-22)
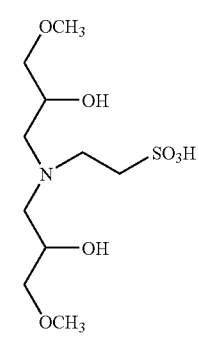
-continued
(S-23)
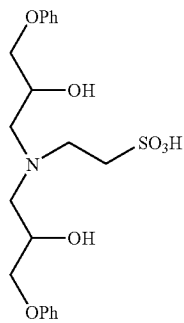
(S-24)
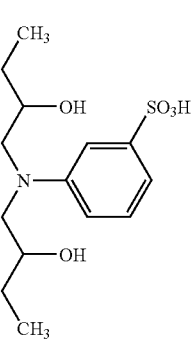
(S-25)
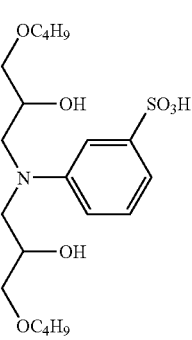
(S-26)
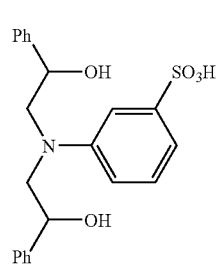
(S-27)
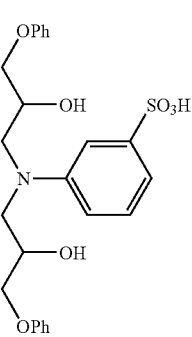

(S-30), (S-31), (S-32), (S-33), (S-35), (S-36), (S-37), (S-38), (S-39), (S-40), (S-41), (S-42), (S-43), (S-44), (S-45)

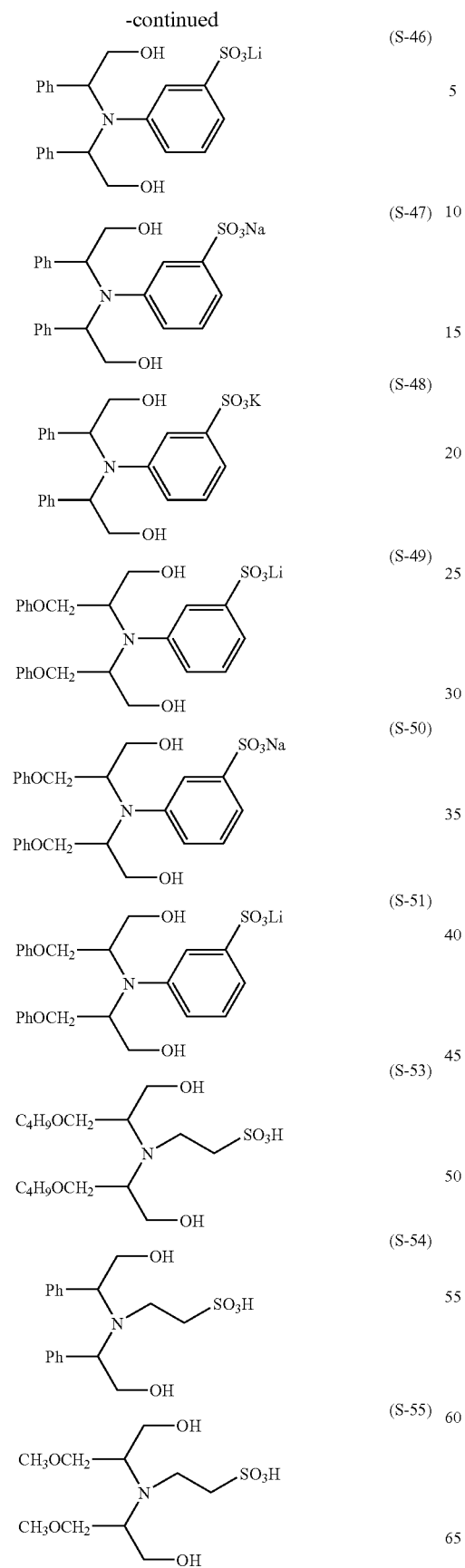
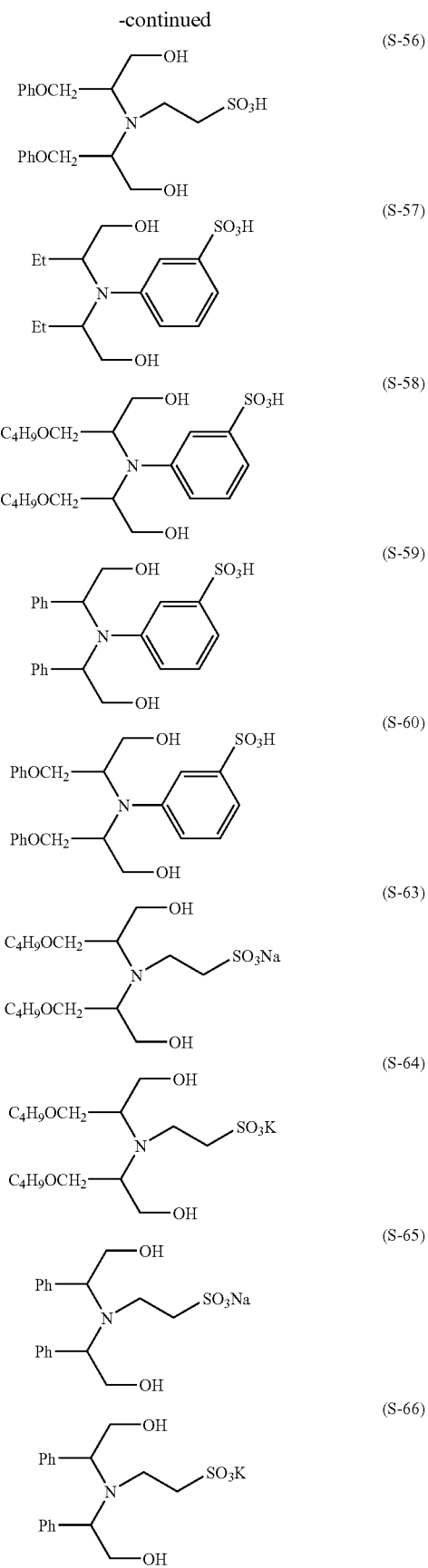

-continued

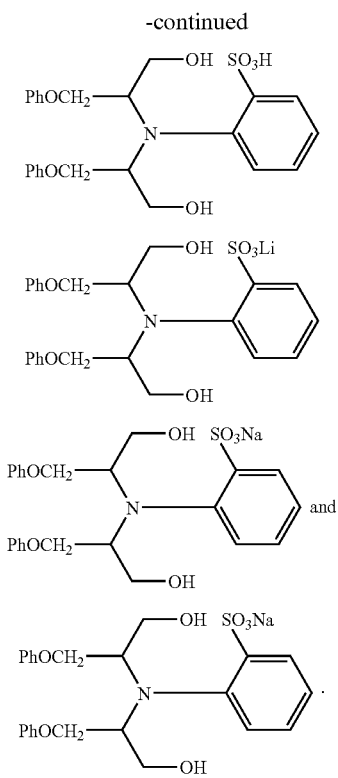

2. The polyurethane resin according to claim 1, wherein the polyol comprises a compound, selected from the group consisting of compounds (S-2) to (S-6), (S-10) to (S-18), (S-20) to (S-23), (S-25) to (S-27), (S-30) to (S-33), (S-35) to (S-39), (S-43) to (S-51), (S-53) to (S-56), (S-58) to (S-60) and (S-63) to (S-70).

3. The polyurethane resin according to claim 1, which has a sulfonic acid (salt) group content of at least $1\times10^{-5}$ eq/g but no greater than $2\times10^{-3}$ eq/g.

4. The polyurethane resin according to claim 1, wherein the polyol further comprises a (meth)acryloyloxy group-containing diol.

5. A magnetic recording medium comprising the polyurethane resin according to claim 1.

6. A magnetic recording medium comprising a non-magnetic support and, above the support, at least one magnetic layer comprising a ferromagnetic powder dispersed in a binder,
the binder comprising the polyurethane resin according to claim 1.

7. A magnetic recording medium comprising a non-magnetic support, above the support at least one non-magnetic layer comprising a non-magnetic powder dispersed in a binder (1), and, above the non-magnetic layer, at least one magnetic layer comprising a ferromagnetic powder dispersed in a binder (2),
binder (1) and/or binder (2) being the polyurethane resin according to claim 1.

8. The magnetic recording medium according to claim 7, wherein the polyol further comprises a (meth)acryloyloxy group-containing diol.

9. The magnetic recording medium according to claim 6, wherein the ferromagnetic powder is at least one type selected from the group consisting of an acicular ferromagnetic substance having an average major axis length of at least 20 nm but no greater than 50 nm, a tabular ferromagnetic substance having an average plate size of at least 10 nm but no greater than 50 nm, and a spherical or spheroidal magnetic substance having an average diameter of at least 10 nm but no greater than 50 nm.

* * * * *